United States Patent
Caputo et al.

(10) Patent No.: US 8,287,364 B2
(45) Date of Patent: Oct. 16, 2012

(54) GAMING SYSTEM, GAMING DEVICE, AND METHOD FOR PROVIDING A GAME IN WHICH A PLAYER COLLECTS EMBLEMS BY POSITIONING ACCUMULATORS IN A FIELD

(75) Inventors: Scott A. Caputo, Santa Clara, CA (US); Mark C. Nicely, Daly City, CA (US)

(73) Assignee: IGT, Reno, NV (US)

( * ) Notice: Subject to any disclaimer, the term of this patent is extended or adjusted under 35 U.S.C. 154(b) by 1007 days.

(21) Appl. No.: 12/270,472

(22) Filed: Nov. 13, 2008

(65) Prior Publication Data
US 2010/0120505 A1    May 13, 2010

(51) Int. Cl.
  A63F 9/24    (2006.01)
  A63F 13/00   (2006.01)
  G06F 17/00   (2006.01)
  G06F 19/00   (2011.01)
(52) U.S. Cl. .............. 463/26; 463/19; 463/20; 463/21
(58) Field of Classification Search ............. 463/26
  See application file for complete search history.

(56) References Cited

U.S. PATENT DOCUMENTS

| | | |
|---|---|---|
| 3,167,313 A | 1/1965 | Davenport et al. |
| 4,003,578 A | 1/1977 | Jones |
| 4,103,895 A | 8/1978 | Pressman et al. |
| 4,182,515 A | 1/1980 | Nemeth |
| 4,251,078 A | 2/1981 | Meirovitz |
| 4,277,067 A | 7/1981 | Gettleman |
| 4,323,242 A | 4/1982 | Rosenfeld |
| 4,511,143 A | 4/1985 | Sankrithi |
| 4,548,410 A | 10/1985 | Morrone |
| 4,820,908 A | 4/1989 | Wei |
| 4,850,592 A | 7/1989 | Winter |
| 5,080,368 A | 1/1992 | Weisser |
| 5,083,800 A | 1/1992 | Lockton |

(Continued)

FOREIGN PATENT DOCUMENTS

EP    0 945 837    9/1999

(Continued)

OTHER PUBLICATIONS

Article entitled "Battle Plan" in Strictly Slots, published Sep. 2000.

(Continued)

*Primary Examiner* — Dmitry Suhol
*Assistant Examiner* — Kevin Y Kim
(74) *Attorney, Agent, or Firm* — Neal, Gerber & Eisenberg LLP

(57) ABSTRACT

A gaming system displays a plurality of emblems in a predefined field. For a play of an accumulator positioning game, the gaming system enables a player to position at least one accumulator in the field based on a set of accumulator positioning criteria. The accumulator positioning criteria define allowable accumulator positions and also define whether a positioned accumulator causes the gaming system to indicate any of the emblems as winning emblems. The gaming system may indicate such winning emblems based on a spatial relationship between that emblem and any accumulator, such as a relationship wherein an accumulator encircles an emblem. The gaming system indicates any such winning emblems and provides an award for the play of the game based on any indicated winning emblems.

32 Claims, 21 Drawing Sheets

U.S. PATENT DOCUMENTS

| | | | |
|---|---|---|---|
| 5,178,395 A | 1/1993 | Lovell | |
| 5,178,545 A | 1/1993 | Thompson | |
| 5,333,868 A | 8/1994 | Goldfarb | |
| 5,342,049 A | 8/1994 | Wichinsky et al. | |
| 5,355,442 A | 10/1994 | Paglieroni et al. | |
| 5,566,942 A | 10/1996 | Elum | |
| 5,611,730 A | 3/1997 | Weiss | |
| 5,664,998 A | 9/1997 | Seelig et al. | |
| 5,769,716 A | 6/1998 | Saffari et al. | |
| 5,772,509 A | 6/1998 | Weiss | |
| 5,779,545 A | 7/1998 | Berg et al. | |
| 5,813,672 A | 9/1998 | Loud, Jr. | |
| 5,855,514 A | 1/1999 | Kamille | |
| 5,931,467 A | 8/1999 | Kamille | |
| 5,947,820 A | 9/1999 | Morro et al. | |
| 5,961,384 A | 10/1999 | Robinson | |
| 5,980,384 A | 11/1999 | Barrie | |
| 6,015,346 A | 1/2000 | Bennett | |
| 6,089,976 A | 7/2000 | Schneider et al. | |
| 6,102,798 A | 8/2000 | Bennett | |
| 6,126,542 A | 10/2000 | Fier | |
| 6,134,556 A | 10/2000 | Shin | |
| 6,159,095 A | 12/2000 | Frohm et al. | |
| 6,159,098 A * | 12/2000 | Slomiany et al. | 463/25 |
| 6,165,070 A | 12/2000 | Nolte et al. | |
| 6,254,481 B1 | 7/2001 | Jaffe | |
| 6,257,981 B1 | 7/2001 | Acres et al. | |
| 6,261,177 B1 | 7/2001 | Bennett | |
| 6,273,420 B1 | 8/2001 | Brooks | |
| 6,309,299 B1 | 10/2001 | Weiss | |
| 6,309,300 B1 | 10/2001 | Glavich | |
| 6,315,660 B1 | 11/2001 | DeMar et al. | |
| 6,315,664 B1 | 11/2001 | Baerlocher et al. | |
| 6,319,124 B1 | 11/2001 | Baerlocher et al. | |
| 6,328,649 B1 | 12/2001 | Randall et al. | |
| 6,340,159 B1 | 1/2002 | Giangrante | |
| 6,346,043 B1 | 2/2002 | Colin et al. | |
| 6,347,996 B1 | 2/2002 | Gilmore et al. | |
| 6,364,767 B1 | 4/2002 | Brossard et al. | |
| 6,386,974 B1 | 5/2002 | Adams | |
| 6,398,644 B1 | 6/2002 | Perrie et al. | |
| 6,406,369 B1 | 6/2002 | Baerlocher et al. | |
| 6,419,226 B2 | 7/2002 | Krise et al. | |
| 6,425,824 B1 | 7/2002 | Baerlocher et al. | |
| 6,428,412 B1 | 8/2002 | Anderson et al. | |
| 6,439,995 B1 | 8/2002 | Hughs-Baird et al. | |
| 6,443,837 B1 | 9/2002 | Jaffe et al. | |
| 6,450,883 B1 | 9/2002 | O'Halloran | |
| 6,494,785 B1 | 12/2002 | Gerrard et al. | |
| 6,511,375 B1 | 1/2003 | Kaminkow | |
| 6,514,141 B1 | 2/2003 | Kaminkow et al. | |
| 6,558,254 B2 | 5/2003 | Baelocher et al. | |
| 6,572,469 B2 | 6/2003 | Klitsner et al. | |
| 6,572,472 B1 | 6/2003 | Glavich | |
| 6,572,473 B1 | 6/2003 | Baerlocher | |
| 6,579,178 B1 | 6/2003 | Walker et al. | |
| 6,582,307 B2 | 6/2003 | Webb | |
| 6,589,117 B1 | 7/2003 | Moritome et al. | |
| 6,595,854 B2 | 7/2003 | Hughs-Baird et al. | |
| 6,599,185 B1 | 7/2003 | Kaminkow et al. | |
| 6,602,136 B1 | 8/2003 | Baerlocher et al. | |
| 6,602,137 B2 | 8/2003 | Kaminkow et al. | |
| 6,607,438 B2 | 8/2003 | Baerlocher et al. | |
| 6,632,141 B2 | 10/2003 | Webb et al. | |
| 6,638,164 B2 | 10/2003 | Randall et al. | |
| 6,641,137 B2 | 11/2003 | Sines et al. | |
| 6,645,071 B2 | 11/2003 | Perrie et al. | |
| 6,645,073 B2 | 11/2003 | Lemay et al. | |
| 6,645,074 B2 | 11/2003 | Thomas et al. | |
| 6,656,040 B1 | 12/2003 | Brossman et al. | |
| 6,666,766 B2 | 12/2003 | Baerlocher et al. | |
| 6,676,516 B2 | 1/2004 | Baerlocher et al. | |
| 6,692,356 B2 | 2/2004 | Baerlocher et al. | |
| 6,722,981 B2 | 4/2004 | Kaminkow et al. | |
| 6,722,982 B2 | 4/2004 | Kaminkow et al. | |
| 6,733,386 B2 | 5/2004 | Cuddy et al. | |
| 6,743,096 B2 | 6/2004 | Allendorf et al. | |
| 6,749,504 B2 | 6/2004 | Hughs-Baird | |
| 6,752,312 B1 | 6/2004 | Chamberlain et al. | |
| 6,758,747 B2 | 7/2004 | Baerlocher | |
| 6,769,983 B2 | 8/2004 | Slomiany | |
| 6,780,107 B2 | 8/2004 | Baerlocher et al. | |
| 6,780,110 B2 | 8/2004 | Baerlocher et al. | |
| 6,780,111 B2 | 8/2004 | Cannon et al. | |
| 6,783,455 B2 | 8/2004 | Glavich | |
| 6,783,457 B2 | 8/2004 | Hughs-Baird et al. | |
| 6,786,820 B2 | 9/2004 | Gerrard et al. | |
| 6,808,454 B2 | 10/2004 | Gerrard et al. | |
| 6,814,664 B2 | 11/2004 | Baerlocher et al. | |
| 6,817,944 B2 | 11/2004 | Kaminkow et al. | |
| 6,837,793 B2 | 1/2005 | McClintic | |
| 6,840,856 B2 | 1/2005 | Stern | |
| 6,843,722 B2 | 1/2005 | Webb | |
| 6,852,027 B2 | 2/2005 | Kaminkow et al. | |
| 6,863,606 B1 | 3/2005 | Berg et al. | |
| 6,875,108 B1 | 4/2005 | Hughs-Baird | |
| 6,899,620 B2 | 5/2005 | Kaminkow et al. | |
| 6,902,478 B2 | 6/2005 | McClintic | |
| 6,908,383 B2 | 6/2005 | Baerlocher et al. | |
| 6,913,533 B2 | 7/2005 | Cuddy et al. | |
| 6,918,830 B2 | 7/2005 | Baerlocher | |
| 6,932,701 B2 | 8/2005 | Glavich et al. | |
| 6,958,013 B2 | 10/2005 | Miereau et al. | |
| 6,966,833 B2 | 11/2005 | Kaminkow et al. | |
| 6,971,953 B2 | 12/2005 | Gerrard et al. | |
| 6,971,954 B2 | 12/2005 | Randall et al. | |
| 6,988,947 B2 | 1/2006 | Baerlocher et al. | |
| 6,988,948 B2 | 1/2006 | Perrie et al. | |
| 6,995,751 B2 | 2/2006 | Falvo | |
| 6,996,833 B1 | 2/2006 | Olson et al. | |
| 7,037,191 B2 | 5/2006 | Rodgers et al. | |
| 7,040,984 B2 | 5/2006 | Mead | |
| 7,052,392 B2 | 5/2006 | Tessmer et al. | |
| 7,056,214 B2 | 6/2006 | Miereau et al. | |
| 7,077,744 B2 | 7/2006 | Cannon | |
| 7,104,888 B2 | 9/2006 | Miereau et al. | |
| 7,112,137 B2 | 9/2006 | Baerlocher et al. | |
| 7,121,942 B2 | 10/2006 | Baerlocher | |
| 7,160,186 B2 | 1/2007 | Cuddy et al. | |
| 7,160,188 B2 | 1/2007 | Kaminkow et al. | |
| 7,168,704 B1 | 1/2007 | Lawless | |
| 7,169,044 B2 | 1/2007 | Baerlocher et al. | |
| 7,172,506 B2 | 2/2007 | Baerlocher et al. | |
| 7,175,523 B2 | 2/2007 | Gilmore et al. | |
| 7,179,166 B1 | 2/2007 | Abbott | |
| 7,182,689 B2 | 2/2007 | Hughs-Baird et al. | |
| 7,198,570 B2 | 4/2007 | Rodgers et al. | |
| 7,201,657 B2 | 4/2007 | Baerlocher et al. | |
| 7,235,011 B2 | 6/2007 | Randall et al. | |
| 7,264,545 B2 | 9/2007 | Maya et al. | |
| 7,294,058 B1 | 11/2007 | Slomiany et al. | |
| 7,300,348 B2 | 11/2007 | Kaminkow et al. | |
| 7,303,469 B2 | 12/2007 | Kaminkow et al. | |
| 7,311,598 B2 | 12/2007 | Kaminkow et al. | |
| 7,311,604 B2 | 12/2007 | Kaminkow et al. | |
| 7,314,408 B2 | 1/2008 | Cannon | |
| 7,314,409 B2 | 1/2008 | Maya et al. | |
| 7,318,773 B2 | 1/2008 | Baerlocher | |
| 7,326,115 B2 | 2/2008 | Baerlocher | |
| 7,329,184 B2 | 2/2008 | Yoshioka | |
| 7,335,102 B2 | 2/2008 | Baerlocher et al. | |
| 7,338,367 B2 | 3/2008 | Kaminkow et al. | |
| 7,338,369 B2 | 3/2008 | Mierau et al. | |
| 7,351,140 B2 | 4/2008 | Wolf et al. | |
| 7,357,714 B2 | 4/2008 | Tessmer et al. | |
| 7,361,087 B2 | 4/2008 | Baerlocher et al. | |
| 7,393,280 B2 | 7/2008 | Cannon | |
| 7,427,235 B2 | 9/2008 | Anderson et al. | |
| 7,485,038 B2 | 2/2009 | Rothkranz et al. | |
| 2002/0052232 A1 | 5/2002 | Kaminkow | |
| 2003/0013514 A1 | 1/2003 | Cregan et al. | |
| 2003/0036422 A1 | 2/2003 | Baerlocher et al. | |
| 2003/0036424 A1 | 2/2003 | Baerlocher | |
| 2003/0040358 A1 | 2/2003 | Rothkranz et al. | |
| 2003/0064773 A1 | 4/2003 | Baerlocher et al. | |
| 2003/0078096 A1 | 4/2003 | Kaminkow et al. | |
| 2003/0153378 A1 | 8/2003 | Schlegel et al. | |

| Publication No. | Date | Inventor |
|---|---|---|
| 2003/0157982 A1 | 8/2003 | Gerrard et al. |
| 2003/0162578 A1 | 8/2003 | Baerlocher et al. |
| 2003/0186733 A1 | 10/2003 | Wolf et al. |
| 2004/0048644 A1 | 3/2004 | Gerrard et al. |
| 2004/0048649 A1 | 3/2004 | Peterson et al. |
| 2004/0048657 A1* | 3/2004 | Gauselmann ............... 463/25 |
| 2004/0053665 A1 | 3/2004 | Baerlocher |
| 2004/0106444 A1 | 6/2004 | Cuddy et al. |
| 2004/0176156 A1 | 9/2004 | Walker et al. |
| 2004/0242315 A1 | 12/2004 | Paulsen et al. |
| 2004/0248639 A1 | 12/2004 | Slomiany |
| 2005/0020351 A1 | 1/2005 | Baerlocher et al. |
| 2005/0033461 A1 | 2/2005 | Gerrard et al. |
| 2005/0054404 A1 | 3/2005 | Baerlocher |
| 2005/0054405 A1 | 3/2005 | Baerlocher et al. |
| 2005/0054415 A1 | 3/2005 | Kaminkow et al. |
| 2005/0054416 A1 | 3/2005 | Hostetler et al. |
| 2005/0054435 A1 | 3/2005 | Rodgers et al. |
| 2005/0054436 A1 | 3/2005 | Frizzell et al. |
| 2005/0059456 A1 | 3/2005 | Mead et al. |
| 2005/0059460 A1 | 3/2005 | Breen et al. |
| 2005/0059461 A1 | 3/2005 | Ching et al. |
| 2005/0064928 A1 | 3/2005 | Baerlocher et al. |
| 2005/0096114 A1 | 5/2005 | Cannon et al. |
| 2005/0096123 A1 | 5/2005 | Cregan et al. |
| 2005/0101372 A1 | 5/2005 | Mierau et al. |
| 2005/0101378 A1 | 5/2005 | Kaminkow et al. |
| 2005/0181860 A1 | 8/2005 | Nguyen et al. |
| 2005/0192081 A1 | 9/2005 | Marks et al. |
| 2005/0197180 A1 | 9/2005 | Kaminkow et al. |
| 2005/0218591 A1 | 10/2005 | Torigian et al. |
| 2006/0025195 A1 | 2/2006 | Pennington et al. |
| 2006/0030401 A1 | 2/2006 | Mead et al. |
| 2006/0040723 A1 | 2/2006 | Baerlocher et al. |
| 2006/0040732 A1 | 2/2006 | Baerlocher et al. |
| 2006/0040733 A1 | 2/2006 | Baerlocher et al. |
| 2006/0040734 A1 | 2/2006 | Baerlocher et al. |
| 2006/0040736 A1 | 2/2006 | Baerlocher et al. |
| 2006/0046822 A1 | 3/2006 | Kaminkow et al. |
| 2006/0068882 A1 | 3/2006 | Baerlocher et al. |
| 2006/0068893 A1 | 3/2006 | Jaffe et al. |
| 2006/0073874 A1 | 4/2006 | Cregan et al. |
| 2006/0084500 A1 | 4/2006 | Baerlocher et al. |
| 2006/0183528 A1 | 8/2006 | Rodgers et al. |
| 2006/0199628 A1 | 9/2006 | Rodgers et al. |
| 2006/0217189 A1 | 9/2006 | Walker et al. |
| 2006/0246977 A1 | 11/2006 | Cannon |
| 2006/0252518 A1 | 11/2006 | Walker et al. |
| 2007/0015566 A1 | 1/2007 | Baerlocher et al. |
| 2007/0032285 A1 | 2/2007 | Wolf |
| 2007/0054732 A1 | 3/2007 | Baerlocher |
| 2007/0054733 A1 | 3/2007 | Baerlocher |
| 2007/0060271 A1 | 3/2007 | Cregan et al. |
| 2007/0060300 A1 | 3/2007 | Baerlocher |
| 2007/0077990 A1 | 4/2007 | Cuddy et al. |
| 2007/0082725 A1 | 4/2007 | Low et al. |
| 2007/0087809 A1 | 4/2007 | Baerlocher |
| 2007/0105620 A1 | 5/2007 | Cuddy et al. |
| 2007/0111783 A1 | 5/2007 | Cuddy et al. |
| 2007/0117606 A1 | 5/2007 | Baerlocher et al. |
| 2007/0129131 A1 | 6/2007 | Kaminkow et al. |
| 2007/0149269 A1 | 6/2007 | Benbrahim |
| 2007/0155464 A1 | 7/2007 | Baerlocher et al. |
| 2007/0155485 A1 | 7/2007 | Cuddy et al. |
| 2007/0167211 A1 | 7/2007 | Rodgers et al. |
| 2007/0167217 A1 | 7/2007 | Kaminkow et al. |
| 2008/0020817 A1 | 1/2008 | Kaminkow et al. |
| 2008/0020822 A1 | 1/2008 | Cuddy et al. |
| 2008/0020823 A1 | 1/2008 | Cuddy et al. |
| 2008/0020824 A1 | 1/2008 | Cuddy et al. |
| 2008/0020825 A1 | 1/2008 | Cuddy et al. |
| 2008/0020829 A1 | 1/2008 | Baerlocher |
| 2008/0020842 A1 | 1/2008 | Kaminkow et al. |
| 2008/0020847 A1 | 1/2008 | Kniesteadt et al. |
| 2008/0026808 A1 | 1/2008 | Yoshizawa |
| 2008/0026813 A1* | 1/2008 | Cannon ............... 463/18 |
| 2008/0051168 A1 | 2/2008 | Kaminkow et al. |
| 2008/0051188 A1 | 2/2008 | Inamura |
| 2008/0058046 A1 | 3/2008 | Schwartz et al. |
| 2008/0070662 A1 | 3/2008 | Verardi et al. |
| 2008/0070676 A1 | 3/2008 | Baerlocher et al. |
| 2008/0070677 A1 | 3/2008 | Baerlocher et al. |
| 2008/0070678 A1 | 3/2008 | Baerlocher et al. |
| 2008/0070702 A1 | 3/2008 | Kaminkow et al. |
| 2008/0081690 A1 | 4/2008 | Baerlocher et al. |
| 2008/0081691 A1 | 4/2008 | Baerlocher et al. |
| 2008/0090651 A1 | 4/2008 | Baerlocher |
| 2008/0102916 A1 | 5/2008 | Kovacs et al. |
| 2008/0102920 A1 | 5/2008 | Baerlocher |
| 2008/0108401 A1 | 5/2008 | Baerlocher et al. |
| 2008/0108429 A1 | 5/2008 | Davis et al. |
| 2008/0113765 A1 | 5/2008 | DeWaal |
| 2008/0113768 A1 | 5/2008 | Baerlocher |
| 2008/0113771 A1 | 5/2008 | Baerlocher et al. |
| 2008/0139274 A1 | 6/2008 | Baerlocher |
| 2008/0139290 A1 | 6/2008 | Kniesteadt et al. |
| 2008/0149292 A1 | 6/2008 | Scherb |
| 2008/0153564 A1 | 6/2008 | Baerlocher et al. |
| 2008/0176650 A1 | 7/2008 | Wolf et al. |
| 2008/0274788 A1* | 11/2008 | Wilson ............... 463/20 |
| 2009/0042644 A1 | 2/2009 | Zielinski |

FOREIGN PATENT DOCUMENTS

| | | |
|---|---|---|
| EP | 1 199 689 | 4/2002 |
| EP | 1 298 607 | 4/2003 |
| EP | 1 531 434 | 5/2005 |
| EP | 1 764 753 | 3/2007 |
| EP | 1 779 908 | 5/2007 |
| GB | 2 097 160 | 10/1982 |
| GB | 2 113 881 | 8/2003 |
| WO | WO 97/32285 | 9/1997 |
| WO | WO 00/12186 | 3/2000 |
| WO | WO 01/74464 | 10/2001 |
| WO | WO 03/026759 | 4/2003 |
| WO | WO 03/049053 | 6/2003 |
| WO | WO 2005/002697 | 1/2005 |
| WO | WO 2005/015826 | 2/2005 |
| WO | WO 2006/017067 | 2/2006 |
| WO | WO 2007/021724 | 2/2007 |
| WO | WO 2007/052549 | 5/2007 |
| WO | WO 2008/045398 | 4/2008 |
| WO | WO 2008/045464 | 4/2008 |

OTHER PUBLICATIONS

Battleship instructions, Hasbro, published 2002.
Battleship All Aboard, website description, Mikohn, website printed 2001.
Article entitled "Cash Box" in Strictly Slots, published Jul. 2000.
Clue: The Great Museum Caper, Wikipedia description, http://en.wikipedia.org/wiki/Clue:_The_Great_Museum_Caper, website printed on Jan. 29, 2008.
Command & Conquer, Wikipedia description, http://en.wikipedia.org/wiki/Command_and_conquer, website printed Aug. 18, 2008.
Article entitled "Cool Cat Cash" in Strictly Slots, published Jul. 2005.
Article entitled "Crazy Fruits" in Strictly Slots, published Apr. 2001.
Article entitled "Deviled Eggs" in Strictly Slots, published May 2005.
Dig Dug, Wikipedia description, http//en.wikipedia.org/wiki/Dig_Dug, website printed on Jan. 29, 2008.
Dots and Boxes—Game Description from Wikipedia, http://en.wikipedia.org/wiki/Dots_and_Boxes, available prior to Nov. 13, 2008.
Article entitled "Hollywood Squares—Premier Night" in Strictly Slots, published 2005.
Its My Party advertisement, IGT, published 2004.
Jeopardy Video Slots advertisement, IGT, published in 2000.
Loop game, Screen Shot and game description, http://www.shockwavegames.com, available prior to Jun. 2008.
Article entitled "Men in Black" in Strictly Slots, published Apr. 2004.
Microsoft Surface description, http://en.wikipedia.org/wiki/Microsoft_surface, available prior to Nov. 13, 2008.
Minesweeper (computer game), Wikipedia description, http://en.wikipedia.org/wiki/Minesweeper_(compter_game), website printed Jan. 29, 2008.

Radar Mission, Wikipedia description, http://en.wikipedia.org/wiki/Radar_Mission, website printed Aug. 18, 2008.

Stratego, Wikipedia description, http://en.wikipedia.org/wiki/Stratego, website printed on Sep. 3, 2008.

Triple Double Dollars Video Slots advertisement, IGT, published 2004.

* cited by examiner

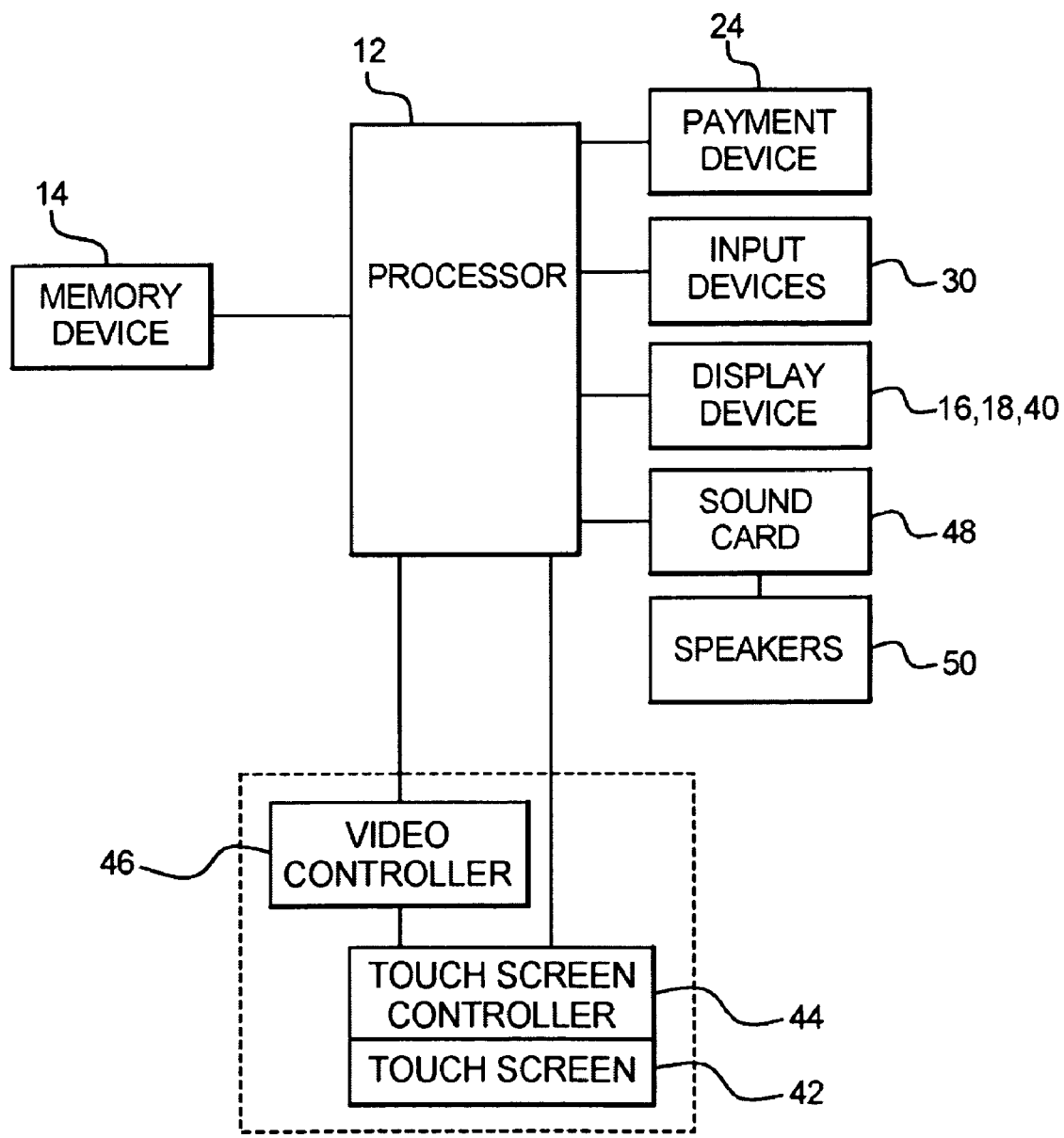

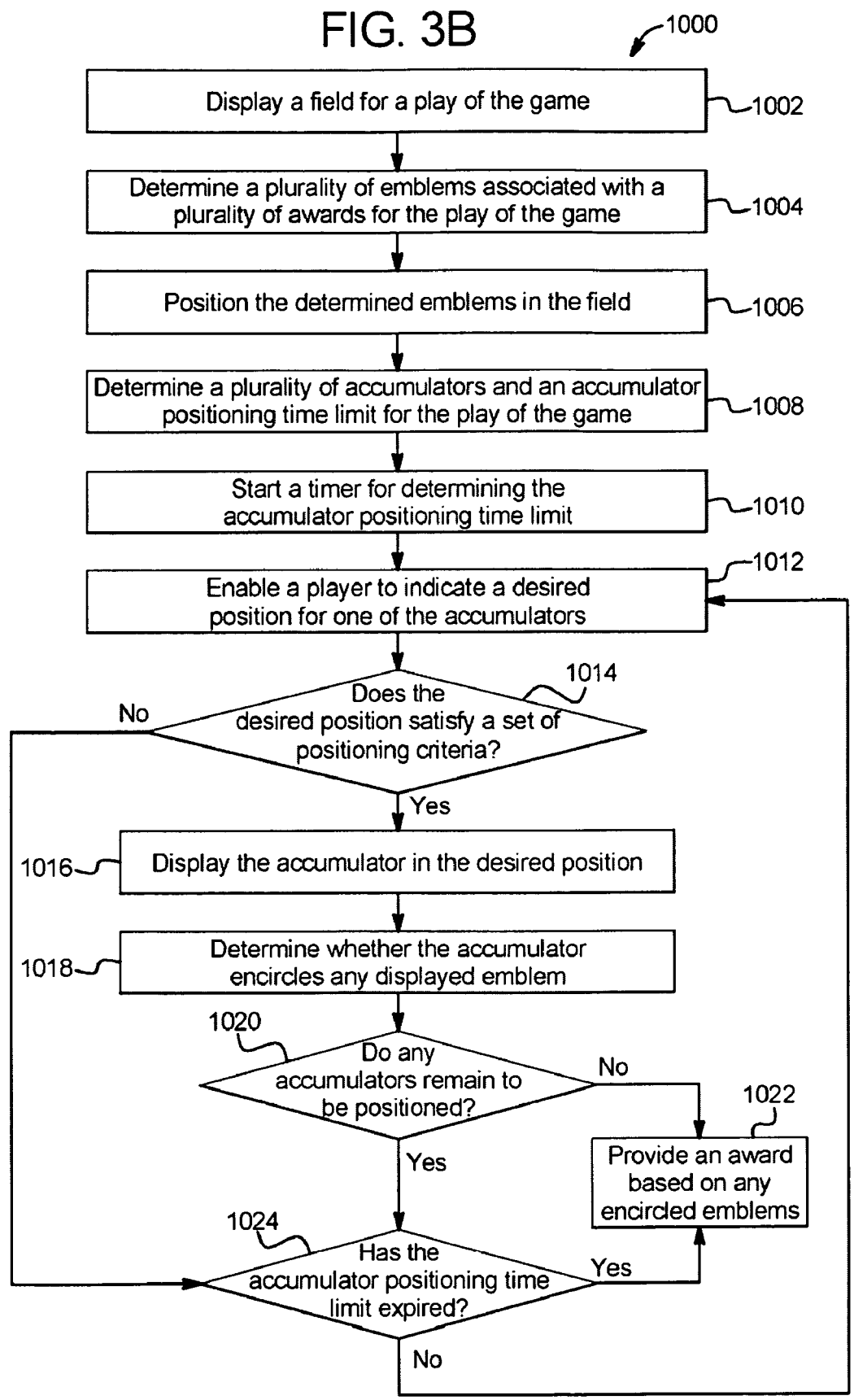

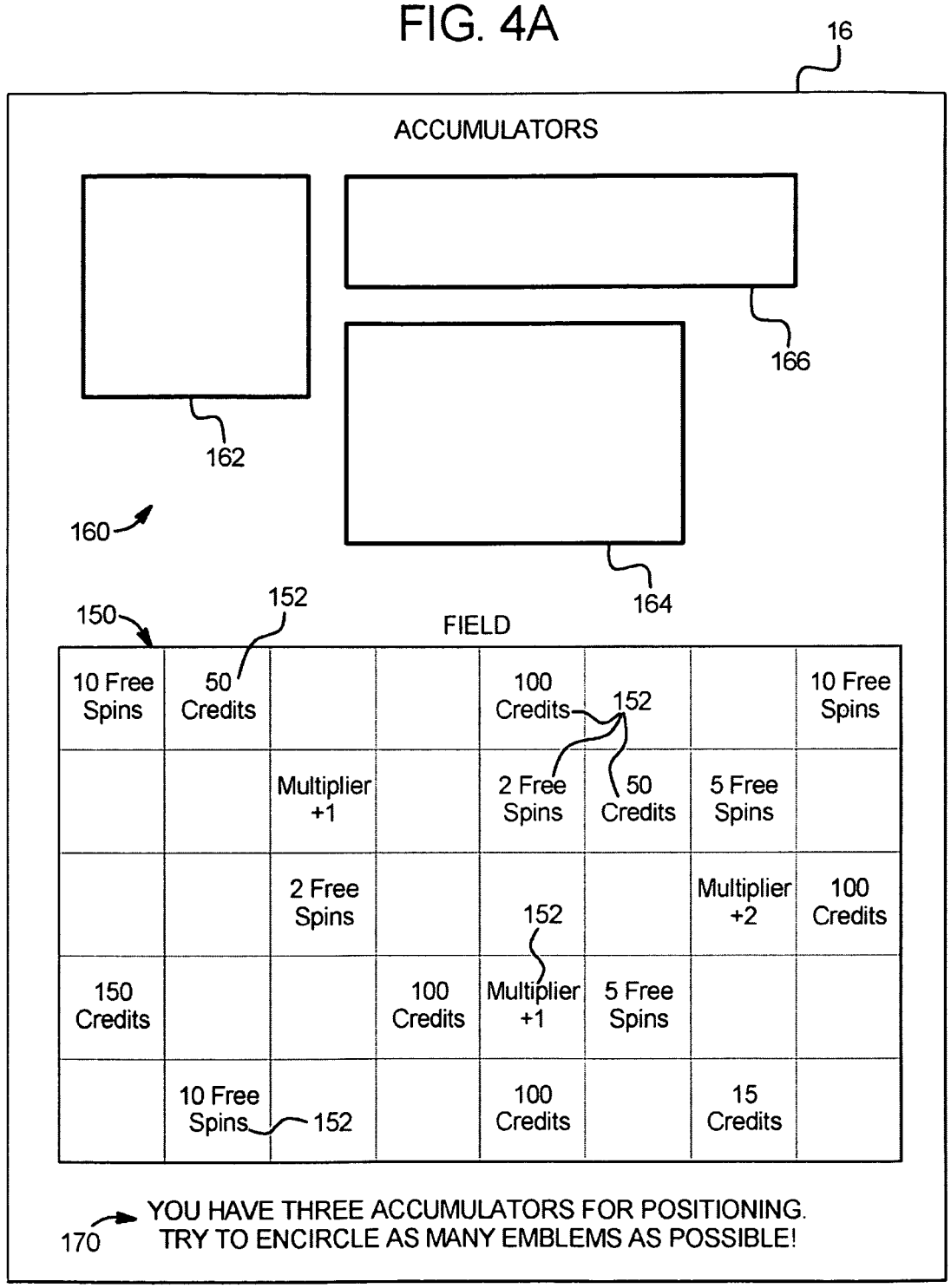

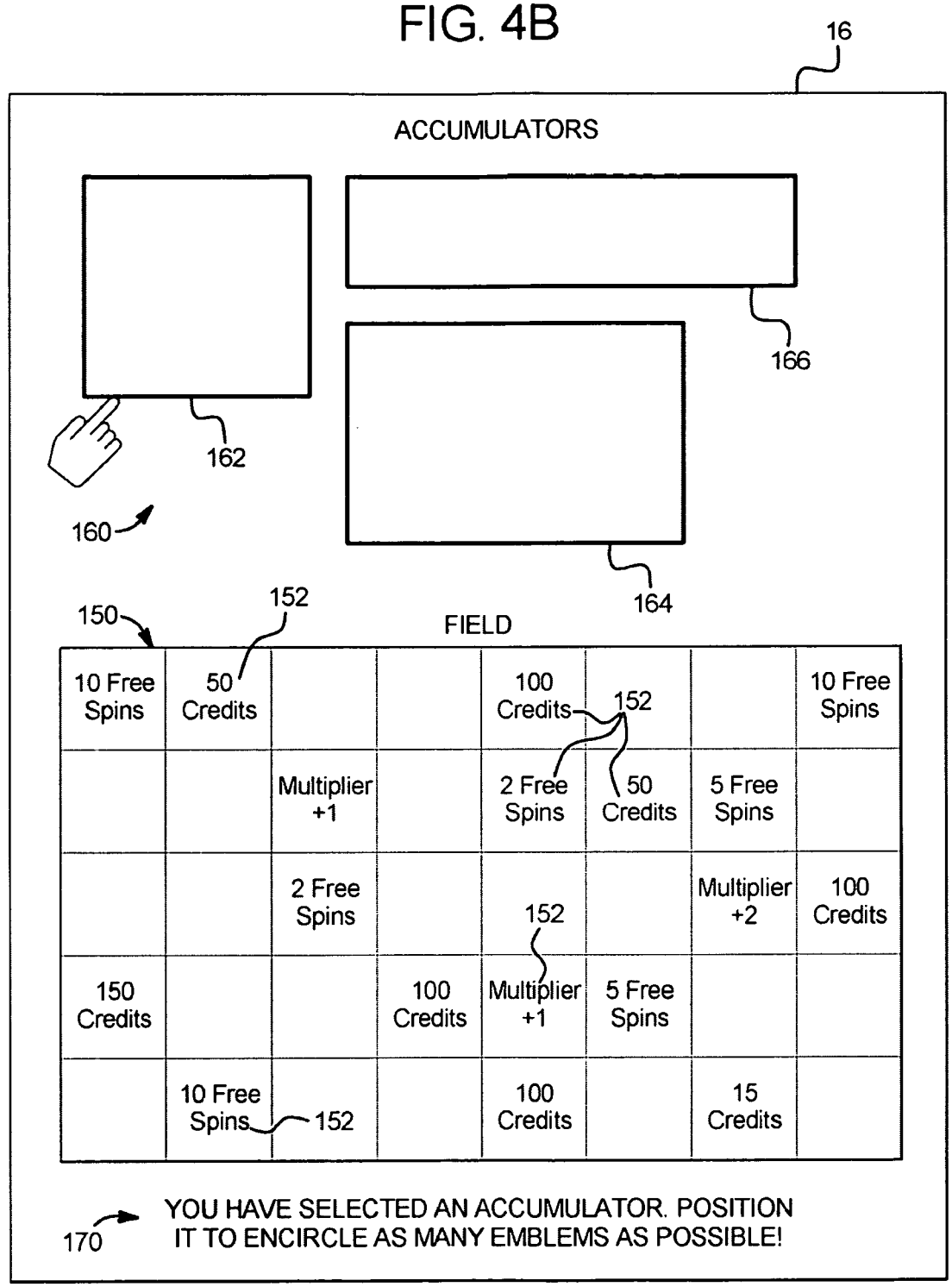

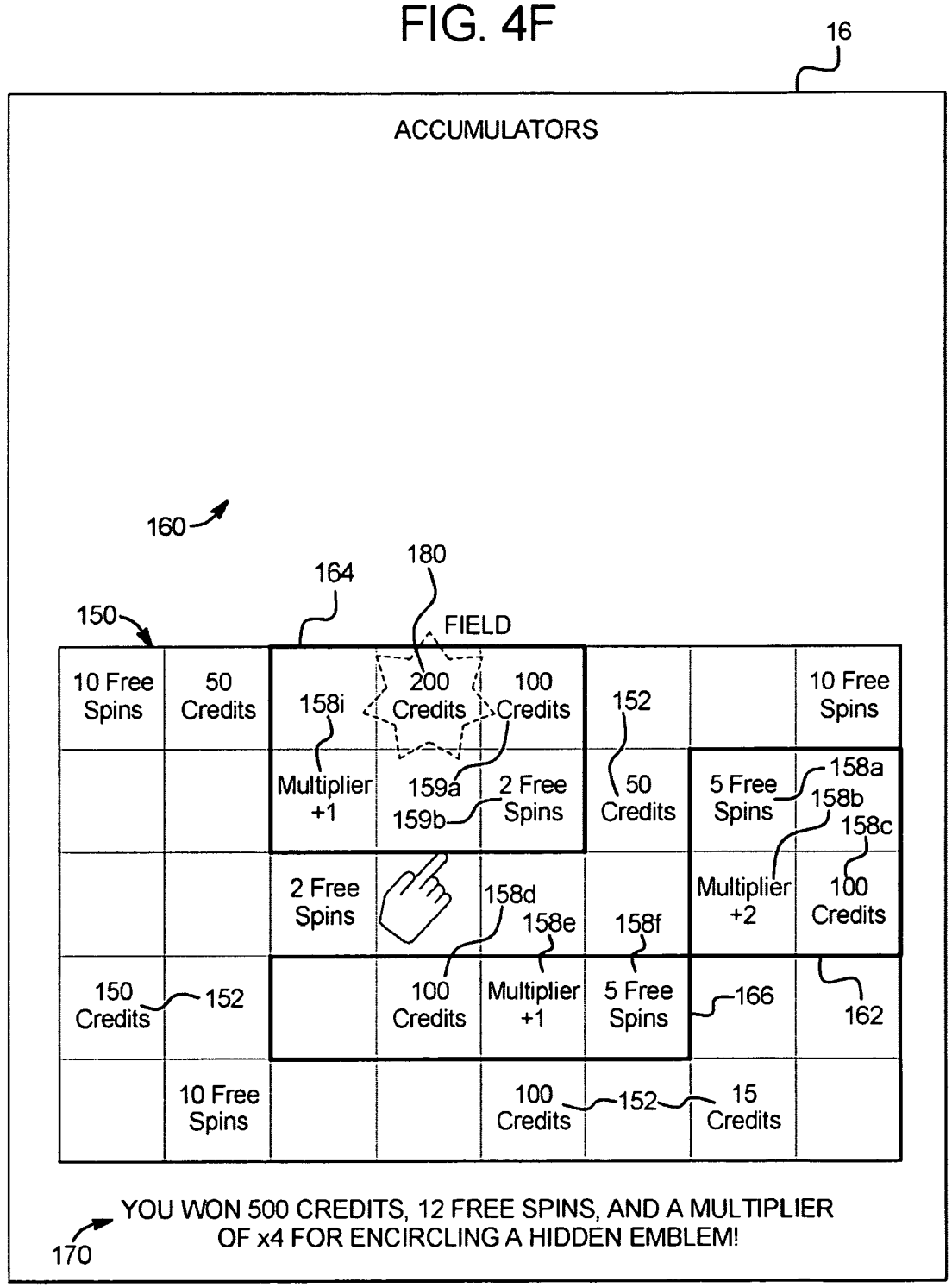

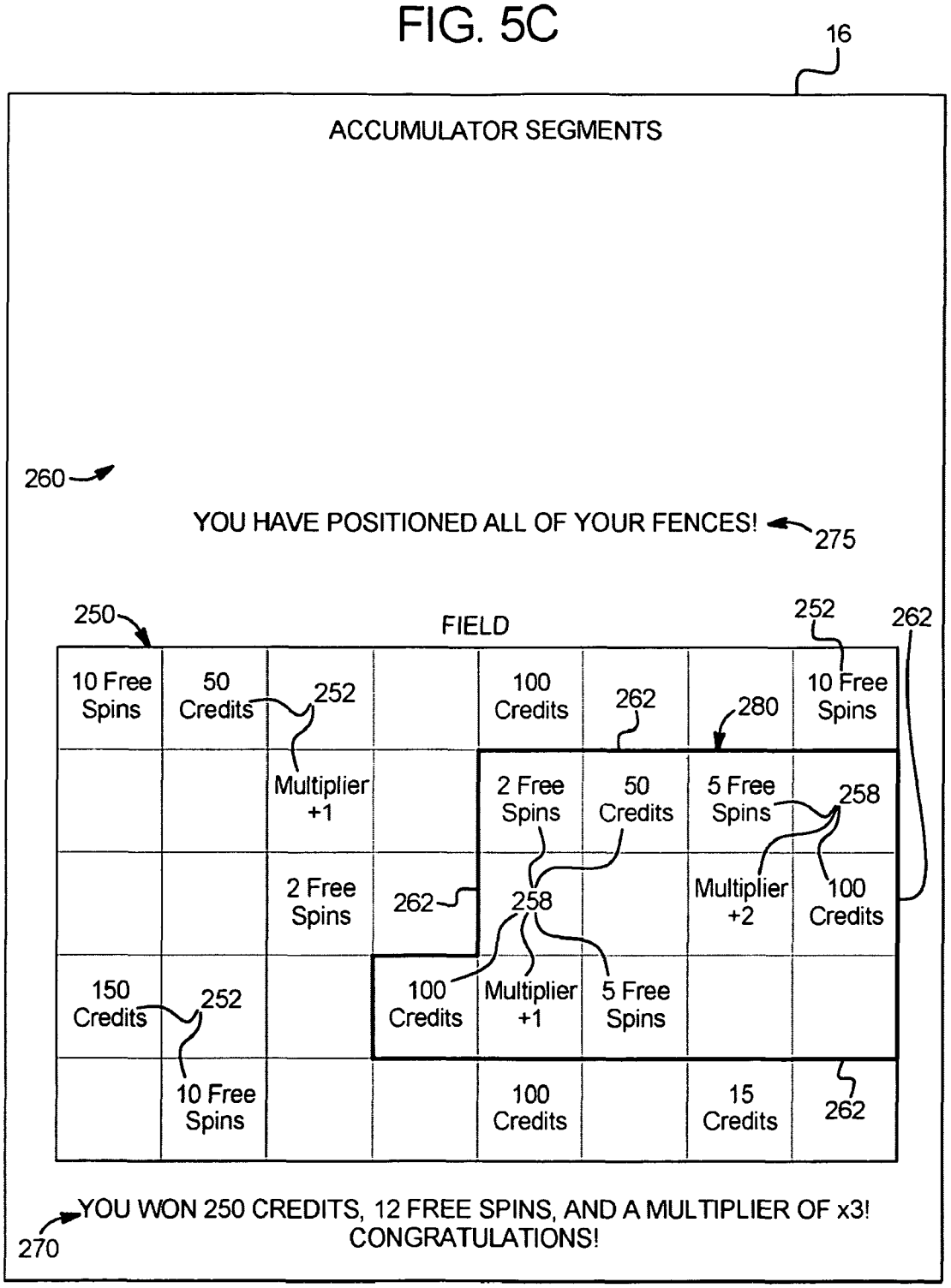

FIG. 5D

ACCUMULATOR SEGMENTS

260 →

YOU HAVE POSITIONED ALL OF YOUR FENCES! ← 275

250 → FIELD

| 10 Free Spins | 50 Credits ↘252 | | 100 Credits | 262 | | 10 Free Spins |
|---|---|---|---|---|---|---|
| | Multiplier +1 | | 2 Free Spins | 50 Credits | 5 Free Spins | |
| 262 | 2 Free Spins | | | 298 ↘ Multiplier +2 | | 100 Credits |
| 1000 Credits ↘298 | | | 100 Credits | Multiplier +1 | 5 Free Spins | 262 |
| | 10 Free Spins ↘262 | | 100 Credits | | 15 Credits | |

270 → YOU WON 1050 CREDITS, 15 FREE SPINS, AND A MULTIPLIER OF x2! CONGRATULATIONS!

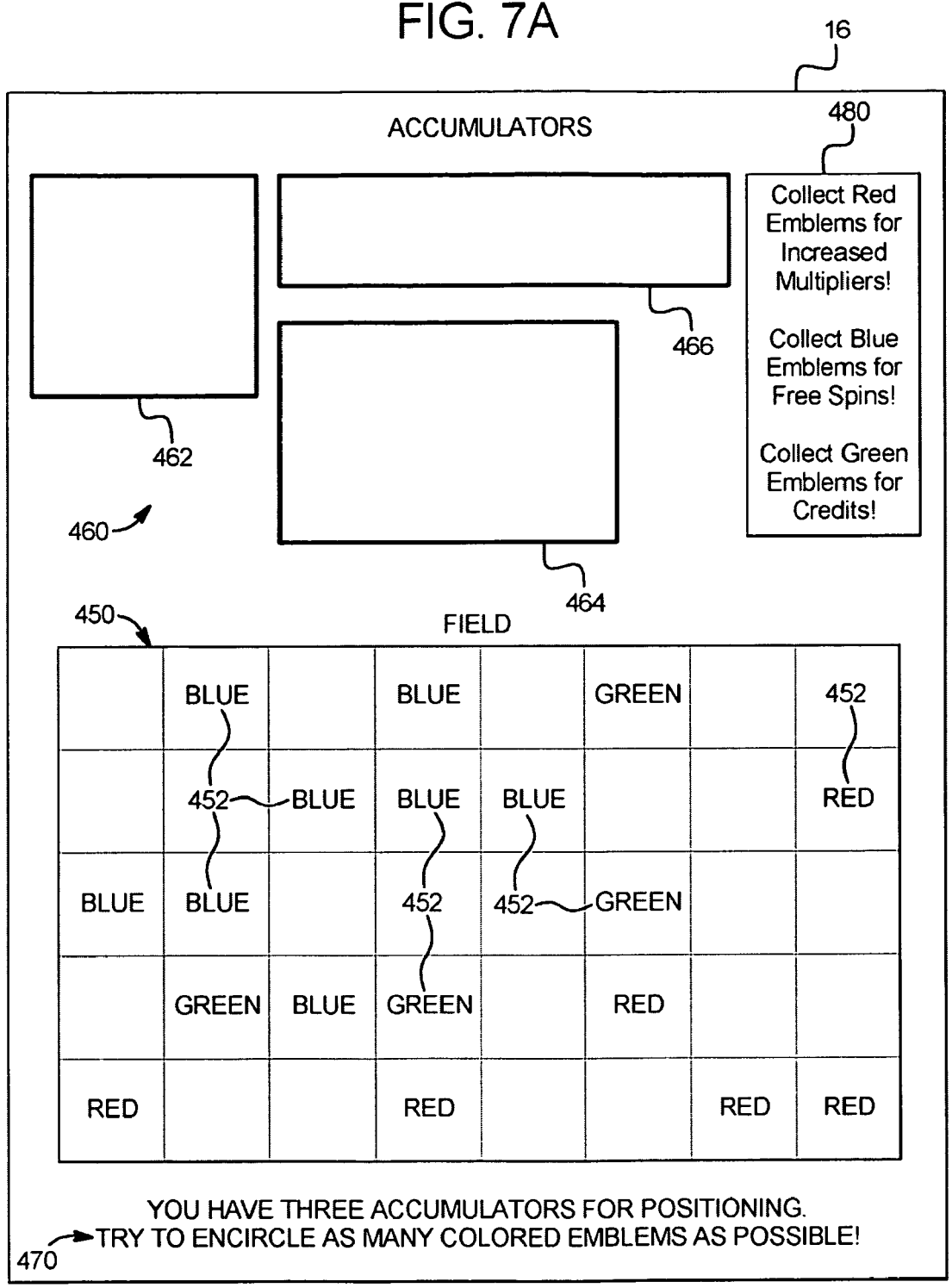

GAMING SYSTEM, GAMING DEVICE, AND METHOD FOR PROVIDING A GAME IN WHICH A PLAYER COLLECTS EMBLEMS BY POSITIONING ACCUMULATORS IN A FIELD

COPYRIGHT NOTICE

A portion of the disclosure of this patent document contains material which is subject to copyright protection. The copyright owner has no objection to the photocopy reproduction of the patent document or the patent disclosure in exactly the form it appears in the Patent and Trademark Office patent file or records, but otherwise reserves all copyright rights whatsoever.

BACKGROUND

Player selection bonus games are popular and well-known in the gaming industry. In certain known selection bonus games, the gaming device displays a plurality of positions to a player, some of which are associated with awards and at least one of which is associated with a terminating symbol. In these types of games, typically the gaming device enables the player to select positions until the player selects a position associated with a terminator, at which time the gaming device provides the player with any earned awards and the bonus ends. In other selection bonus games, the gaming device enables the player to select a certain number of positions. In one known variation, the player may earn additional selection opportunities for the bonus from picking one or more of the selections.

Other known selection games are matching games. These games generally require a player to select displayed positions and generally display the symbol at each selected position. Such selection games typically continue to display the symbols until the player selects two or more matching symbols, at which time the player may be provided with an award. Thus, certain known selection games which provide matching games do not require an element of skill, as the previously selected symbols remain revealed even after selection.

Certain known games are multiple player bonus games which enable a plurality of players to simultaneously interact with the game. Such known multiple player bonus games allow little or no player strategy while playing the games.

Accordingly, a need exists for gaming systems, gaming devices and methods providing new and exciting player selection games to individual players and to multiple players simultaneously which enable players to use skill to determine a bonus award.

SUMMARY

The present disclosure relates generally to gaming systems, gaming devices, and methods for providing a game which enables a player to position one or more accumulators to generate a plurality of awards for the play of the game. More particularly, one embodiment of the gaming system disclosed herein displays a plurality of emblems in a field of emblems for a play of the game. The gaming system enables a player to select a position for each accumulator within the field in an effort to collect the displayed emblems. Based on the position of each accumulator with respect to the emblems in the field, the gaming system provides a plurality of awards to the player for the play of the game.

More specifically, in one embodiment, a gaming system disclosed herein enables a player to play a game which illustrates or defines a field. In this embodiment, the gaming system is configured to display a plurality of emblems in the predefined field for a play of the game. In one embodiment, each of the emblems is stationary during the play of the game (i.e., during the player positioning of the accumulator(s)). In another embodiment, one or more of the emblems moves during the play of the game (i.e., during the player positioning of the accumulator(s)). In various embodiments, at least one of the emblems is associated with an award. It should thus be appreciated that each of the plurality of emblems in certain embodiments each represent a potential award obtainable by a player for a play of the game.

For the play of the game, the gaming system displays at least one and preferably a plurality of positionable accumulators to the player. In certain embodiments, the size and shape of each accumulator is predetermined or randomly determined. In other embodiments, the gaming system enables the player to determine a size, a shape, or both a size and a shape of one or more of the positionable accumulators. In one embodiment, the gaming system enables the player to select a positionable accumulator from among a plurality of positional accumulators of varying sizes and/or shapes. The gaming system enables the player to position each accumulator within the field displayed by the gaming system. The number of accumulators for each play of the game may be determined in any suitable manner.

In one embodiment, the gaming system enables a player to sequentially position a plurality of positionable accumulators for the play of the game without indicating a shape and/or size of a future positionable accumulator. In one embodiment, the gaming system displays only the accumulator to be positioned. In another embodiment, the gaming system displays the accumulator to be positioned and one or more future accumulator to be positioned. In various embodiments, the gaming system continues to display additional positionable accumulators so long as the player can position the currently positionable accumulator. In one embodiment, the gaming system displays additional positionable accumulators so long as the player can position the currently positionable accumulator until a maximum quantity of positionable accumulators has been positioned.

The gaming system includes a plurality of accumulator positioning criteria which define a set of rules governing allowed and prohibited positions of each positionable accumulator for each play of the game. In one embodiment, the gaming system applies the accumulator positioning criteria each time the player indicates a desired position for an accumulator within the field. For example, the gaming system may apply the accumulator positioning criteria to determine whether the indicated position for the accumulator is an allowed position for the play of the game. For example, in one embodiment, the accumulator positioning criteria require the accumulator to be positioned entirely within the field. In one embodiment, the accumulator positioning criteria prohibit the player from positioning a first accumulator and a second accumulator such that the first accumulator overlaps the second accumulator. In one embodiment, the accumulator positioning criteria require the player to indicate a position of an accumulator within a designated amount of time. In one embodiment, the positioning criteria require the player to position one or more positionable accumulators such that they are adjacent to or touching another positioned accumulator in the field. In another embodiment, the gaming system requires the player to position one or more positionable accumulators such that they are not adjacent to or not touching a positioned accumulator in the field.

In one embodiment, the gaming system also determines whether the player-indicated position of each accumulator relative to the displayed emblems causes one or more of the emblems to be collected, captured, corralled, or otherwise won for the play of the game. In this embodiment, if an emblem is collected, the gaming system designates the emblem as a collected or winning emblem. In one such embodiment, the accumulator positioning criteria define a set of spatial relationships between an emblem and an accumulator which cause the emblem to be collected. In one embodiment, the gaming system determines that an emblem is collected if a positioned accumulator encircles the emblem. In another embodiment, the gaming system determines that an emblem is collected if the perimeter of a positioned accumulator touches or abuts the perimeter the emblem. In other embodiments, the gaming system determines that an emblem is collected if is not encircled by or does not abut any of the positioned accumulators.

In one embodiment, the gaming system provides a total award based on any awards associated with any collected emblems. In another embodiment, the gaming system provides an award based on whether the player positioned each accumulator optimally based on the emblems displayed in the field. In other embodiments, each award is based on whether an emblem is in a designated spatial relationship with more than one accumulator, or whether a plurality of emblems are in a designated spatial relationship with a single accumulator.

It should be appreciated that in various embodiments, the accumulator positioning criteria define potential strategies for the player to follow in positioning the accumulators. That is, the accumulator positioning criteria define a goal (e.g., a desired relationship between each accumulator and the plurality of emblems which results in a maximum amount of emblems being collected) and a set of rules which must be followed to attain the goal (e.g., a positioned accumulator may not overlap any other positioned accumulators). The accumulator positioning criteria thus determine whether a player-selected position for each accumulator is a relatively good position or a relatively bad position. The disclosed gaming system therefore enables a player to utilize a strategy in selecting the position of each accumulator, and provides one or more award(s) to the player based on how near the employed strategy is to an optimal strategy.

In one embodiment, the gaming system disclosed herein is a single-player gaming system. In this embodiment, the field of emblems is displayed to a single player, and the gaming system enables the single player to position each of the accumulators within the field. The gaming system then provides an award to the single player based on any emblems collected by the positioned accumulators. It should be appreciated that the gaming system may increase the excitement and enjoyment of the players by requiring the players to position the accumulators within a designated time period.

In another embodiment, the gaming system disclosed herein enables a plurality of players to each position one or more accumulators in a communal predefined field. In this embodiment, the gaming system displays a communal field and displays a plurality of emblems within the communal field, wherein each emblem represents an opportunity for any of the plurality of players to receive an award for a play of the game. In a further embodiment, at least one emblem displayed in the communal field represents an opportunity for more than one of the plurality of players to win an award for a same play of a community game. The gaming system enables each of the players to position one or more accumulators within the communal field. In this embodiment, the gaming system determines, for each positioned accumulator, whether one or more emblems is collected and indicates such collected emblems for the play of the game. The gaming system provides an award to any appropriate players based on their collected emblems. In one such embodiment, the gaming system provides an award to each player who positioned an accumulator which collected an emblem.

In one such embodiment, the gaming system enables a plurality of players to competitively position accumulators in the communal field for a play of the game. In this embodiment, the gaming system provides a designated award which is divisible among the players based on the selected positions of the accumulators. Thus, in this embodiment, players compete with one another in an effort to obtain as much of the designated award as possible. In one embodiment, once a player positions an accumulator such that one or more emblems are collected, the gaming system removes the positioned accumulator and the collected emblems from the field. In another embodiment, the gaming system does not remove one or more of the positioned accumulator and the collected emblems from the field upon collecting the emblems. In one embodiment, the play of the game for the plurality of players ends when each of the displayed emblems has been collected. In another embodiment, one or more emblems regenerates after being collected.

In another such embodiment, the gaming system enables a plurality of players to cooperatively position accumulators in the communal field for a play of the game. In this embodiment, the gaming system provides the players with a common goal, such as collecting each of the emblems as quickly as possible or collecting as many emblems as possible within a specific amount of time. Thus, in this embodiment, players cooperate with one another in an effort to satisfy the common goal as quickly as possible.

In one embodiment, the gaming system disclosed herein is provided as a primary wagering game. In this embodiment, the gaming system enables a player to wager on a play of the game. For the play of the game, the gaming system displays a plurality of emblems and one or more accumulators, and enables the player to position the accumulators according to the accumulator positioning criteria.

In another embodiment, the gaming system disclosed herein is provided as a secondary game. In this embodiment, the gaming system enables the player to wager on a play of a primary game, such as a slot game. Upon the occurrence of an appropriate triggering event in the primary game, the disclosed gaming system displays a plurality of emblems and one or more accumulators for a play of the secondary game. The gaming system in this embodiment provides a secondary or bonus award based on the player-selected positions of the one or more accumulators related to the positions of the displayed emblems.

It should be appreciated that the gaming system disclosed herein provides a game including a plurality of emblems displayed in a predefined field and at least one accumulator configured to be positioned in the predefined field relative to the emblems.

It should be further appreciated that the gaming system disclosed herein enables a player to position each accumulator according to a plurality of accumulator positioning criteria and according to the player's determination as to the "best" position for the accumulator based on the accumulator positioning criteria and to provide awards based on the position of the at least one accumulator.

Additional features and advantages are described in, and will be apparent from, the following Detailed Description and the figures.

BRIEF DESCRIPTION OF THE FIGURES

FIG. 2A is a schematic block diagram of one embodiment of an electronic configuration for one of the gaming devices disclosed herein.

FIG. 3B is a flow chart of an alternative example process for operating the game disclosed herein.

FIGS. 4A, 4B, 4C, 4D, 4E, and 4F are front elevation views a display device of one embodiment of the gaming system disclosed herein.

FIGS. 5A, 5B, 5C, and 5D are font elevation views of a display device of a second embodiment of the gaming system disclosed herein.

FIGS. 7A and 7B are front elevation views of a display device of a fourth embodiment of the gaming system disclosed herein.

DETAILED DESCRIPTION

The present disclosure may be implemented in various configurations for gaming machines, gaming devices, or gaming systems, including but not limited to: (1) a dedicated gaming machine, gaming device, or gaming system wherein the computerized instructions for controlling any games (which are provided by the gaming machine or gaming device) are provided with the gaming machine or gaming device prior to delivery to a gaming establishment; and (2) a changeable gaming machine, gaming device, or gaming system wherein the computerized instructions for controlling any games (which are provided by the gaming machine or gaming device) are downloadable to the gaming machine or gaming device through a data network after the gaming machine or gaming device is in a gaming establishment. In one embodiment, the computerized instructions for controlling any games are executed by at least one central server, central controller, or remote host. In such a "thin client" embodiment, the central server remotely controls any games (or other suitable interfaces) and the gaming device is utilized to display such games (or suitable interfaces) and receive one or more inputs or commands from a player. In another embodiment, the computerized instructions for controlling any games are communicated from the central server, central controller, or remote host to a gaming device local processor and memory devices. In such a "thick client" embodiment, the gaming device local processor executes the communicated computerized instructions to control any games (or other suitable interfaces) provided to a player.

In one embodiment, one or more gaming devices in a gaming system may be thin client gaming devices and one or more gaming devices in the gaming system may be thick client gaming devices. In another embodiment, certain functions of the gaming device are implemented in a thin client environment and certain other functions of the gaming device are implemented in a thick client environment. In one such embodiment, computerized instructions for controlling any primary games are communicated from the central server to the gaming device in a thick client configuration and computerized instructions for controlling any secondary games or bonus functions are executed by a central server in a thin client configuration.

Figure 1A:
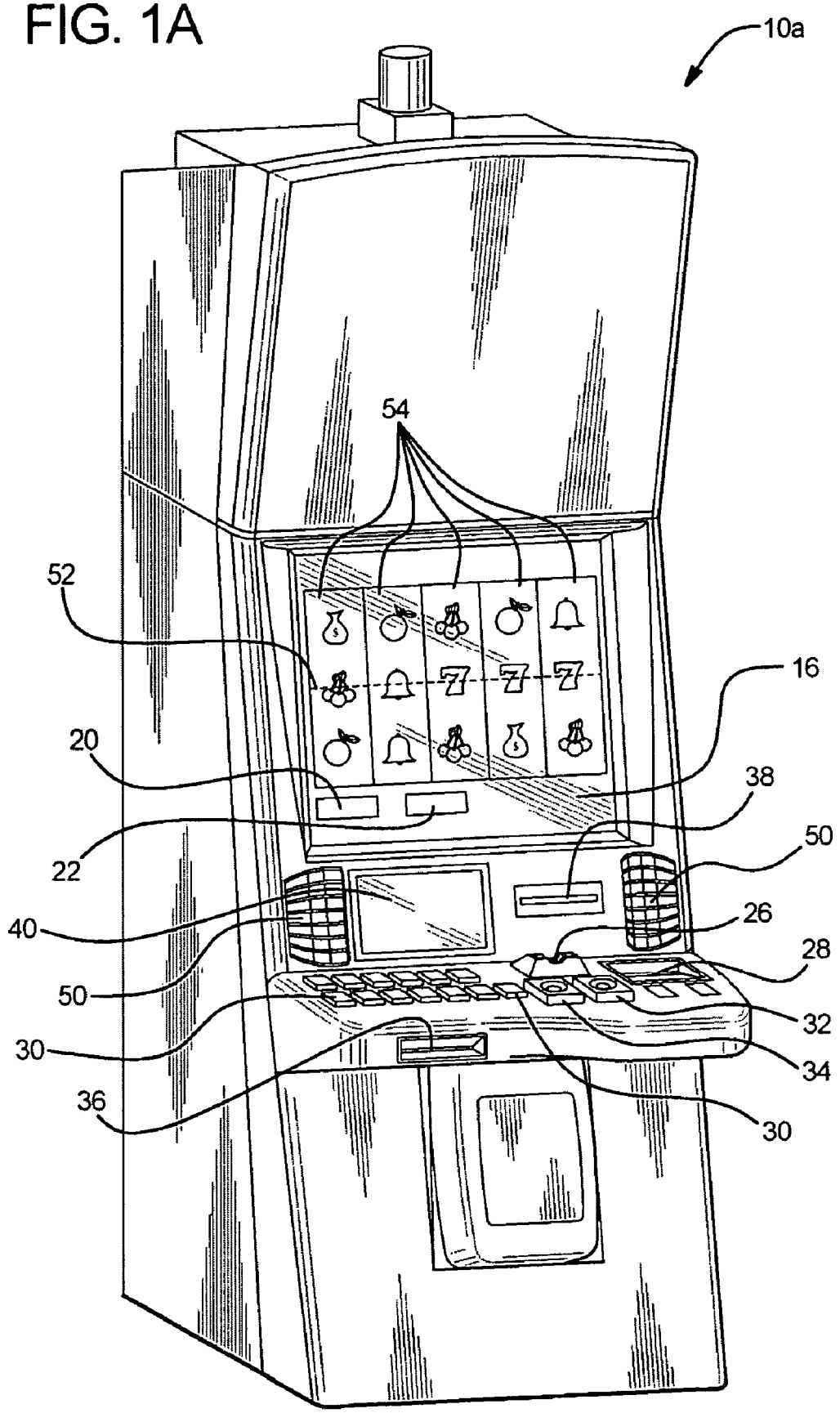
FIGS. 1A and 1B are perspective views of example alternative embodiments of the gaming device of the present disclosure.
Figure 1B:
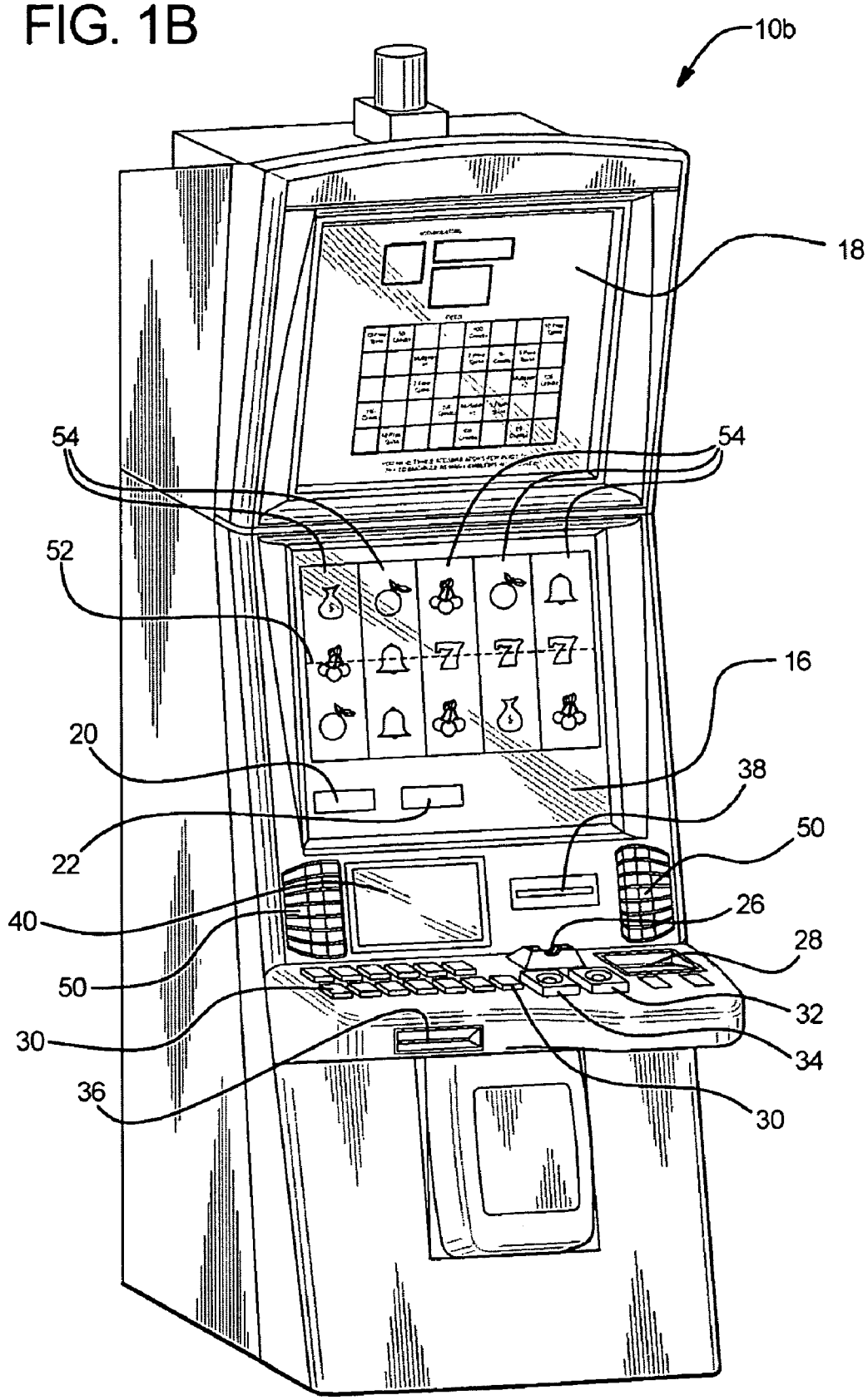

Referring now to the drawings, two example alternative embodiments of a gaming device disclosed herein are illustrated in FIGS. 1A and 1B as gaming device 10a and gaming device 10b, respectively. Gaming device 10a and/or gaming device 10b are generally referred to herein as gaming device 10.

In the embodiments illustrated in FIGS. 1A and 1B, gaming device 10 has a support structure, housing, or cabinet which provides support for a plurality of displays, inputs, controls, and other features of a conventional gaming machine. It is configured so that a player can operate it while standing or sitting. The gaming device can be positioned on a base or stand or can be configured as a pub-style table-top game (not shown) which a player can operate preferably while sitting. As illustrated by the different configurations shown in FIGS. 1A and 1B, the gaming device may have varying cabinet and display configurations.

In one embodiment, as illustrated in FIG. 2A, the gaming device preferably includes at least one processor 12, such as a microprocessor, a microcontroller-based platform, a suitable integrated circuit or one or more application-specific integrated circuits (ASIC's). The processor is in communication with or operable to access or to exchange signals with at least one data storage or memory device 14. In one embodiment, the processor and the memory device reside within the cabinet of the gaming device. The memory device stores program code and instructions, executable by the processor, to control the gaming device. The memory device also stores other data such as image data, event data, player input data, random or pseudo-random number generators, pay-table data or information, and applicable game rules that relate to the play of the gaming device. In one embodiment, the memory device includes random access memory (RAM), which can include non-volatile RAM (NVRAM), magnetic RAM (MRAM), ferroelectric RAM (FeRAM), and other forms as commonly understood in the gaming industry. In one embodiment, the memory device includes read only memory (ROM). In one embodiment, the memory device includes flash memory and/or EEPROM (electrically erasable programmable read only memory). Any other suitable magnetic, optical, and/or semiconductor memory may operate in conjunction with the gaming device disclosed herein.

In one embodiment, part or all of the program code and/or operating data described above can be stored in a detachable or removable memory device, including, but not limited to, a suitable cartridge, disk, CD ROM, DVD, or USB memory device. In other embodiments, part or all of the program code and/or operating data described above can be downloaded to the memory device through a suitable network.

In one embodiment, an operator or a player can use such a removable memory device in a desktop computer, a laptop computer, a personal digital assistant (PDA), a portable computing device, or another computerized platform to implement the present disclosure. In one embodiment, the gaming device or gaming machine disclosed herein is operable over a wireless network, for example part of a wireless gaming system. In this embodiment, the gaming machine may be a hand-held device, a mobile device, or any other suitable wireless device that enables a player to play any suitable game at a variety of different locations. It should be appreciated that a gaming device or gaming machine as disclosed herein may be a device that has obtained approval from a regulatory gaming commission or a device that has not obtained approval from a regulatory gaming commission. It should be appreciated that the processor and memory device may be collectively referred to herein as a "computer" or "controller."

In one embodiment, as discussed in more detail below, the gaming device randomly generates awards and/or other game outcomes based on probability data. In one such embodiment, this random determination is provided through utilization of a random number generator (RNG), such as a true random number generator, a pseudo random number generator, or other suitable randomization process. In one embodiment, each award or other game outcome is associated with a probability and the gaming device generates the award or other game outcome to be provided to the player based on the associated probabilities. In this embodiment, since the gaming device generates outcomes randomly or based upon one or more probability calculations, there is no certainty that the gaming device will ever provide the player with any specific award or other game outcome.

In another embodiment, as discussed in more detail below, the gaming device employs a predetermined or finite set or pool of awards or other game outcomes. In this embodiment, as each award or other game outcome is provided to the player, the gaming device flags or removes the provided award or other game outcome from the predetermined set or pool. Once flagged or removed from the set or pool, the specific provided award or other game outcome from that specific pool cannot be provided to the player again. This type of gaming device provides players with all of the available awards or other game outcomes over the course of the play cycle and guarantees the amount of actual wins and losses.

In another embodiment, as discussed below, upon a player initiating game play at the gaming device, the gaming device enrolls in a bingo game. In this embodiment, a bingo server calls the bingo balls that result in a specific bingo game outcome. The resultant game outcome is communicated to the individual gaming device to be provided to a player. In one embodiment, this bingo outcome is displayed to the player as a bingo game and/or in any form in accordance with the present disclosure.

In one embodiment, as illustrated in FIG. 2A, the gaming device includes one or more display devices controlled by the processor. The display devices are preferably connected to or mounted on the cabinet of the gaming device. The embodiment shown in FIG. 1A includes a central display device 16 which displays a primary game. This display device may also display any suitable secondary game associated with the primary game as well as information relating to the primary or secondary game. The alternative embodiment shown in FIG. 1B includes a central display device 16 and an upper display device 18. The upper display device may display the primary game, any suitable secondary game associated or not associated with the primary game and/or information relating to the primary or secondary game. These display devices may also serve as digital glass operable to advertise games or other aspects of the gaming establishment. As seen in FIGS. 1A and 1B, in one embodiment, the gaming device includes a credit display 20 which displays a player's current number of credits, cash, account balance, or the equivalent. In one embodiment, the gaming device includes a bet display 22 which displays a player's amount wagered. In one embodiment, as described in more detail below, the gaming device includes a player tracking display 40 which displays information regarding a player's play tracking status.

In another embodiment, at least one display device may be a mobile display device, such as a PDA or tablet PC, that enables play of at least a portion of the primary or secondary game at a location remote from the gaming device.

The display devices may include, without limitation, a monitor, a television display, a plasma display, a liquid crystal display (LCD) a display based on light emitting diodes (LEDs), a display based on a plurality of organic light-emitting diodes (OLEDs), a display based on polymer light-emitting diodes (PLEDs), a display based on a plurality of surface-conduction electron-emitters (SEDs), a display including a projected and/or reflected image, or any other suitable electronic device or display mechanism. In one embodiment, as described in more detail below, the display device includes a touch-screen with an associated touch-screen controller. The display devices may be of any suitable size and configuration, such as a square, a rectangle or an elongated rectangle.

The display devices of the gaming device are configured to display at least one and preferably a plurality of game or other suitable images, symbols and indicia such as any visual representation or exhibition of the movement of objects such as mechanical, virtual, or video reels and wheels, dynamic lighting, video images, images of people, characters, places, things, faces of cards, and the like.

In one alternative embodiment, the symbols, images and indicia displayed on or of the display device may be in mechanical form. That is, the display device may include any electromechanical device, such as one or more mechanical objects, such as one or more rotatable wheels, reels, or dice, configured to display at least one or a plurality of game or other suitable images, symbols or indicia.

As illustrated in FIG. 2A, in one embodiment, the gaming device includes at least one payment device 24 in communication with the processor. As seen in FIGS. 1A and 1B, a payment device such as a payment acceptor includes a note, ticket or bill acceptor 28 wherein the player inserts paper money, a ticket, or voucher and a coin slot 26 where the player inserts money, coins, or tokens. In other embodiments, payment devices such as readers or validators for credit cards, debit cards or credit slips may accept payment. In one embodiment, a player may insert an identification card into a card reader of the gaming device. In one embodiment, the identification card is a smart card having a programmed microchip, a coded magnetic strip or coded rewritable magnetic strip, wherein the programmed microchip or magnetic strips are coded with a player's identification, credit totals (or related data), and/or other relevant information. In another embodiment, a player may carry a portable device, such as a cell phone, a radio frequency identification tag, or any other suitable wireless device, which communicates a player's identification, credit totals (or related data), and other relevant information to the gaming device. In one embodiment, money may be transferred to a gaming device through electronic funds transfer. When a player funds the gaming device, the processor determines the amount of funds entered and displays the corresponding amount on the credit or other suitable display as described above.

As seen in FIGS. 1A, 1B, and 2A, in one embodiment the gaming device includes at least one and preferably a plurality of input devices 30 in communication with the processor. The input devices can include any suitable device which enables the player to produce an input signal which is received by the processor. In one embodiment, after appropriate funding of the gaming device, the input device is a game activation device, such as a play button 32 or a pull arm (not shown) which is used by the player to start any primary game or sequence of events in the gaming device. The play button can be any suitable play activator such as a bet one button, a max bet button, or a repeat the bet button. In one embodiment, upon appropriate funding, the gaming device begins the game play automatically. In another embodiment, upon the player engaging one of the play buttons, the gaming device automatically activates game play.

In one embodiment, one input device is a bet one button. The player places a bet by pushing the bet one button. The player can increase the bet by one credit each time the player pushes the bet one button. When the player pushes the bet one button, the number of credits shown in the credit display preferably decreases by one, and the number of credits shown in the bet display preferably increases by one. In another embodiment, one input device is a bet max button (not shown) which enables the player to bet the maximum wager permitted for a game of the gaming device.

In one embodiment, one input device is a cash out button 34. The player may push the cash out button and cash out to receive a cash payment or other suitable form of payment corresponding to the number of remaining credits. In one embodiment, when the player cashes out, a payment device, such as a ticket, payment, or note generator 36 prints or otherwise generates a ticket or credit slip to provide to the player. The player receives the ticket or credit slip and may redeem the value associated with the ticket or credit slip via a cashier (or other suitable redemption system). In another embodiment, when the player cashes out, the player receives the coins or tokens in a coin payout tray. It should be appreciated that any suitable payout mechanisms, such as funding to the player's electronically recordable identification card or smart card, may be implemented in accordance with the gaming device disclosed herein.

In one embodiment, as mentioned above and as seen in FIG. 2A, one input device is a touch-screen 42 coupled with a touch-screen controller 44 or some other touch-sensitive display overlay to allow for player interaction with the images on the display. The touch-screen and the touch-screen controller are connected to a video controller 46. A player can make decisions and input signals into the gaming device by touching the touch-screen at the appropriate locations. One such input device is a conventional touch-screen button panel.

The gaming device may further include a plurality of communication ports for enabling communication of the processor with external peripherals, such as external video sources, expansion buses, game or other displays, a SCSI port, or a keypad.

In one embodiment, as seen in FIG. 2A, the gaming device includes a sound generating device controlled by one or more sounds cards 48 which function in conjunction with the processor. In one embodiment, the sound generating device includes at least one and preferably a plurality of speakers 50 or other sound generating hardware and/or software for generating sounds, such as by playing music for the primary and/or secondary game or by playing music for other modes of the gaming device, such as an attract mode. In one embodiment, the gaming device provides dynamic sounds coupled with attractive multimedia images displayed on one or more of the display devices to provide an audio-visual representation or to otherwise display full-motion video with sound to attract players to the gaming device. During idle periods, the gaming device may display a sequence of audio and/or visual attraction messages to attract potential players to the gaming device. The videos may also be customized to provide any appropriate information.

In one embodiment, the gaming machine may include a sensor, such as a camera, in communication with the processor (and possibly controlled by the processor), that is selectively positioned to acquire an image of a player actively using the gaming device and/or the surrounding area of the gaming device. In one embodiment, the camera may be configured to selectively acquire still or moving (e.g., video) images and may be configured to acquire the images in an analog, digital, or other suitable format. The display devices may be configured to display the image acquired by the camera as well as to display the visible manifestation of the game in split screen or picture-in-picture fashion. For example, the camera may acquire an image of the player and the processor may incorporate that image into the primary and/or secondary game as a game image, symbol or indicia.

Gaming device 10 can incorporate any suitable wagering game as the primary or base game. The gaming machine or device may include some or all of the features of conventional gaming machines or devices. The primary or base game may comprise any suitable reel-type game, card game, cascading or falling symbol game, number game, or other game of chance susceptible to representation in an electronic or electromechanical form, which in one embodiment produces a random outcome based on probability data at the time of or after placement of a wager. That is, different primary wagering games, such as video poker games, video blackjack games, video keno, video bingo or any other suitable primary or base game may be implemented.

In one embodiment, as illustrated in FIGS. 1A and 1B, a base or primary game may be a slot game with one or more paylines 52. The paylines may be horizontal, vertical, circular, diagonal, angled or any combination thereof. In this embodiment, the gaming device includes at least one and preferably a plurality of reels 54, such as three to five reels 54, in either electromechanical form with mechanical rotating reels or video form with simulated reels and movement thereof. In one embodiment, an electromechanical slot machine includes a plurality of adjacent, rotatable reels which may be combined and operably coupled with an electronic display of any suitable type. In another embodiment, if the reels 54 are in video form, one or more of the display devices, as described above, displays the plurality of simulated video reels 54. Each reel 54 displays a plurality of indicia or symbols, such as bells, hearts, fruits, numbers, letters, bars, or other images which preferably correspond to a theme associated with the gaming device. In another embodiment, one or more of the reels are independent reels or unisymbol reels. In this embodiment, each independent or unisymbol reel generates and displays one symbol to the player. In one embodiment, the gaming device awards prizes after the reels of the primary game stop spinning if specified types and/or configurations of indicia or symbols occur on an active payline or otherwise occur in a winning pattern, occur on the requisite number of adjacent reels and/or occur in a scatter pay arrangement.

In an alternative embodiment, rather than determining any outcome to provide to the player by analyzing the symbols generated on any wagered upon paylines as described above, the gaming device determines any outcome to provide to the player based on the number of associated symbols which are generated in active symbol positions on the requisite number of adjacent reels (i.e., not on paylines passing through any displayed winning symbol combinations). In this embodiment, if a winning symbol combination is generated on the reels, the gaming device provides the player one award for that occurrence of the generated winning symbol combination. For example, if one winning symbol combination is generated on the reels, the gaming device will provide a single award to the player for that winning symbol combination (i.e., not based on the number of paylines that would have passed through that winning symbol combination). It should be appreciated that because a gaming device that enables wagering on ways to win provides the player one award for a single occurrence of a winning symbol combination and a gaming device with paylines may provide the player more than one award for the same occurrence of a single winning symbol combination (i.e., if a plurality of paylines each pass through the same winning symbol combination), it is possible to provide a player at a ways to win gaming device with more ways to win for an equivalent bet or wager on a traditional slot gaming device with paylines.

In one embodiment, the total number of ways to win is determined by multiplying the number of symbols generated in active symbol positions on a first reel by the number of symbols generated in active symbol positions on a second reel by the number of symbols generated in active symbol positions on a third reel and so on for each reel of the gaming device with at least one symbol generated in an active symbol position. For example, a three reel gaming device with three symbols generated in active symbol positions on each reel includes 27 ways to win (i.e., 3 symbols on the first reel×3 symbols on the second reel×3 symbols on the third reel). A four reel gaming device with three symbols generated in active symbol positions on each reel includes 81 ways to win (i.e., 3 symbols on the first reel×3 symbols on the second reel×3 symbols on the third reel×3 symbols on the fourth reel). A five reel gaming device with three symbols generated in active symbol positions on each reel includes 243 ways to win (i.e., 3 symbols on the first reel×3 symbols on the second reel×3 symbols on the third reel×3 symbols on the fourth reel×3 symbols on the fifth reel). It should be appreciated that modifying the number of generated symbols by either modifying the number of reels or modifying the number of symbols generated in active symbol positions by one or more of the reels modifies the number of ways to win.

In another embodiment, the gaming device enables a player to wager on and thus activate symbol positions. In one such embodiment, the symbol positions are on the reels. In this embodiment, if based on the player's wager, a reel is activated, then each of the symbol positions of that reel will be activated and each of the active symbol positions will be part of one or more of the ways to win. In one embodiment, if based on the player's wager, a reel is not activated, then a designated number of default symbol positions, such as a single symbol position of the middle row of the reel, will be activated and the default symbol position(s) will be part of one or more of the ways to win. This type of gaming machine enables a player to wager on one, more than one or all of the reels and the processor of the gaming device uses the number of wagered on reels to determine the active symbol positions and the number of possible ways to win. In alternative embodiments, (1) no symbols are displayed as generated at any of the inactive symbol positions, or (2) any symbols generated at any inactive symbol positions may be displayed to the player but suitably shaded or otherwise designated as inactive.

In one embodiment wherein a player wagers on one or more reels, a player's wager of one credit may activate each of the three symbol positions on a first reel, wherein one default symbol position is activated on each of the remaining four reels. In this example, as described above, the gaming device provides the player three ways to win (i.e., 3 symbols on the first reel×1 symbol on the second reel×1 symbol on the third reel×1 symbol on the fourth reel×1 symbol on the fifth reel). In another example, a player's wager of nine credits may activate each of the three symbol positions on a first reel, each of the three symbol positions on a second reel and each of the three symbol positions on a third reel wherein one default symbol position is activated on each of the remaining two reels. In this example, as described above, the gaming device provides the player twenty-seven ways to win (i.e., 3 symbols on the first reel×3 symbols on the second reel×3 symbols on the third reel×1 symbol on the fourth reel×1 symbol on the fifth reel).

In one embodiment, to determine any award(s) to provide to the player based on the generated symbols, the gaming device individually determines if a symbol generated in an active symbol position on a first reel forms part of a winning symbol combination with or is otherwise suitably related to a symbol generated in an active symbol position on a second reel. In this embodiment, the gaming device classifies each pair of symbols which form part of a winning symbol combination (i.e., each pair of related symbols) as a string of related symbols. For example, if active symbol positions include a first cherry symbol generated in the top row of a first reel and a second cherry symbol generated in the bottom row of a second reel, the gaming device classifies the two cherry symbols as a string of related symbols because the two cherry symbols form part of a winning symbol combination.

After determining if any strings of related symbols are formed between the symbols on the first reel and the symbols on the second reel, the gaming device determines if any of the symbols from the next adjacent reel should be added to any of the formed strings of related symbols. In this embodiment, for a first of the classified strings of related symbols, the gaming device determines if any of the symbols generated by the next adjacent reel form part of a winning symbol combination or are otherwise related to the symbols of the first string of related symbols. If the gaming device determines that a symbol generated on the next adjacent reel is related to the symbols of the first string of related symbols, that symbol is subsequently added to the first string of related symbols. For example, if the first string of related symbols is the string of related cherry symbols and a related cherry symbol is generated in the middle row of the third reel, the gaming device adds the related cherry symbol generated on the third reel to the previously classified string of cherry symbols.

On the other hand, if the gaming device determines that no symbols generated on the next adjacent reel are related to the symbols of the first string of related symbols, the gaming device marks or flags such string of related symbols as complete. For example, if the first string of related symbols is the string of related cherry symbols and none of the symbols of the third reel are related to the cherry symbols of the previously classified string of cherry symbols, the gaming device marks or flags the string of two cherry symbols as complete.

After either adding a related symbol to the first string of related symbols or marking the first string of related symbols as complete, the gaming device proceeds as described above for each of the remaining classified strings of related symbols which were previously classified or formed from related symbols on the first and second reels.

After analyzing each of the remaining strings of related symbols, the gaming device determines, for each remaining pending or incomplete string of related symbols, if any of the symbols from the next adjacent reel, if any, should be added to any of the previously classified strings of related symbols. This process continues until either each string of related symbols is complete or there are no more adjacent reels of symbols to analyze. In this embodiment, where there are no more adjacent reels of symbols to analyze, the gaming device marks each of the remaining pending strings of related symbols as complete.

When each of the strings of related symbols is marked complete, the gaming device compares each of the strings of related symbols to an appropriate paytable and provides the player any award associated with each of the completed strings of symbols. It should be appreciated that the player is provided one award, if any, for each string of related symbols generated in active symbol positions (i.e., as opposed to a quantity of awards being based on how many paylines that would have passed through each of the strings of related symbols in active symbol positions).

In one embodiment, a base or primary game may be a poker game wherein the gaming device enables the player to play a conventional game of video draw poker and initially deals five cards all face up from a virtual deck of fifty-two cards. Cards may be dealt as in a traditional game of cards or in the case of the gaming device, the cards may be randomly selected from a predetermined number of cards. If the player wishes to draw, the player selects the cards to hold via one or more input devices, such as by pressing related hold buttons or via the touch screen. The player then presses the deal button and the unwanted or discarded cards are removed from the display and the gaming machine deals the replacement cards from the remaining cards in the deck. This results in a final five-card hand. The gaming device compares the final five-card hand to a payout table which utilizes conventional poker hand rankings to determine the winning hands. The gaming device provides the player with an award based on a winning hand and the number of credits the player wagered.

In another embodiment, the base or primary game may be a multi-hand version of video poker. In this embodiment, the gaming device deals the player at least two hands of cards. In one such embodiment, the cards are the same cards. In one embodiment each hand of cards is associated with its own deck of cards. The player chooses the cards to hold in a primary hand. The held cards in the primary hand are also held in the other hands of cards. The remaining non-held cards are removed from each hand displayed and for each hand replacement cards are randomly dealt into that hand. Since the replacement cards are randomly dealt independently for each hand, the replacement cards for each hand will usually be different. The poker hand rankings are then determined hand by hand against a payout table and awards are provided to the player.

In one embodiment, a base or primary game may be a keno game wherein the gaming device displays a plurality of selectable indicia or numbers on at least one of the display devices. In this embodiment, the player selects at least one bit potentially a plurality of the selectable indicia or numbers via an input device such as a touch screen. The gaming device then displays a series of drawn numbers and determine an amount of matches, if any, between the player's selected numbers and the gaming device's drawn numbers. The player is provided an award based on the amount of matches, if any, based on the amount of determined matches and the number of numbers drawn.

In one embodiment, in addition to winning credits or other awards in a base or primary game, the gaming device may also give players the opportunity to win credits in a bonus or secondary game or in a bonus or secondary round. The bonus or secondary game enables the player to obtain a prize or payout in addition to the prize or payout, if any, obtained from the base or primary game. In general, a bonus or secondary game produces a significantly higher level of player excitement than the base or primary game because it provides a greater expectation of winning than the base or primary game, and is accompanied with more attractive or unusual features than the base or primary game. In one embodiment, the bonus or secondary game may be any type of suitable game, either similar to or completely different from the base or primary game.

In one embodiment, the triggering event or qualifying condition may be a selected outcome in the primary game or a particular arrangement of one or more indicia on a display device in the primary game, such as the number seven appearing on three adjacent reels along a payline in the primary slot game embodiment seen in FIGS. 1A and 1B. In other embodiments, the triggering event or qualifying condition occurs based on exceeding a certain amount of game play (such as number of games, number of credits, amount of time), or reaching a specified number of points earned during game play.

In another embodiment, the gaming device processor 12 or central controller 56 randomly provides the player one or more plays of one or more secondary games. In one such embodiment, the gaming device does not provide any apparent reason to the player for qualifying to play a secondary or bonus game. In this embodiment, qualifying for a bonus game is not triggered by an event in or based specifically on any of the plays of any primary game. That is, the gaming device may simply qualify a player to play a secondary game without any explanation or alternatively with simple explanations. In another embodiment, the gaming device (or central server) qualifies a player for a secondary game at least partially based on a game triggered or symbol triggered event, such as at least partially based on the play of a primary game.

In one embodiment, the gaming device includes a program which will automatically begin a bonus round after the player has achieved a triggering event or qualifying condition in the base or primary game. In another embodiment, after a player has qualified for a bonus game, the player may subsequently enhance his/her bonus game participation through continued play on the base or primary game. Thus, for each bonus qualifying event, such as a bonus symbol, that the player obtains, a given number of bonus game wagering points or credits may be accumulated in a "bonus meter" programmed to accrue the bonus wagering credits or entries toward eventual participation in a bonus game. The occurrence of multiple such bonus qualifying events in the primary game may result in an arithmetic or exponential increase in the number of bonus wagering credits awarded. In one embodiment, the player may redeem extra bonus wagering credits during the bonus game to extend play of the bonus game.

In one embodiment, no separate entry fee or buy-in for a bonus game is needed. That is, a player may not purchase entry into a bonus game; rather they must win or earn entry through play of the primary game, thus encouraging play of the primary game. In another embodiment, qualification of the bonus or secondary game is accomplished through a simple "buy-in" by the player—for example, if the player has been unsuccessful at qualifying through other specified activities. In another embodiment, the player must make a separate side-wager on the bonus game or wager a designated amount in the primary game to qualify for the secondary game. In this embodiment, the secondary game triggering event must occur and the side-wager (or designated primary game wager amount) must have been placed to trigger the secondary game.

Figure 2B:
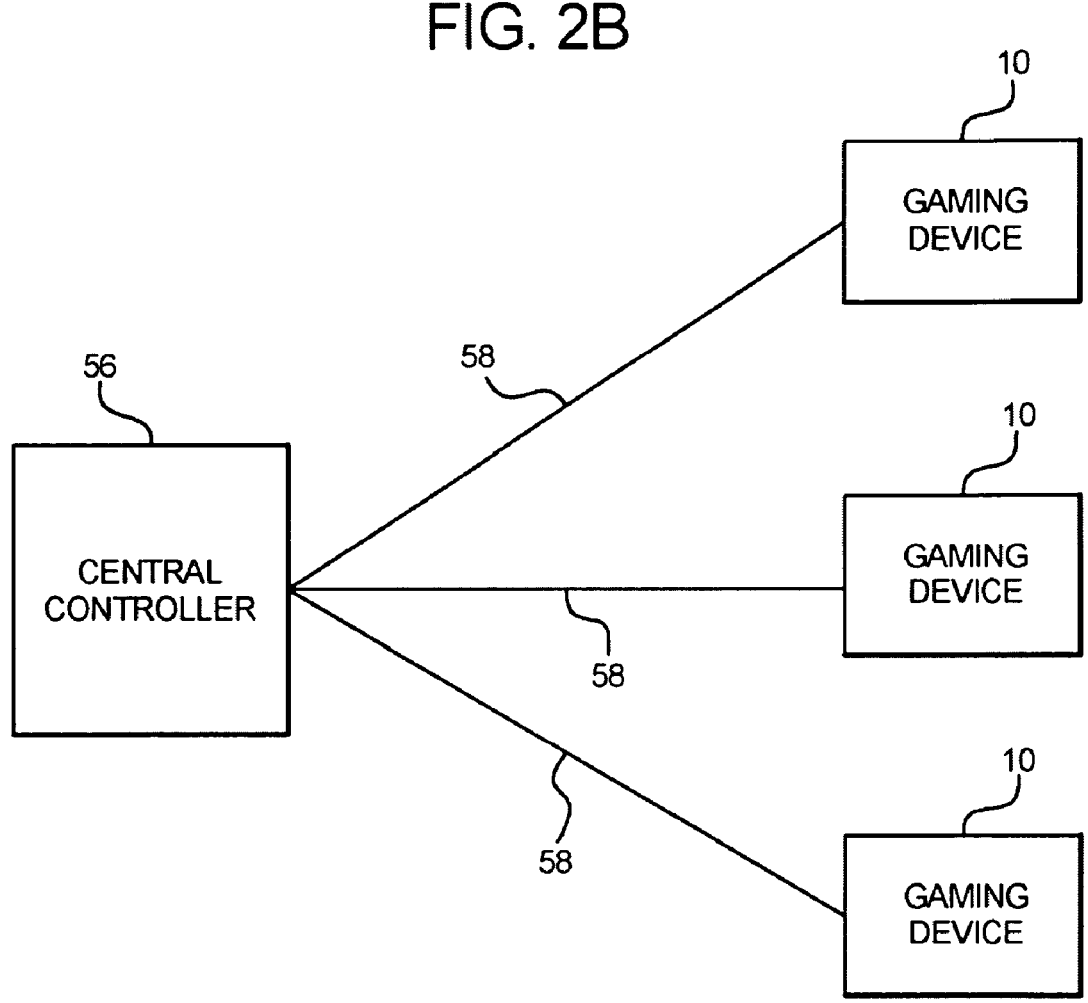
FIG. 2B is a schematic block diagram of one embodiment of a network configuration for a plurality of gaming devices disclosed herein.

In one embodiment, as illustrated in FIG. 2B, one or more of the gaming devices 10 are in communication with each other and/or at least one central controller 56 through a data network or remote communication link 58. In this embodiment, the central server, central controller or remote host is any suitable server or computing device which includes at least one processor and at least one memory or storage device. In different such embodiments, the central server is a progressive controller or a processor of one of the gaming devices in the gaming system. In these embodiments, the processor of each gaming device is designed to transmit and receive events, messages, commands, or any other suitable data or signal between the individual gaming device and the central server. The gaming device processor is operable to execute such communicated events, messages, or commands in conjunction with the operation of the gaming device. Moreover, the processor of the central server is designed to transmit and receive events, messages, commands, or any other suitable data or signal between the central server and each of the individual gaming devices. The central server processor is operable to execute such communicated events, messages, or commands in conjunction with the operation of the central server. It should be appreciated that one, more or each of the functions of the central controller, central server or remote host as disclosed herein may be performed by one or more gaming device processors. It should be further appreciated that one, more or each of the functions of one or more gaming device processors as disclosed herein may be performed by the central controller, central server or remote host.

In one embodiment, the game outcome provided to the player is determined by a central server or controller and provided to the player at the gaming device. In this embodiment, each of a plurality of such gaming devices are in communication with the central server or controller. Upon a player initiating game play at one of the gaming devices, the initiated gaming device communicates a game outcome request to the central server or controller.

In one embodiment, the central server or controller receives the game outcome request and randomly generates a game outcome for the primary game based on probability data. In another embodiment, the central server or controller randomly generates a game outcome for the secondary game based on probability data. In another embodiment, the central server or controller randomly generates a game outcome for both the primary game and the secondary game based on probability data. In this embodiment, the central server or controller is capable of storing and utilizing program code or other data similar to the processor and memory device of the gaming device.

In an alternative embodiment, the central server or controller maintains one or more predetermined pools or sets of predetermined game outcomes. In this embodiment, the central server or controller receives the game outcome request and independently selects a predetermined game outcome from a set or pool of game outcomes. The central server or controller flags or marks the selected game outcome as used. Once a game outcome is flagged as used, it is prevented from further selection from the set or pool and cannot be selected by the central controller or server upon another wager. The provided game outcome can include a primary game outcome, a secondary game outcome, primary and secondary game outcomes, or a series of game outcomes such as free games.

The central server or controller communicates the generated or selected game outcome to the initiated gaming device. The gaming device receives the generated or selected game outcome and provides the game outcome to the player. In an alternative embodiment, how the generated or selected game outcome is to be presented or displayed to the player, such as a reel symbol combination of a slot machine or a hand of cards dealt in a card game, is also determined by the central server or controller and communicated to the initiated gaming device to be presented or displayed to the player. Central production or control can assist a gaming establishment or other entity in maintaining appropriate records, controlling gaming, reducing and preventing cheating or electronic or other errors, reducing or eliminating win-loss volatility, and the like.

In another embodiment, a predetermined game outcome value is determined for each of a plurality of linked or networked gaming devices based on the results of a bingo, keno, or lottery game. In this embodiment, each individual gaming device utilizes one or more bingo, keno, or lottery games to determine the predetermined game outcome value provided to the player for the interactive game played at that gaming device. In one embodiment, the bingo, keno, or lottery game is displayed to the player. In another embodiment, the bingo, keno or lottery game is not displayed to the player, but the results of the bingo, keno, or lottery game determine the predetermined game outcome value for the primary or secondary game.

In the various bingo embodiments, as each gaming device is enrolled in the bingo game, such as upon an appropriate wager or engaging an input device, the enrolled gaming device is provided or associated with a different bingo card. Each bingo card consists of a matrix or array of elements, wherein each element is designated with a separate indicia, such as a number. It should be appreciated that each different bingo card includes a different combination of elements. For example, if four bingo cards are provided to four enrolled gaming devices, the same element may be present on all four of the bingo cards while another element may solely be present on one of the bingo cards.

In operation of these embodiments, upon providing or associating a different bingo card with each of a plurality of enrolled gaming devices, the central controller randomly selects or draws, one at a time, a plurality of the elements. As each element is selected, a determination is made for each gaming device as to whether the selected element is present on the bingo card provided to that enrolled gaming device. This determination can be made by the central controller, the gaming device, a combination of the two, or in any other suitable manner. If the selected element is present on the bingo card provided to that enrolled gaming device, that selected element on the provided bingo card is marked or flagged. This process of selecting elements and marking any selected elements on the provided bingo cards continues until one or more predetermined patterns are marked on one or more of the provided bingo cards. It should be appreciated that in one embodiment, the gaming device requires the player to engage a daub button (not shown) to initiate the process of the gaming device marking or flagging any selected elements.

After one or more predetermined patterns are marked on one or more of the provided bingo cards, a game outcome is determined for each of the enrolled gaming devices based, at least in part, on the selected elements on the provided bingo cards. As described above, the game outcome determined for each gaming device enrolled in the bingo game is utilized by that gaming device to determine the predetermined game outcome provided to the player. For example, a first gaming device to have selected elements marked in a predetermined pattern is provided a first outcome of win $10 which will be provided to a first player regardless of how the first player plays in a first game, and a second gaming device to have selected elements marked in a different predetermined pattern is provided a second outcome of win $2 which will be provided to a second player regardless of how the second player plays a second game. It should be appreciated that as the process of marking selected elements continues until one or more predetermined patterns are marked, this embodiment ensures that at least one bingo card will win the bingo game and thus at least one enrolled gaming device will provide a predetermined winning game outcome to a player. It should be appreciated that other suitable methods for selecting or determining one or more predetermined game outcomes may be employed.

In one example of the above-described embodiment, the predetermined game outcome may be based on a supplemental award in addition to any award provided for winning the bingo game as described above. In this embodiment, if one or more elements are marked in supplemental patterns within a designated number of drawn elements, a supplemental or intermittent award or value associated with the marked supplemental pattern is provided to the player as part of the predetermined game outcome. For example, if the four corners of a bingo card are marked within the first twenty selected elements, a supplemental award of $10 is provided to the player as part of the predetermined game outcome. It should be appreciated that in this embodiment, the player of a gaming device may be provided a supplemental or intermittent award regardless of whether the enrolled gaming device's provided bingo card wins or does not win the bingo game as described above.

In another embodiment, one or more of the gaming devices are in communication with a central server or controller for monitoring purposes only. That is, each individual gaming device randomly generates the game outcomes to be provided to the player and the central server or controller monitors the activities and events occurring on the plurality of gaming devices. In one embodiment, the gaming network includes a real-time or on-line accounting and gaming information system operably coupled to the central server or controller. The accounting and gaming information system of this embodiment includes a player database for storing player profiles, a player tracking module for tracking players and a credit system for providing automated casino transactions.

In one embodiment, the gaming device disclosed herein is associated with or otherwise integrated with one or more player tracking systems. Player tracking systems enable gaming establishments to recognize the value of customer loyalty through identifying frequent customers and rewarding them for their patronage. In one embodiment, the gaming device and/or player tracking system tracks any player's gaming activity at the gaming device. In one such embodiment, the gaming device includes at least one card reader 38 in communication with the processor. In this embodiment, a player is issued a player identification card which has an encoded player identification number that uniquely identifies the player. When a player inserts their playing tracking card into the card reader to begin a gaming session, the card reader reads the player identification number off the player tracking card to identify the player. The gaming device and/or associated player tracking system timely tracks any suitable information or data relating to the identified player's gaming session. Directly or via the central controller, the gaming device processor communicates such information to the player tracking system. The gaming device and/or associated player tracking system also timely tracks when a player removes their player tracking card when concluding play for that gaming session. In another embodiment, rather than requiring a player to insert a player tracking card, the gaming device utilizes one or more portable devices carried by a player, such as a cell phone, a radio frequency identification tag or any other suitable wireless device to track when a player begins and ends a gaming session. In another embodiment, the gaming device utilizes any suitable biometric technology or ticket technology to track when a player begins and ends a gaming session.

During one or more gaming sessions, the gaming device and/or player tracking system tracks any suitable information or data, such as any amounts wagered, average wager amounts, and/or the time at which these wagers are placed. In different embodiments, for one or more players, the player tracking system includes the player's account number, the player's card number, the player's first name, the player's surname, the player's preferred name, the player's player tracking ranking, any promotion status associated with the player's player tracking card, the player's address, the player's birthday, the player's anniversary, the player's recent gaming sessions, or any other suitable data. In one embodiment, such tracked information and/or any suitable feature associated with the player tracking system is displayed on a player tracking display 40. In another embodiment, such tracked information and/or any suitable feature associated with the player tracking system is displayed via one or more service windows (not shown) which are displayed on the central display device and/or the upper display device.

In one embodiment, a plurality of the gaming devices are capable of being connected together through a data network. In one embodiment, the data network is a local area network (LAN), in which one or more of the gaming devices are substantially proximate to each other and an on-site central server or controller as in, for example, a gaming establishment or a portion of a gaming establishment. In another embodiment, the data network is a wide area network (WAN) in which one or more of the gaming devices are in communication with at least one off-site central server or controller. In this embodiment, the plurality of gaming devices may be located in a different part of the gaming establishment or within a different gaming establishment than the off-site central server or controller. Thus, the WAN may include an off-site central server or controller and an off-site gaming device located within gaming establishments in the same geographic area, such as a city or state. The WAN gaming system may be substantially identical to the LAN gaming system described above, although the number of gaming devices in each system may vary relative to one another.

In another embodiment, the data network is an internet or intranet. In this embodiment, the operation of the gaming device can be viewed at the gaming device with at least one internet browser. In this embodiment, operation of the gaming device and accumulation of credits may be accomplished with only a connection to the central server or controller (the internet/intranet server) through a conventional phone or other data transmission line, digital subscriber line (DSL), T-1 line, coaxial cable, fiber optic cable, or other suitable connection. In this embodiment, players may access an internet game page from any location where an internet connection and computer or other internet facilitator is available. The expansion in the number of computers and number and speed of internet connections in recent years increases opportunities for players to play from an ever-increasing number of remote sites. It should be appreciated that the enhanced bandwidth of digital wireless communications may render such technology suitable for some or all communications, particularly if such communications are encrypted. Higher data transmission speeds may be useful for enhancing the sophistication and response of the display and interaction with the player.

As mentioned above, in one embodiment, the present disclosure may be employed in a server-based gaming system. In one such embodiment, as described above, one or more gaming devices are in communication with a central server or controller. The central server or controller may be any suitable server or computing device which includes at least one processor and a memory or storage device. In alternative embodiments, the central server is a progressive controller or another gaming machine in the gaming system. In one embodiment, the memory device of the central server stores different game programs and instructions, executable by a gaming device processor, to control the gaming device. Each executable game program represents a different game or type of game which may be played on one or more of the gaming devices in the gaming system. Such different games may include the same or substantially the same game play with different pay tables. In different embodiments, the executable game program is for a primary game, a secondary game or both. In another embodiment, the game program may be executable as a secondary game to be played simultaneous with the play of a primary game (which may be downloaded to or fixed on the gaming device) or vice versa.

In this embodiment, each gaming device at least includes one or more display devices and/or one or more input devices for interaction with a player. A local processor, such as the above-described gaming device processor or a processor of a local server, is operable with the display device(s) and/or the input device(s) of one or more of the gaming devices.

In operation, the central controller is operable to communicate one or more of the stored game programs to at least one local processor. In different embodiments, the stored game programs are communicated or delivered by embedding the communicated game program in a device or a component (e.g., a microchip to be inserted in a gaming device), writing the game program on a disc or other media, or downloading or streaming the game program over a dedicated data network, internet, or a telephone line. After the stored game programs are communicated from the central server, the local processor executes the communicated program to facilitate play of the communicated program by a player through the display device(s) and/or input device(s) of the gaming device. That is, when a game program is communicated to a local processor, the local processor changes the game or type of game played at the gaming device.

In another embodiment, a plurality of gaming devices at one or more gaming sites may be networked to the central server in a progressive configuration, as known in the art, wherein a portion of each wager to initiate a base or primary game may be allocated to one or more progressive awards. In one embodiment, a progressive gaming system host site computer is coupled to a plurality of the central servers at a variety of mutually remote gaming sites for providing a multi-site linked progressive automated gaming system. In one embodiment, a progressive gaming system host site computer may serve gaming devices distributed throughout a number of properties at different geographical locations including, for example, different locations within a city or different cities within a state.

In one embodiment, the progressive gaming system host site computer is maintained for the overall operation and control of the progressive gaming system. In this embodiment, a progressive gaming system host site computer oversees the entire progressive gaming system and is the master for computing all progressive jackpots. All participating gaming sites report to, and receive information from, the progressive gaming system host site computer. Each central server computer is responsible for all data communication between the gaming device hardware and software and the progressive gaming system host site computer. In one embodiment, an individual gaming machine may trigger a progressive award win. In another embodiment, a central server (or the progressive gaming system host site computer) determines when a progressive award win is triggered. In another embodiment, an individual gaming machine and a central controller (or progressive gaming system host site computer) work in conjunction with each other to determine when a progressive win is triggered, for example through an individual gaming machine meeting a predetermined requirement established by the central controller.

In one embodiment, a progressive award win is triggered based on one or more game play events, such as a symbol-driven trigger. In other embodiments, the progressive award triggering event or qualifying condition may be achieved by exceeding a certain amount of game play (such as number of games, number of credits, or amount of time), or reaching a specified number of points earned during game play. In another embodiment, a gaming device is randomly or apparently randomly selected to provide a player of that gaming device one or more progressive awards. In one such embodiment, the gaming device does not provide any apparent reasons to the player for winning a progressive award, wherein winning the progressive award is not triggered by an event in or based specifically on any of the plays of any primary game. That is, a player is provided a progressive award without any explanation or alternatively with simple explanations. In another embodiment, a player is provided a progressive award at least partially based on a game triggered or symbol triggered event, such as at least partially based on the play of a primary game.

In one embodiment, one or more of the progressive awards are each funded via a side bet or side wager. In this embodiment, a player must place or wager a side bet to be eligible to win the progressive award associated with the side bet. In one embodiment, the player must place the maximum bet and the side bet to be eligible to win one of the progressive awards. In another embodiment, if the player places or wagers the required side bet, the player may wager at any credit amount during the primary game (i.e., the player need not place the maximum bet and the side bet to be eligible to win one of the progressive awards). In one such embodiment, the greater the player's wager (in addition to the placed side bet), the greater the odds or probability that the player will win one of the progressive awards. It should be appreciated that one or more of the progressive awards may each be funded, at least in part, based on the wagers placed on the primary games of the gaming machines in the gaming system, via a gaming establishment or via any suitable manner.

In another embodiment, one or more of the progressive awards are partially funded via a side-bet or side-wager which the player may make (and which may be tracked via a side-bet meter). In one embodiment, one or more of the progressive awards are funded with only side-bets or side-wagers placed. In another embodiment, one or more of the progressive awards are funded based on player's wagers as described above as well as any side-bets or side-wagers placed.

In one alternative embodiment, a minimum wager level is required for a gaming device to qualify to be selected to obtain one of the progressive awards. In one embodiment, this minimum wager level is the maximum wager level for the primary game in the gaming machine. In another embodiment, no minimum wager level is required for a gaming machine to qualify to be selected to obtain one of the progressive awards.

In another embodiment, a plurality of players at a plurality of linked gaming devices in a gaming system participate in a group gaming environment. In one embodiment, a plurality of players at a plurality of linked gaming devices work in conjunction with one another, such as by playing together as a team or group, to win one or more awards. In one such embodiment, any award won by the group is shared, either equally or based on any suitable criteria, amongst the different players of the group. In another embodiment, a plurality of players at a plurality of linked gaming devices compete against one another for one or more awards. In one such embodiment, a plurality of players at a plurality of linked gaming devices participate in a gaming tournament for one or more awards. In another embodiment, a plurality of players at a plurality of linked gaming devices play for one or more awards wherein an outcome generated by one gaming device affects the outcomes generated by one or more linked gaming devices.

Game Having an Award Based on a Spatial Relationship Between Emblems and Positionable Accumulators In one embodiment, the gaming system disclosed herein provides a game including displaying a plurality of emblems in a field, each emblem representing an opportunity to win an award for a play of a game. In one embodiment, for a play of the game, the gaming system enables a player to indicate a desired position for one or more positionable accumulators within the field, each positionable accumulator also representing an opportunity to win an award for a play of the game. The gaming system stores a set of accumulator positioning criteria. If the player indicates a valid position for the one or more accumulators based on the accumulator positioning criteria, the gaming system determines whether the inputted position causes any of the emblems to become collected or winning emblems. The gaming system indicates any collected emblems and provides an award for the play of the game based on the collected emblems. The game provided by the disclosed gaming system may be a primary or base game playable upon receiving a wager from a player. Alternatively, the game may be a secondary or bonus game playable upon the occurrence of a suitable triggering event in a primary or base game.

Figure 3A:
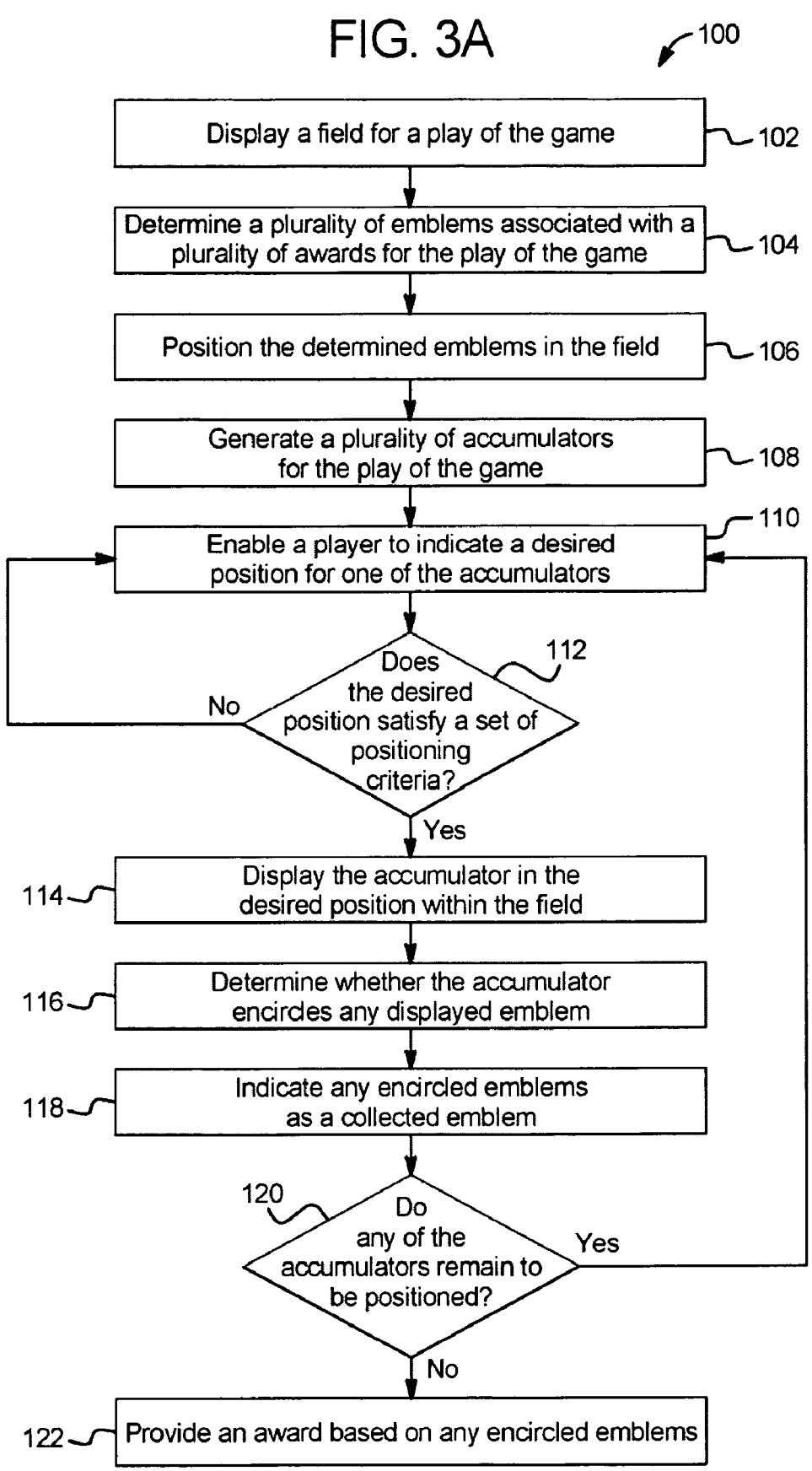
FIG. 3A is a flow chart of an example process for operating the game disclosed herein.

FIG. 3A illustrates a flow chart of an example process 100 for operating a gaming system providing the game disclosed herein. Although the example process 100 for operating the gaming system for providing the disclosed game is described with reference to the flow chart illustrated in FIG. 3A, many other methods of operating a gaming system are contemplated. For example, the order of certain of the steps of process 100 may be changed, and certain of the steps of process 100 are optional.

In various embodiments, the gaming system disclosed herein displays a field for a play of the game, as indicated by block 102. In one such embodiment, the gaming system displays the field using one or more display devices 16 of one or more gaming devices in the gaming system. In another such embodiment, the gaming system displays the field using one or more communal display devices usable by each of a plurality of gaming devices (and visible to a plurality of players at the plurality of gaming devices) of the gaming system. In one embodiment, the gaming system displays the field as a two-dimensional space in which emblems can be displayed and accumulators can be positioned. In another embodiment, the gaming system displays the field as a three-dimensional space wherein the emblems and the accumulators each occupy a volume of the space.

In one embodiment, the gaming system generates a plurality of emblems for the play of the game, as indicated by block 104. In various embodiments, at least one of the emblems is associated with at least one value or potential award, as indicated by block 104. In various embodiments, the award includes one or more selected from the group consisting of credits, additional plays of the game, multipliers, physical prizes, or other suitable awards. In one embodiment, wherein the game is a primary or base game, the quantity of emblems and any awards associated with the emblems are generated based, at least in part, on a wager provided by the player. In another embodiment, wherein the game is a secondary or bonus game, the quantity of emblems and any awards associated with the emblems are generated based, at least in part, on a triggering event generated for a play of an associated primary or base game.

In one embodiment, the gaming system positions and displays the plurality of emblems as emblems within the field, as indicated by block 106. In one such embodiment, the gaming system displays each generated emblem for the play of the game. In another such embodiment, the gaming system displays fewer than all of the emblems for the play of the game. In this embodiment, one or more emblems are masked emblems and are not visible to the player prior to positioning any accumulators. In one embodiment, each of the displayed emblems is stationary within the field. In another embodiment, at least one of the displayed emblems is not stationary and is displayed as moving within the field. It should be appreciated that each positioned emblem, whether masked or visible, stationary or non-stationary, preferably represents an opportunity to win an award for the play of the game.

In one embodiment, the plurality of emblems are displayed as spaced-apart emblems in the field. In this embodiment, none of the emblems is displayed as adjacent to or abutting any other emblem. In one embodiment, each of the spaced-apart emblems is displayed as stationary during the play of the game. In other embodiments, for at least a portion of a play of the game, two or more of the emblems are not spaced-apart and are displayed as abutting, adjacent to, or sharing the same space of the field as one another.

The gaming system preferably positions the emblems within the field based on random determinations made about each emblem. In one such embodiment, the gaming system selects a random position for each emblem. In a further embodiment, the position for each emblem is also based, at least in part, on an award associated with the emblem. In another embodiment, the gaming system stores data indicating a plurality of levels. In this embodiment, the positions of at least one of the emblems are predetermined and are stored in association with a particular level. In one embodiment, the gaming system enables a player to access different levels based on the positions selected for the accumulators of previous levels, such as based on a determination of how nearly a player positions the accumulators in conformance with an optimal set of positions. It should be appreciated that in this embodiment, a game configuror or operator of the gaming system may design each of the plurality of levels such that achieving a maximum award for each level requires differing levels of player skill. It should be further appreciated that the gaming system may sequentially provide the levels in an increasing order of difficulty, in a decreasing order of difficulty, or in any other sequence determined by the game configuror or operator of the gaming system. In one embodiment, the gaming system positions the emblems such that each of the emblems can be collected if the player optimally positions the plurality of accumulators within the field. In one embodiment, the quantities, sizes, and shapes of the accumulators associated with a particular level are randomly determined. In one embodiment, the total surface area of the accumulators of a particular level is predetermined, but the gaming system provides a plurality of accumulators which make up the total surface area by randomly determining shapes and sizes for the accumulators. In one such embodiment, the gaming system determines a total surface area equal to the size of the field for the play of the game, and subdivides the area of the field into accumulators of randomly determined sizes and shapes. In one embodiment, the gaming system determines the sizes and shapes of the accumulators after generating and displaying the plurality of emblems. In one such embodiment, the gaming system determines the sizes and shapes of the accumulators such that optimal positioning of the accumulators results in a designated quantity of the emblems (such as all of the emblems or fewer than all of the emblems) being collected.

The gaming system preferably also generates a plurality of accumulators for the play of the game, as indicated by block 108. In one embodiment, each accumulator is displayed as a symbol having a predefined accumulator shape. In this embodiment, the accumulator shape defines a perimeter for the accumulator which is usable to determine an impact of an indicated accumulator position for a play of the game. In various embodiments, the gaming system indicates the quantity of generated accumulators to the player. In one such embodiment, the gaming system simultaneously displays each of the generated accumulators in an area separate from the field, such that a player of the gaming system can see the quantity, size, and shape of the generated accumulators. In another embodiment, the gaming system does not indicate the quantity of accumulators to the player. In this embodiment, the gaming system displays the generated accumulators serially, such that the player is unsure of the total quantity of accumulators available for the play of the game. In one embodiment, the quantities, sizes, and shapes of the accumulators are based on a wager made on a play of the game. In another embodiment, the quantities, sizes, and shapes of the accumulators are based on an outcome of an associated primary game that triggers the play of the game. In one embodiment, the gaming system generates the accumulators based on stored data representing a plurality of levels. In this embodiment, the quantities, sizes, and shapes of the accumulators are based the particular level provided to the player of the gaming system. It should be appreciated that accumulators for a particular level may also enable the gaming system game configuror or operator to control the skill required for a player to position the accumulators to obtain a maximum prize for that level.

In various embodiments, the gaming system enables the player to indicate a desired position for one of the accumulators within the field, as indicated by block 110. In one such embodiment, the gaming system displays each of the plurality of accumulators and enables the player to select one of the accumulators and to indicate a desired position for that accumulator. In another embodiment, the gaming system displays only one of the plurality of accumulators and enables the player to indicate a desired position for the displayed accumulator prior to displaying and enabling the player to position any other accumulator.

In one embodiment, after the player indicates a desired position for one of the accumulators, the gaming system determines whether the desired position satisfies the accumulator positioning criteria, as indicated by diamond 112. In one embodiment, the gaming system makes this determination based on one or more of the accumulator shape and the perimeter of the accumulator defined by the accumulator shape. In one embodiment, the accumulator positioning criteria require that the positioned accumulator does not overlap any other, previously positioned accumulator. In this embodiment, the gaming system determines whether the desired position provided by the player would cause the positioned accumulator to overlap any other accumulator and thus to be in a prohibited position. In another embodiment, the accumulator positioning criteria require that the indicated position causes the perimeter of the positioned accumulator to be adjacent to or touching the perimeter a previously positioned accumulator. In another embodiment, the accumulator positioning criteria require that the perimeter of the positioned accumulator not be adjacent to or touching the perimeter of any previously positioned accumulator.

If the positioned accumulator does not satisfy the accumulator positioning criteria, as indicated by diamond 112, the gaming system indicates the failure to the player and enables the player to indicate a different position for the accumulator, as indicated by block 110.

If the accumulator position indicated by the player satisfies the accumulator positioning criteria (i.e., the positioned accumulator does not overlap any other accumulator), as indicated by diamond 112, the gaming system displays the positioned accumulator at the desired position within the field, as indicated by block 114.

It should be appreciated that the disclosed gaming system preferably enables a player to indicate a desired position and displays the accumulator at the desired position substantially simultaneously—that is, the gaming system preferably does not display an indication that it is determining whether the player's indicated desired position satisfies the positioning criteria. For example, the gaming system may enable the player to select a location, and may immediately thereafter display the accumulator in the selected location if the selected location is an allowed location. If the selected location is not an allowed location (i.e., the selected location does not satisfy the positioning criteria), the gaming system may display a message to the player indicating that the selected position is not allowed. Alternatively the gaming system may simply enable the player to indicate another desired position until the player indicates an allowed desired position.

In various embodiments, the gaming system disclosed herein determines whether the positioned accumulator satisfies the accumulator positioning criteria with respect to any of the emblems so as to collect such emblems. In one embodiment, the gaming system determines whether the positioned accumulator encircles any displayed emblems within the field, as indicated by block 116. In this embodiment, the gaming system displays an indication to the player that any elements which are encircled by the positioned accumulator are collected emblems, as indicated by block 118. It should be appreciated that in this embodiment, the accumulator positioning criteria define collected emblems as those emblems which are encircled by any accumulator. It should be appreciated that in this embodiment, the gaming system determines whether the indicated position for a particular accumulator satisfies the accumulator positioning criteria by (1) determining whether the indicated position is allowed and (2) determining whether the indicated position results in any of the emblems being collected emblems. It should be further appreciated that even if the indicated position does not fully satisfy the accumulator positioning criteria by causing any emblems to be collected, the disclosed gaming system preferably still displays the positioned accumulator if the indicated position is an allowed position.

In various other embodiments, the accumulator positioning criteria define alternative spatial relationships between positioned accumulators and emblems which cause the emblem to be a collected emblem. In one such embodiment, the accumulator positioning criteria require that a positioned accumulator abut or touch an emblem of the field for the emblem to be collected. In another such embodiment, the accumulator positioning criteria require that an emblem not be encircled by any accumulator for the emblem to be collected.

In one embodiment, after determining whether the accumulator satisfies the accumulator positioning criteria such that the indicated position is an allowed position and after determining whether any emblems are collected based on the accumulator positioning criteria, the gaming system determines whether any accumulators remain to be positioned for the play of the game, as indicated by diamond 120. If one or more accumulators remain to be positioned, as indicated by diamond 120, the gaming system enables the player to position one of the remaining accumulators, as indicated by block 110.

If no additional accumulators remain to be positioned (i.e., the player has positioned all the accumulators) for a play of the game, as indicated by diamond 120, the gaming system provides an award for the play of the game, as indicated by block 122. The award provided for the play of the game is in one embodiment based on at least one award value associated with at least one of the collected emblems for the play of the game. In one embodiment, the award is based, at least in part, on the extent to which the player-selected positions of the accumulators follows an optimal set of positions for the accumulators. In other embodiments, the award is based in part on a quantity of emblems collected for the play of the game, on a quantity of accumulators which cause a single emblem to be a collected emblem (i.e., a quantity of accumulators which encircle one emblem) for the play of the game, on a quantity of symbols associated with collected emblems for the play of the game, on time period which elapses during positioning of the accumulators, or on any other suitable factors.

FIG. 3B illustrates a flow chart of an example process 1000 for operating a gaming system providing the game disclosed herein. Although the example process 1000 for operating the gaming system for providing the disclosed game is described with reference to the flow chart illustrated in FIG. 3B, many other methods of operating a gaming system are contemplated. For example, the order of steps of process 1000 may be changed, and certain ones of the steps of process 1000 are optional.

In various embodiment, the gaming system displays a field, as indicated by block 1002, and determines a plurality of emblems associated with a plurality of awards, as indicated by block 1004, for a play of the game. The gaming system positions the emblems within the field, as indicated by block 1006. The gaming system also determines a plurality of accumulators and an accumulator positioning time limit for the play of the game, as indicated by block 1008. It should be appreciated that the accumulator positioning time limit represents a time limit in which the player must position each of the determined accumulators. The accumulator positioning time limit in various embodiments is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In one embodiment, the gaming system starts a timer usable for determining whether the accumulator positioning time limit has expired, as illustrated by block 1000. For example, the gaming system may start a timer which counts down from the accumulator positioning time limit to zero. Upon starting the time, the gaming system enables the player to indicate a desired position within the field for one of the accumulators, as indicated by block 1002, and determines whether the desired position satisfies a set of accumulator positioning criteria, as indicated by diamond 1004. If the desired position satisfies the accumulator positioning criteria, the gaming system displays the accumulator in the desired position, as indicated by block 1006, and determines whether the accumulator encircles any of the displayed emblems, as indicated by block 1008. The gaming system then determines whether any more accumulators need to be positioned, as indicated by diamond 1000. If no more accumulators need to be positioned, the gaming system provides an award based on any encircled emblems, as indicated by block 1002.

If the indicated position for the accumulator does not satisfy the accumulator positioning criteria (i.e., the indicated position overlaps another positioned accumulator), as illustrated by diamond 1004, the gaming system determines whether the accumulator positioning time limit has expired based on the timer, as indicated by diamond 1004. Similarly, if the gaming system determines that additional accumulators need to be positioned, as indicated by diamond 1000, the gaming system determines whether the accumulator positioning time limit has expired, as indicated by diamond 1004.

In either instance, if the accumulator positioning time limit has not expired, as indicated by diamond 1004, the gaming system enables the player to indicate a desired position for an accumulator (i.e., either the improperly positioned accumulator or another one of the plurality of accumulators), as indicated by block 1000. If the accumulator positioning time limit has expired, as indicated by diamond 1004, the gaming system provides an award based on any emblems which were collected (i.e., encircled) by accumulators positioned within the accumulator positioning time limit, as indicated by block 1002. It should be appreciated that this award is based on accumulators which satisfy the accumulator positioning criteria both with respect to the allowability of an indicated position and with respect to the spatial relationship required to collect one or more emblems.

FIGS. 4A, 4B, 4C, 4D, 4E, and 4F illustrate various times during a single play of one of the accumulator positioning games disclosed herein. In the illustrated embodiment, the display device 16 is contained within a gaming device of the disclosed gaming system, and includes a touch screen and touch screen controller which enable the player at the gaming device to input desired positions of the plurality of accumulators by touching the display device 16. It should be appreciated that the illustrated play of the game may be a play of a primary or base game operable upon a wager, or may be a play of a secondary or bonus game operable upon the occurrence of a suitable triggering event in a primary or base game.

Initially, it should be appreciated that for the play of the game illustrated in FIGS. 4A, 4B, 4C, 4D, 4E, and 4F, the gaming system stores a plurality of accumulator positioning criteria which define allowable positions of the accumulators, as well as the criteria for determining whether a positioned accumulator causes any of the emblems to be collected and thus to be winning emblems. In the illustrated embodiment, the accumulator positioning criteria define rules which require that the accumulators be placed entirely within the field, which require that no accumulator overlaps another accumulator, and which define a collected emblem as any emblem which is completely encircled by any single positioned accumulator. In various embodiments, the gaming system communicates the accumulator positioning criteria to the player by displaying the criteria on the cabinet of a gaming device, by enabling the player to access a display of the positing criteria (such as by providing a touch screen and touch screen controller to access the accumulator positioning criteria), or by otherwise communicating the accumulator positioning criteria to the player prior to or during a play of the game.

FIG. 4A illustrates an embodiment of the game disclosed herein prior to the player providing any input. In the illustrated embodiment, the gaming system displays a field 150 and an accumulator display area 160. The gaming system also displays a game status display area 170 for indicating game status and other pertinent information to the player.

For a play of the game, the disclosed gaming system displays a plurality of emblems 152 within the field 150. In one embodiment, each of the emblems 152 is associated with a potential award, which the gaming system displays to a player during a play of the game. In the illustrated embodiment, the associated awards include additional credits, free spins, and increased multipliers. It should be appreciated that in various embodiments, the gaming system displays other suitable awards in association with various ones of the emblems. For example, the gaming system may display associated awards such as physical prizes, coupons for complimentary services, or progressive awards. In various embodiments, the awards associated with the emblems are predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In the illustrated embodiment, each of the emblems 152 represents an opportunity for a player to receive an award for a play of the disclosed game. Moreover, the plurality of emblems 152 in the field 150 represent an opportunity for a player of the game to make determinations about which emblems 152 have associated awards most valuable to that player, and to attempt to win those awards for the play of the game.

Referring still to FIG. 4A, the gaming system also displays a plurality of accumulators 162, 164, and 166 in the accumulator display area 160 for the play of the game. Each of the accumulators 162, 164, and 166 is a positionable accumulator which represents an opportunity to win an award for a play of the game by collecting at least one emblem 152 displayed within the field 150. The gaming system enables the player to position each of the accumulators 162, 164, and 166 within the field 150 and thereby to at least partially determine the award provided for the play of the game. In the illustrated embodiment, the gaming system displays each of the accumulators available for the play of the game in accumulator display area 160 prior to the player positioning any of the accumulators. In another embodiment (not shown), the gaming system displays only a single accumulator. In this embodiment, if the gaming system enables the player to position more than one accumulator for the play of the game, the gaming system displays a second accumulator only after the player positions the first accumulator in the field 150. Further, in this embodiment the gaming system may not indicate the shape of the second accumulator to the player until after the player has positioned the first accumulator.

In the embodiment illustrated in FIG. 4A, the gaming system indicates the player's status and the goal of the game to the player. Specifically, the gaming system displays a message in status display area 170 indicating that the player may position the three displayed accumulators 162, 164, and 166 and should try to encircle as many of the emblems displayed in the field as possible. It should be appreciated that the accumulator positioning criteria discussed above are reflected in the message communicated to the player in the status display area 170. That is, the indication that the player should try to encircle as many emblems as possible reflects the accumulator positioning criterion which defines a collected or winning emblem as one which is completely encircled by any single accumulator.

In one embodiment, illustrated in FIG. 4B, the player indicates and positions one of the accumulators displayed in the accumulator display area 160. Specifically, the player indicates accumulator 162 as the first of the three accumulators 162, 164, and 166 to be positioned. In this embodiment, the player touches the accumulator on the display 16. As illustrated in the status display area 170, the gaming system displays a message to the player indicating that one of the accumulators has been selected and that the player should position the selected accumulator to encircle as many emblems as possible.

Figure 4C:
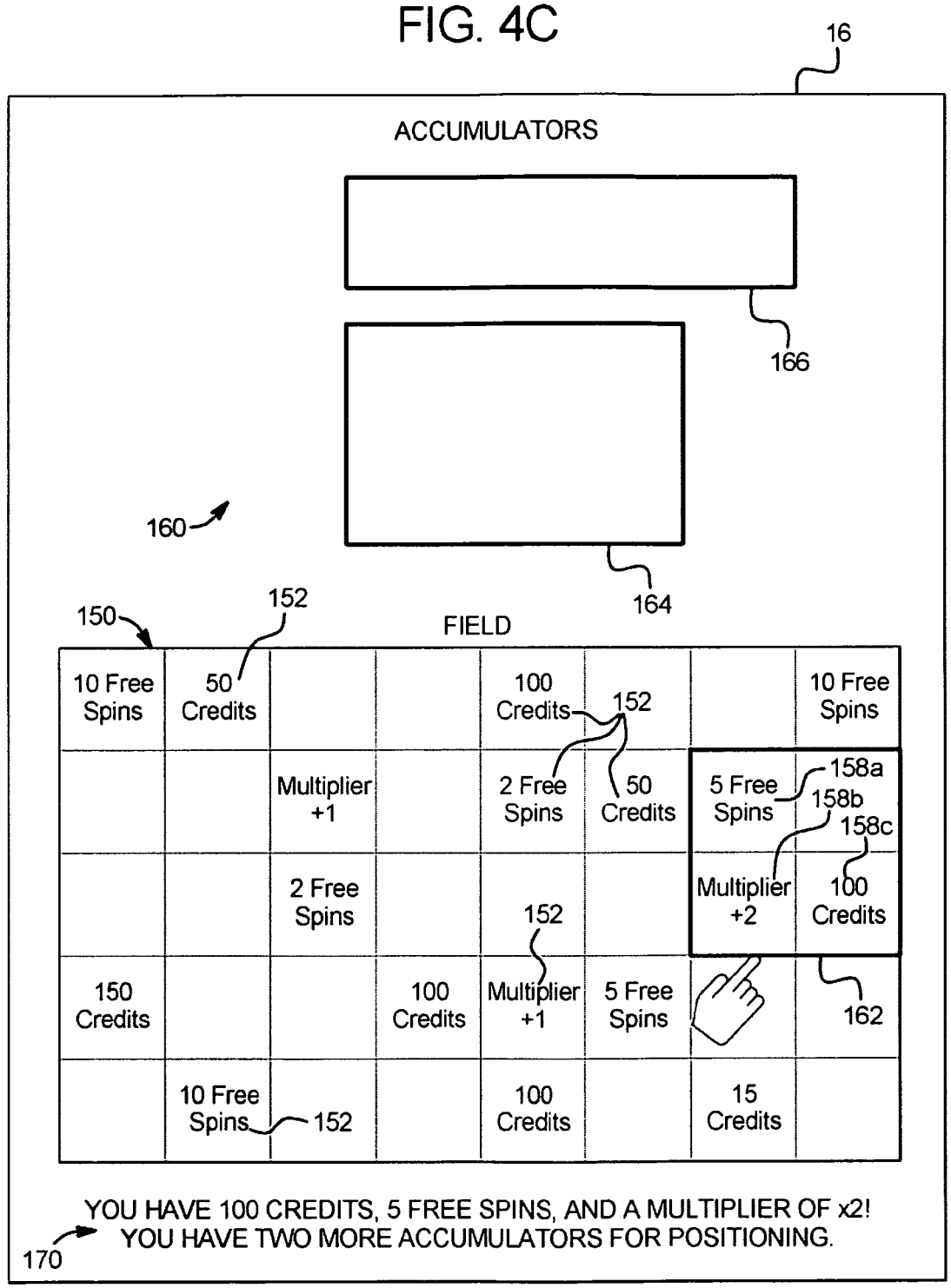

Referring now to FIG. 4C, the player indicates a position for the accumulator 162 in the field 150. In the illustrated embodiment, the player positions the accumulator 162 such that it encircles emblems 158a, 158b, and 158c. It should be appreciated that the selected position for the accumulator (1) satisfies the accumulator positioning criteria because the accumulator 162 is entirely within the field and does not overlap any other accumulators and (2) collects emblems 158a, 158b, and 158c based on the accumulator positioning criterion that emblems are collected when they are encircled.

Upon enabling the player to position the accumulator, the gaming system updates the game status display area 170 to indicate that the player has two more accumulators to position for the play of the game. In this embodiment, the gaming system also displays an indication in the game status display area 170 of a running total of the awards associated with the encircled emblems for the play of the game. Specifically, the gaming system displays a message indicating that 100 credits, 5 free spins, and a multiplier of ×2 have been accumulated based on the single positioned accumulator 162 for the play of the game.

It should be appreciated that according to the accumulator positioning criteria stored by the illustrated gaming system, the player could have positioned the accumulator 162 anywhere in the field 150 such that the entire accumulator 162 would have been contained within the field 150. It should thus be appreciated that the player positioned the accumulator 162 as illustrated in FIG. 4C based on that player's determination of the most strategically beneficial position of the accumulator 162.

Figure 4D:
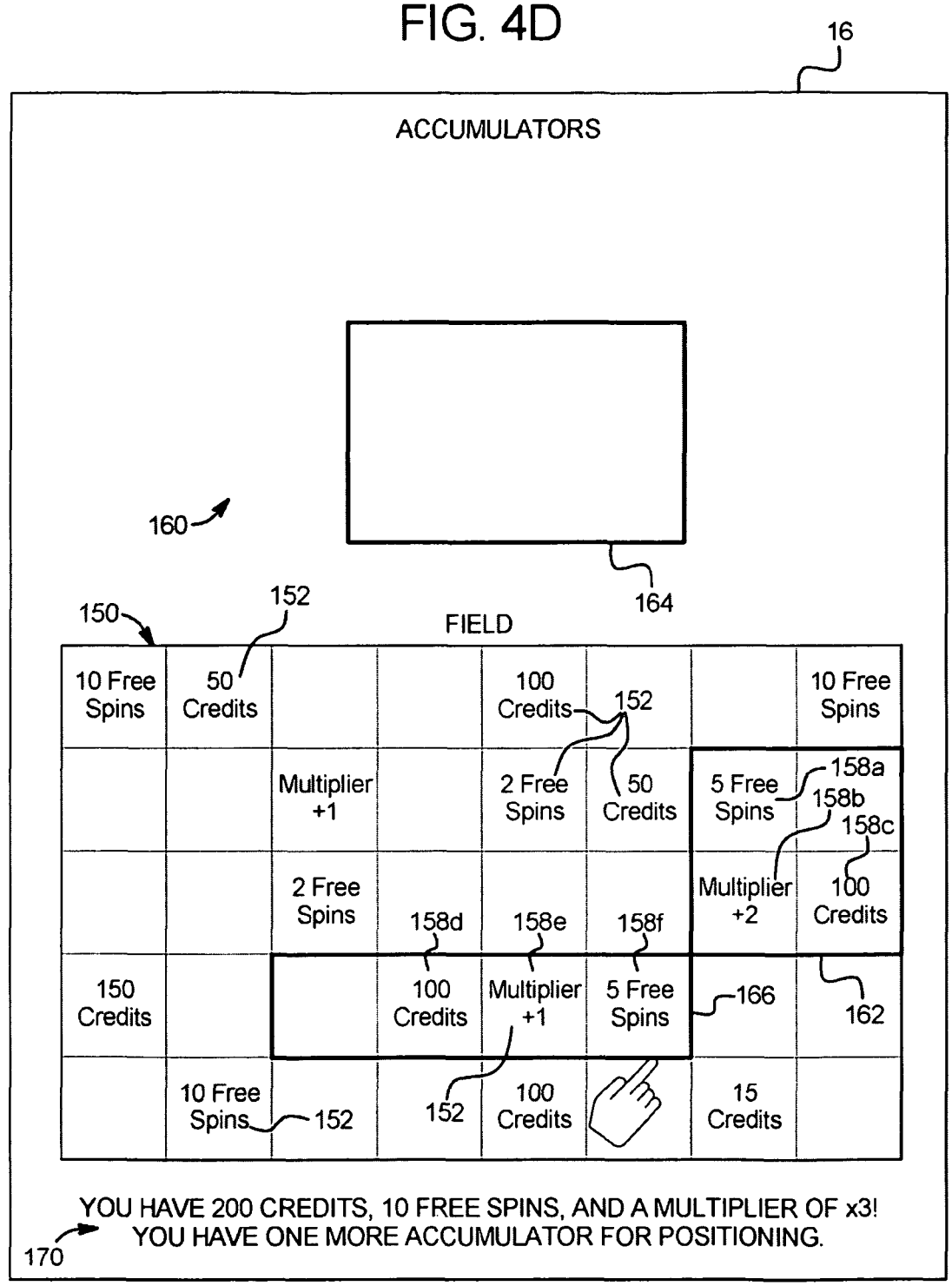

FIG. 4D illustrates the play of the game described above after the player has positioned a second accumulator 166 in the field 150. In the illustrated embodiment, the player indicates a position within the field for the accumulator 166. The indicated position satisfies the accumulator positioning criteria because the accumulator does not overlap with positioned accumulator 162 and because the accumulator 166 is contained entirely within the field 150. Moreover, based on the position of the accumulator, the accumulator positioning criteria indicate that additional emblems 158d, 158e, and 158f have been encircled and therefore collected. The gaming system thus accumulates the awards represented by emblems 158d, 158e, and 158f and indicates the total award accumulated for the play of the game in the game status display area 170. Specifically, the gaming system indicates that the player has accumulated 200 credits, 10 free spins, and a multiplier of ×3. The game status display area 170 further indicates that the player has one more accumulator 164 remaining to position for the play of the game. It should be appreciated that the selected position for the accumulator 166 represents the player's determination as to the best position for the accumulator within the constraints defined by the accumulator positioning criteria.

Figure 4E:
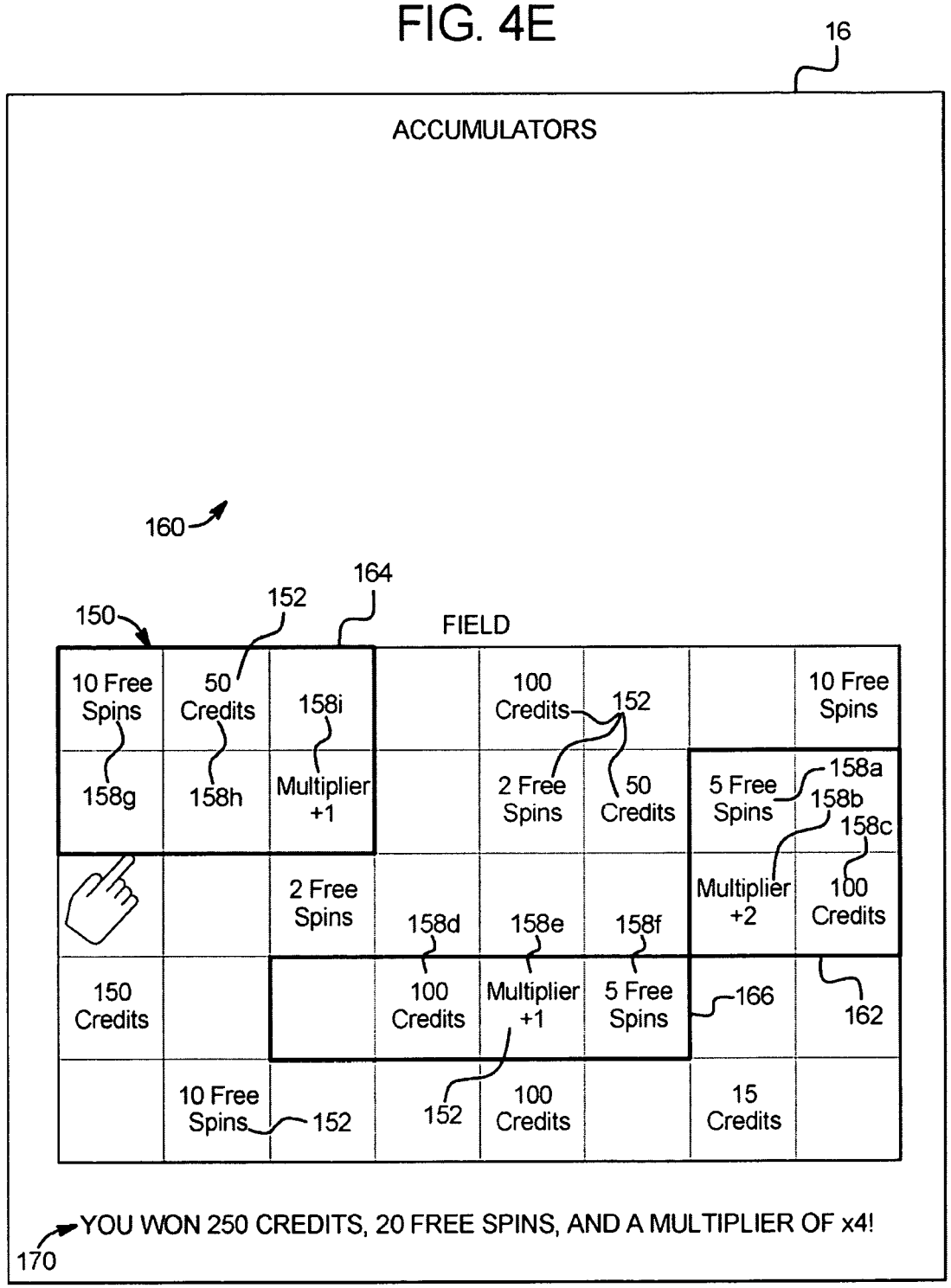

FIG. 4E illustrates the play of the game illustrated in FIGS. 4A, 4B, 4C, and 4D after the player has positioned all three positionable accumulators 162, 164, and 166 in the player-determined best positions according to the accumulator positioning criteria. As illustrated, the player indicates a desired position for the accumulator 164 within the field 150. The gaming system allows the indicated position according to the accumulator positioning criteria, as the accumulator 164 is contained entirely within the field 150 and does not overlap the other positioned accumulators 162 or 166. Moreover, the indicated position for the accumulator 164 encircles three additional emblems 158*g*, 158*h*, and 158*i*, thus collecting these three emblems. The gaming system indicates that each of the emblems 158*g*, 158*h*, and 158*i* are winning emblems. For the illustrated play of the game, the gaming system indicates the total award based on each of the winning emblems 158*a* to 158*i*. Specifically, the gaming system displays a message in the game status display area 170 indicating that the total award for the play of the game includes 250 credits, 20 free spins, and a multiplier of ×4. Because each of the accumulators has been positioned in the embodiment illustrated in FIG. 4E, the gaming system does not display an indication that any accumulators remain to be positioned. In one embodiment, the gaming system provides the total award to the player, ending the play of the game.

FIG. 4F illustrates an alternative end to the play of the game illustrated in FIGS. 4A, 4B, 4C, and 4D. Specifically, in the embodiment illustrated in FIG. 4F, the gaming system is configured to position at least one emblem within the field 150 which is invisible or hidden to the player prior to positioning the accumulators 162, 164, and 166. This invisible or hidden emblem is associated with an award which is preferably higher than the awards associated with any displayed or visible emblems. In this embodiment, the gaming system is configured to reveal the hidden emblem only if one of the positioned accumulators completely encircles the hidden emblem according to the accumulator positioning criteria.

In the embodiment illustrated in FIG. 4F, the player positioned the first two positionable accumulators 162 and 166 as in FIGS. 4A, 4B, 4C, and 4D. Thus, emblems 158*a* to 158*f* are winning emblems for the play of the game, as discussed above. The player decided to position accumulator 164 differently in FIG. 4F than in FIG. 4E. It should be appreciated that in both FIGS. 4E and 4F, the player positioned the accumulator 164 so as to encircle three emblems. Therefore, the embodiment illustrated in FIG. 4F may represent a desired placement for a player who values multipliers and credits more heavily than free spins. It should be appreciated that based on the new position for the accumulator 164, emblem 158*i* is still a collected emblem, and emblems 159*a* and 159*b* are collected emblems for the play of the game illustrated in FIG. 4F which were not collected for the position of the accumulator 164 illustrated in FIG. 4E.

Moreover, for the illustrated play of the game, the gaming system determines that the accumulator 164 is positioned such that it completely encircles hidden emblem 180. As a result, the gaming system displays hidden emblem 180, including the award associated with the emblem 180. The gaming system displays a message in the game status display area 170 indicating that the player has won 500 credits, 12 free spins, and a multiplier of ×4.

It should be appreciated that the gaming system in the illustrated embodiment only displays hidden emblem 180 after the player encircles the hidden emblem with one of the accumulators, as provided for in the accumulator positioning criteria. It should be further appreciated that in various embodiments, the hidden emblem 180 includes a different type of award from the other emblems, such as a physical prize or progressive award. It should also be appreciated that in various embodiments, the gaming system indicates to the player that one or more hidden emblems is positioned within the field 150, thus providing incentive for the player to position accumulators so as to encircle portions of the field which do not include visible emblems.

In an alternative embodiment of the game disclosed herein, illustrated in FIGS. 5A, 5B, 5C, and 5D, the gaming system does not provide positionable accumulators in the form of closed geometric shapes. In this embodiment, the gaming system provides a total length (displayed as a plurality of line segments each having the same length) and enables the player to construct one or more closed geometric shapes using the plurality of line segments to collect one or more emblems for the play of the game.

Figure 5A:
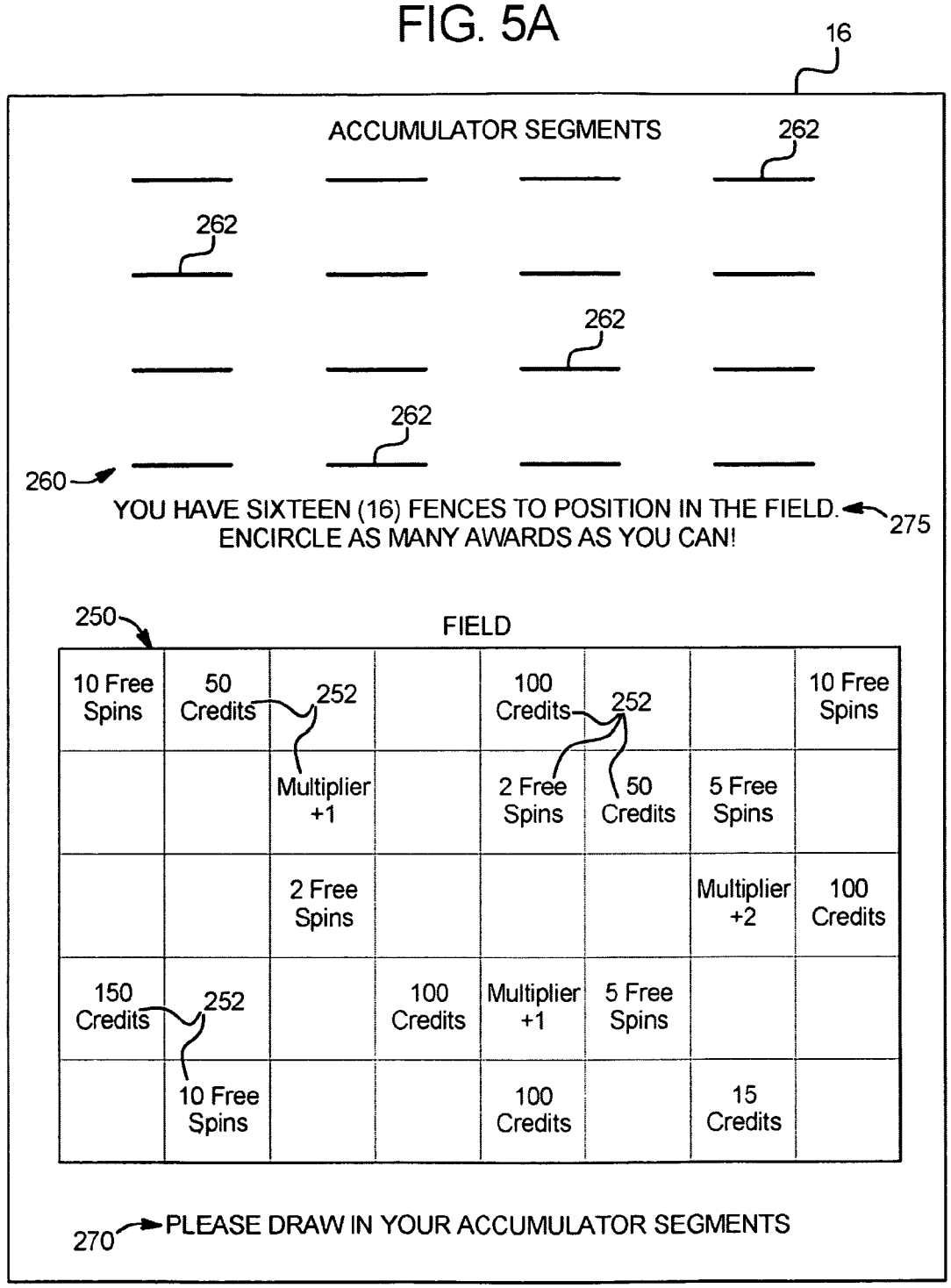

Referring to FIG. 5A, the gaming system provides a player with a field 250 including a plurality of emblems such as emblems 252. The emblems 252 each represent an opportunity to win an award for a play of the game. The gaming system also displays an accumulator display area 260 which includes a plurality of accumulators 262. Each of the accumulators 262 also represents an opportunity to win an award for a play of the game. The gaming system provides game status display areas 270 and 275 for providing status messages to the player during a play of the game. It should be appreciated that the gaming system illustrated in FIGS. 5A, 5B, 5C, and 5D includes the same set of accumulator positioning criteria as the gaming system of FIGS. 4A, 4B, 4C, 4D, 4E, and 4F—that is, no closed geometric shape formed by the accumulators 262 may overlap another such closed geometric shape, and no accumulator may be positioned outside the field 250. Moreover, as in FIGS. 4A, 4B, 4C, 4D, 4E, and 4F, the accumulator positioning criteria of the gaming device illustrated in FIGS. 5A, 5B, 5C, and 5D define a collected emblem as one which is completely encircled by a closed geometric shape formed by the player-positioned accumulators 262.

FIG. 5A illustrates a front elevation view of a display 16 of the disclosed gaming system at the beginning of a play of the game. The gaming system of FIG. 5A displays field 250 including a plurality of emblems 252 and accumulator display area 260 including sixteen (16) accumulator segments or accumulator components 262. The accumulator segments 262 are illustrated as a plurality of fences for positioning in the field 250. In the illustrated embodiment, the gaming system displays an indication in game status display area 270 instructing the player to draw in the sixteen accumulator segments 262 within the field 250. Moreover, the game status display area 275 indicates the goal of the game to the player—namely, to encircle as many of the emblems 252 as possible by constructing a closed geometric shape (i.e., an accumulator) using the accumulator segments 262. It should be appreciated that the goal of the game in the illustrated embodiment is based on the accumulator positioning criteria. That is, because the accumulator positioning criteria define a collected emblem as one which is encircled by an accumulator, the goal of the game stated in the status display area 275 is to encircle as many awards as possible by positioning one or more accumulator segments.

Figure 5B:
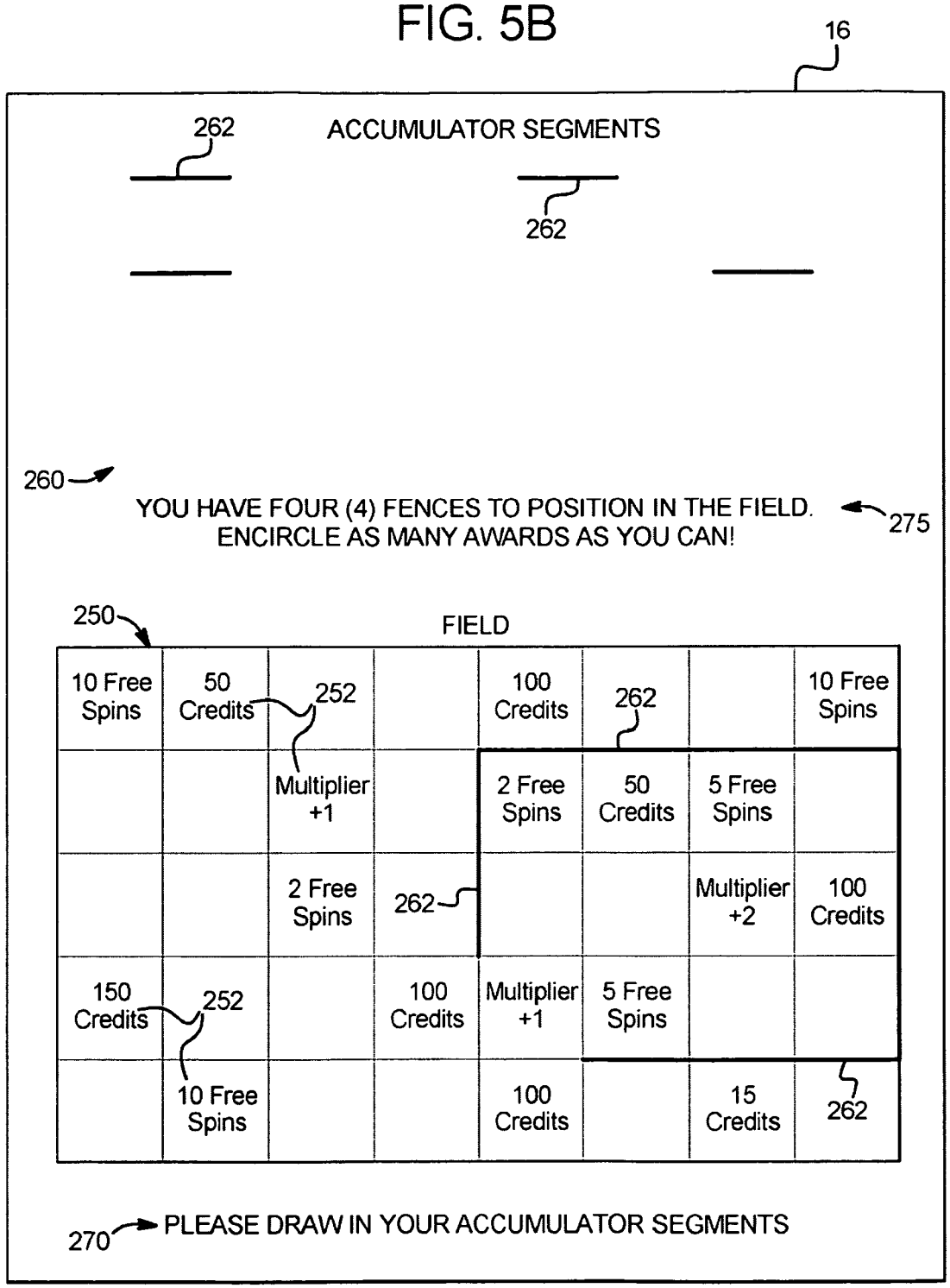

FIG. 5B illustrates the disclosed gaming system at a point in time during the positioning of the accumulator segments 262 as disclosed herein. As illustrated in FIG. 5B, the player has positioned all but four accumulator segments 262 within the field 250. Thus, the game status display area 275 indicates that the player has four accumulator segments remaining to be positioned, and reiterates the goal of the game. It should be appreciated that in the illustrated embodiment, the positioned accumulator segments 262 do not result in any of the emblems being collected, as none of the emblems are completely encircled by a closed geometric shape (i.e., an accumulator) constructed by the positioned accumulator segments 262.

FIG. 5C illustrates the display 16 of the disclosed gaming system after all accumulator segments 262 have been positioned in the field 250. The game status display area 275 includes a message which indicates that all the accumulator segments 262 (fences) have been positioned. As illustrated, the positioned accumulator segments 262 form a closed geometric shape or accumulator 280.

Referring still to FIG. 5C, the closed geometric shape 280 formed by the accumulator segments 262 encircles eight emblems 258. Thus, the gaming system determines that the eight encircled emblems 258 are collected, winning emblems. The gaming system displays a message in game status display area 270 indicating that the player has won an award for the play of the game based on the winning emblems 258. Specifically, the game status display area 270 indicates that the player has won 250 credits, 12 free spins, and a multiplier of ×3. The gaming system provides the appropriate award to the player and terminates the play of the game.

Referring now to FIG. 5D, an alternative embodiment of the disclosed gaming system is displayed wherein the player positioned the accumulator segments 262 differently within the field 250 for the play of the game than illustrated in FIGS. 5B and 5C. Specifically, the embodiment illustrated in FIG. 5D indicates that the player elected to form three enclosed geometric shapes or accumulators by positioning the accumulator segments 262 as opposed to the single enclosed geometric shape formed in FIG. 5C. Thus, for the play of the game illustrated by FIG. 5D, the gaming system determines that emblems 298 are winning emblems. Based on the winning emblems 298, the gaming system provides an award including 1050 credits, 15 free spins, and a multiplier of ×2. This award is reflected in the message displayed in the game status display area 270.

It should be appreciated that in the illustrated embodiment, the emblem representing the relatively large award of 1000 credits, which is positioned in relative distant relation to the remainder of the emblems, incentivizes the player utilizing at least four of the sixteen accumulator segments to collect that emblem and thereby receive the award of 1000 credits. It should be further appreciated that by providing sixteen total accumulator segments for positioning by the player, the gaming system enables the player to make strategic decisions regarding which emblems are the most valuable, and then to position the accumulator segments to form closed geometric shapes in a way which the player perceives maximizes the value of the award provided.

In one embodiment, the award provided for the play of the disclosed game is based in part on the quantity of different enclosed shapes created by positioning the accumulator segments. It should be appreciated that in this embodiment, the gaming system incentivizes the player positioning the accumulator segments in an arrangement such as in FIG. 5D as opposed to positioning the accumulator segments in an arrangement such as in FIG. 5C. In another embodiment, the award for the play of the game is based in part on a total area of the field enclosed by the one or more closed geometric shapes. For example, the gaming system may provide an increased award for a lesser total enclosed area. Alternatively, the gaming system may provide an increased award for greater total area. It should thus be appreciated that the disclosed gaming system may provide the player with a goal defined not only by a quantity of emblems to be collected, but by other suitable characteristics of the selected sizes, shapes, and positions of the accumulators for the play of the game.

In one embodiment, the gaming system enables a player to position additional accumulator segments to form additional closed geometric shapes for the play of the game based on one or more wagers made by the player. For example, the gaming system enables the player to place an additional or bonus wager and to receive at least one additional or bonus accumulator segment for the play of the game. In various embodiments, the quantity of accumulator segments provided to the player for the play of the game is predetermined, randomly determined, determined based on the player's status (such as determined through a player tracking system), determined based on a generated symbol or symbol combination, determined based on a random determination by the central controller, determined based on a random determination at the gaming system, determined based on the player's primary game wager, determined based on time (such as the time of day), determined based on an amount of coin-in accumulated in one or more pools or determined based on any other suitable method or criteria.

In one embodiment, at least one of the accumulator segments is not a straight line segment. In this embodiment, at least one accumulator segment has a non-linear shape, such as a curved shape or a bent shape. It should be appreciated that in this embodiment, the gaming system may enable the player to form a closed geometric shape by positioning fewer accumulator segments for the play of the game, such as by positioning only two semi-circular shaped accumulator segments for the play of the game. In various embodiments, the shape of one or more of the accumulator segments is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In one embodiment, the gaming system enables a player to position accumulator segments to form a closed geometric shape wherein at least a portion of the closed geometric shape is formed by a displayed indicia which is not an accumulator segment. In one such embodiment, the gaming system enables the player to use an edge of the field to form a closed geometric shape. In this embodiment, by positioning accumulator segments near the edge of the field, the player can form a closed geometric shape with fewer accumulator segments than would be required if the player positioned the accumulator segments relatively near the middle of the field. In one embodiment, the gaming system displays one more indicia in a position not near the edge of the field, such as in the center of the field, which is usable to form a portion of a closed geometric shape. For example, the gaming system may display a wall or fence in the middle of the field which is usable to form a portion of the perimeter of a closed geometric shape. In one embodiment, wherein the gaming system enables the player to form a closed geometric shape (i.e., an accumulator) with a triangular shape, it should be appreciated that the player can form the accumulator by positioning a single, linear accumulator segment in the corner of the field. In various embodiments, the allowed shapes of the closed geometric shapes (i.e., the accumulators) are predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

Figure 6A:
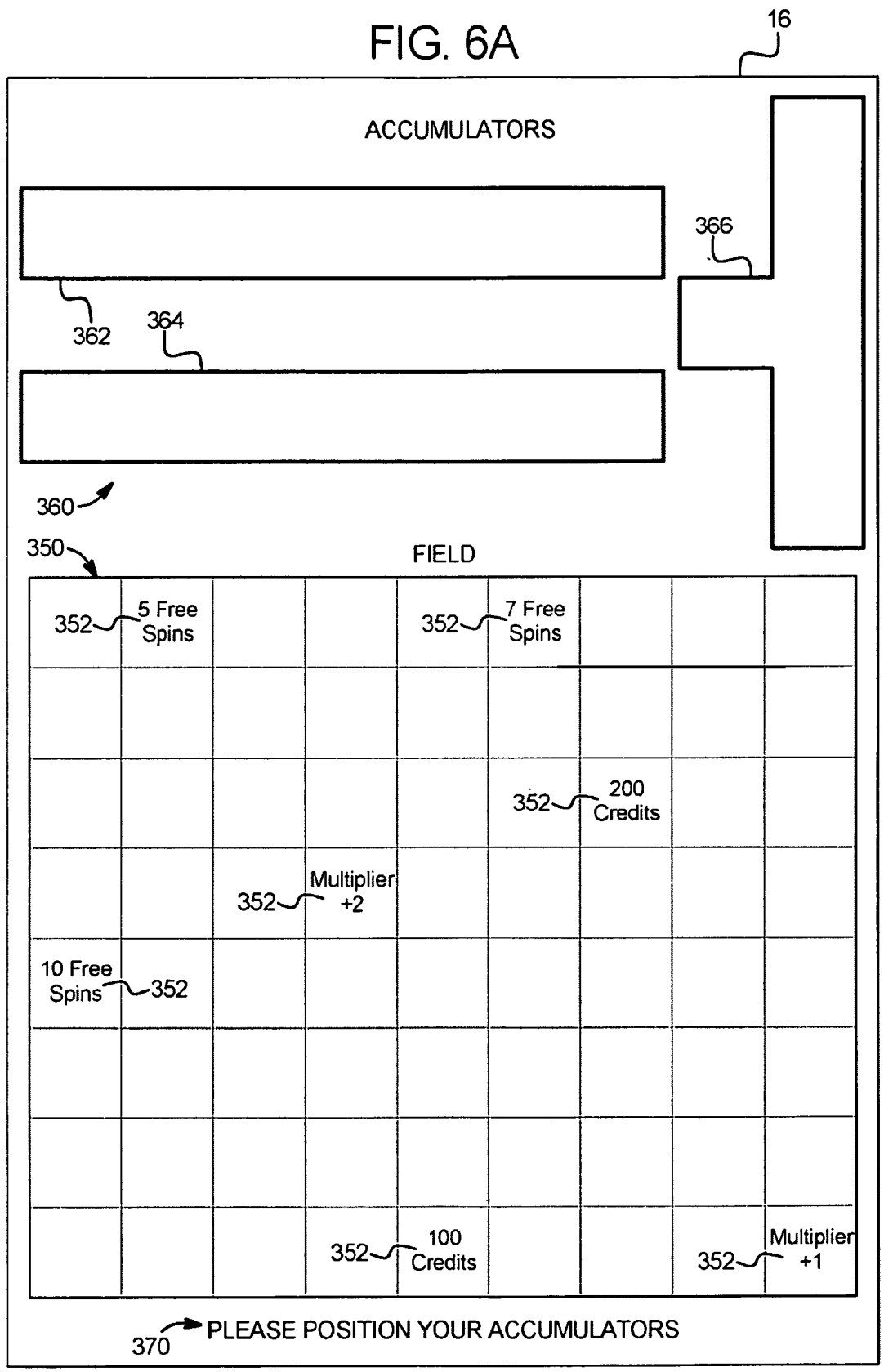
FIGS. 6A, 6B, and 6C are front elevation views of a display device of a third embodiment of the gaming system disclosed herein.
Figure 6B:
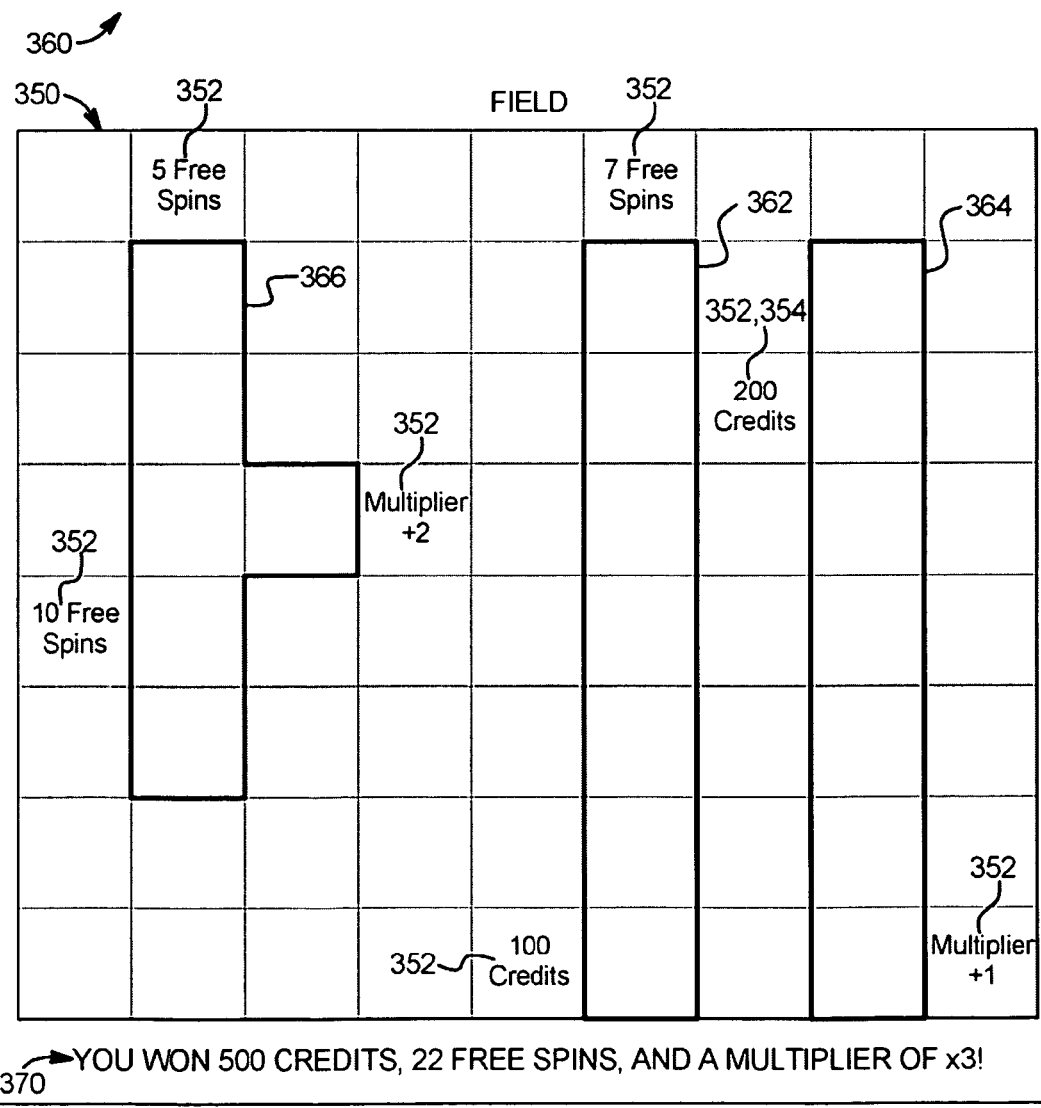
Figure 6C:
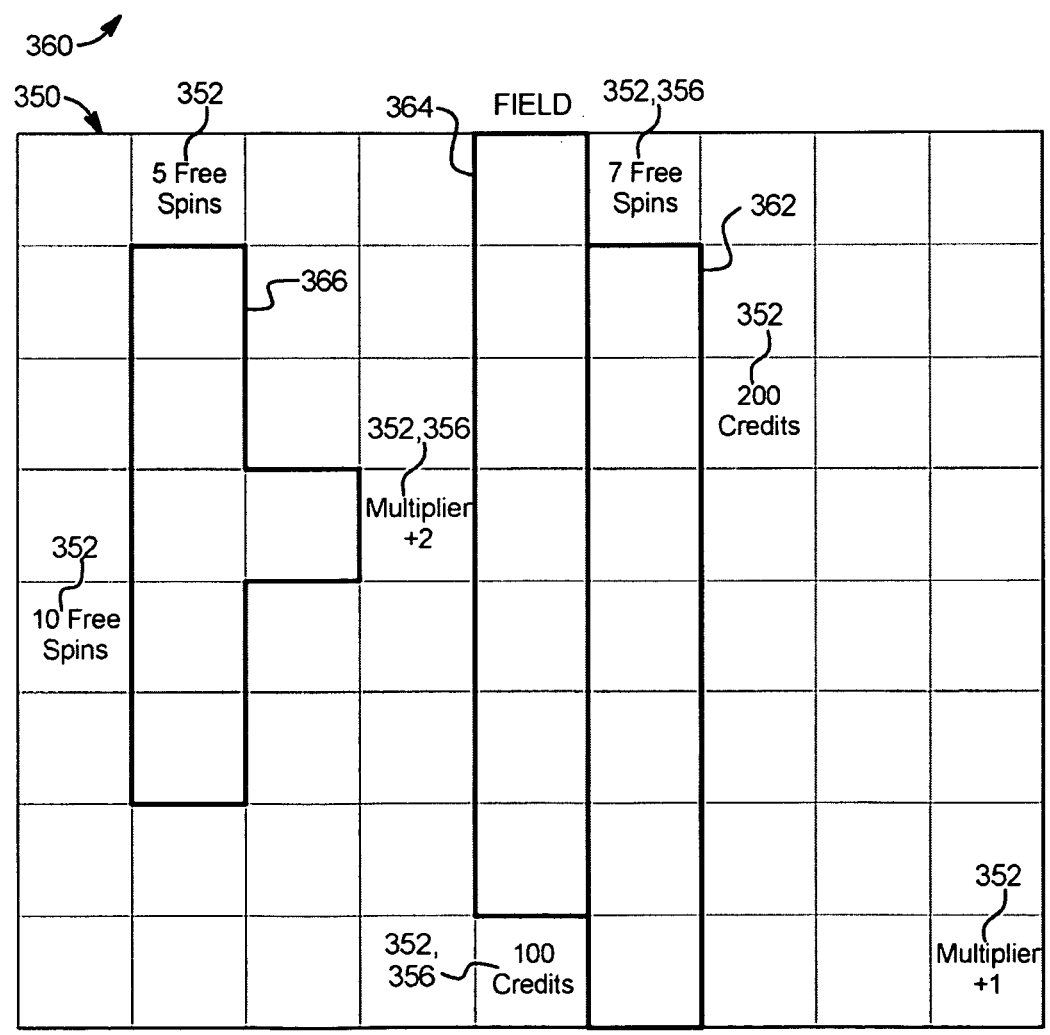

FIGS. 6A, 6B, and 6C illustrate front elevation views of a display 16 of the gaming system disclosed herein in a further alternative embodiment. Referring first to FIG. 6A, the gaming system generates and displays a plurality of emblems 352 in field 350 and a plurality of accumulators 362, 364, and 366 in accumulator area 360. Moreover, in the illustrated embodiment, the gaming system stores accumulator positioning criteria which indicate allowed positions for the accumulators 362, 364, and 366 and which indicate spatial relationships which result in the emblems being collected for a play of the game. Specifically, in the illustrated embodiment, the accumulator positioning criteria prohibit the accumulators 362, 364, and 366 from overlapping one another and from overlapping any of the emblems 352. The accumulator positioning criteria further indicate that an emblem 352 is collected if one of the sides of any emblem 352 abuts one of the sides of any of the accumulators 362, 364, or 366. The stored accumulator positioning criteria in the illustrated embodiment also indicate that if any emblem 352 abuts one of the sides of two or more different accumulators 362, 364, or 366, the award indicated by the emblem is provided multiple times according to the quantity of accumulators which abut the emblem.

FIG. 6B illustrates one outcome of a play of the game of the gaming system disclosed herein. Specifically, the player positioned the accumulators 362, 364, and 366 as illustrated in FIG. 6B. Based on the positioned accumulators, each of the emblems 352 is collected and is therefore a winning emblem. Moreover, emblem 354 is a winning emblem for which the gaming system provides the indicated award twice based on accumulators 362 and 364 both abutting one of the sides of the emblem 354. Thus, the gaming system displays a message in game status display area 370 indicating that the award for the play of the game includes 500 credits, 22 free spins, and a multiplier of ×3.

FIG. 6C illustrates an alternative outcome of a play of the game of the gaming system disclosed herein. In the embodiment illustrate by FIG. 6C, the player positioned the accumulators 362, 364, and 366 such that not all of the emblems 352 are winning emblems. However, as illustrated, emblems 356 are winning emblems based on the positions of two of the accumulators 362, 364, and 366. Thus, the gaming system provides an award based on the winning emblems, including providing the award indicated by emblems 356 twice. The gaming system provides an award including 400 credits, 29 free spins, and a multiplier of ×4 for the play of the game. The gaming system indicates this award by displaying an appropriate message in game status display area 370.

As indicated by FIGS. 6A, 6B, and 6C, the gaming system disclosed herein enables a player to make a plurality of decisions about where to place the accumulators in the field. It should be appreciated that these decisions enable the player to determine what that player perceives to be the most valuable award available for the play of the game, which increases player excitement and entertainment. Moreover, it should be appreciated that in the embodiments illustrated in FIGS. 6A, 6B, and 6C, the disclosed gaming system enables the player to prioritize various ones of the emblems and to receive the awards associated with these emblems more than once depending on the selected position for the accumulators.

Figure 7B:
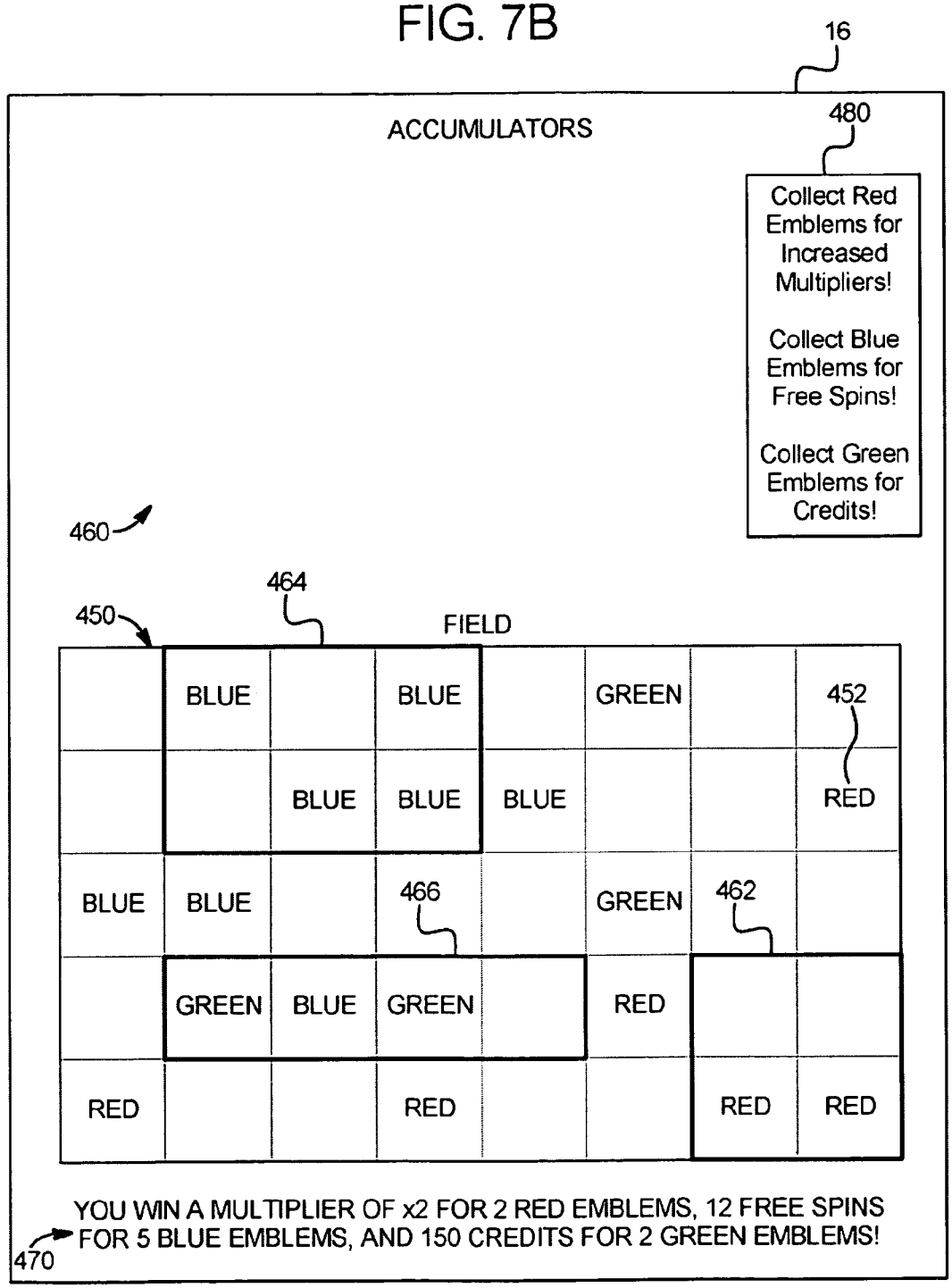

FIGS. 7A and 7B illustrate front elevation views of a display 16 of the gaming system disclosed herein in a further alternative embodiment. The gaming system illustrated in FIGS. 7A and 7B generates and displays a plurality of emblems 452 in a field 450 and a plurality of accumulators 462, 464, and 466 in accumulator area 460. The gaming system stores similar accumulator positioning criteria to that discussed with respect to FIGS. 4A, 4B, 4C, 4D, 4E, and 4F above. Specifically, the accumulator positioning criteria stored by the gaming system illustrated in FIGS. 7A and 7B recognize a collected emblem if one of the accumulators 462, 464, or 466 is positioned in the field 450 so as to completely encircle the emblem. The illustrated gaming system displays a game status display area 470 which indicates that the player should try to encircle as many colored emblems as possible.

FIGS. 7A and 7B also illustrate an award conversion area 480. In the illustrated embodiment, the award conversion area displays a message indicating awards associated with various ones of the emblems. For example, the displayed emblems 452 of FIGS. 7A and 7B are associated with the colors RED, BLUE, and GREEN. The award conversion area 480 indicates a mechanism usable by the gaming system to calculate a total award for the play of the game. Specifically, for the illustrated gaming system, the award conversion area 480 indicates that RED emblems result in increased multipliers, BLUE emblems result in free spins, and GREEN emblems result in awards of credits.

FIG. 7B illustrates an embodiment of the disclosed gaming system after the player has indicated a position within the field 450 for each of the accumulators 462, 464, and 466. In the illustrated embodiment, the three accumulators encircle two red tokens, five blue tokens, and two green tokens. It should be appreciated that the positioning of the accumulators illustrated in FIG. 7B may indicate that the particular player at the illustrated gaming system prefers free spins to increased multipliers and credits. To this end, the illustrated embodiment may indicate that the player focused on collecting blue emblems to the extent possible. As indicated in the game status display area 470, the illustrated gaming system provides an award including a multiplier of ×2, 12 free spins, and 150 credits based on the encircled or collected emblems.

It should be appreciated that by displaying a plurality of emblems wherein each emblem is not associated with a specific award, the gaming system disclosed herein may provide excitement and enjoyment to the player without requiring the player to perform mental math in an effort to maximize the player's award. Rather, the player of such a gaming system may position the plurality of accumulators 462, 464, and 466 upon determining which color is most valuable to that player. For example, the player may determine that the player wishes to win as many free spins as possible. To this end, the player may attempt to capture as many green awards as possible. Unlike the examples discussed above, the embodiment illustrated in FIGS. 7A and 7B do not require a player to compare the value of, for example, a multiplier of 3× with an award of 4 free spins.

In one embodiment, the gaming system provides the player with a quantity of accumulators for positioning in a play of the game. In a further embodiment, the gaming system indicates the quantity of accumulators available to the player prior to the player positioning any of the accumulators. In one embodiment, the gaming system enables the player to position each of the plurality of accumulators in an order desired by the player. In another embodiment, the gaming system requires the player to position the accumulators in an order determined by the gaming system. In various embodiments, the quantity of accumulators for the play of the game is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In another embodiment, the gaming system does not indicate the quantity of accumulators available to the player. In one such embodiment, the gaming system provides one or more accumulators to the player serially for positioning. In this embodiment, the player attempts to maximize the award generated as a result of the positioning of each accumulator, as the player is unsure whether another accumulator will be available for the play of the game and/or is unsure of the size and shape of any subsequent accumulator. In one embodiment, the gaming system continues to provide accumulators to the player for positioning until a game ending condition is satisfied. In one embodiment, the game ending condition is satisfied when the player cannot position an additional provided accumulator in accordance with the accumulator positioning criteria. In another embodiment, the game ending condition is satisfied when a designated amount of time has expired for a play of the game. In other embodiments, the occurrence of the game ending condition is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria. In one embodiment, the gaming system displays an indication that the game ending condition will occur. In another embodiment, the gaming system does not display any indication that the game ending condition is approaching.

In various embodiments, the gaming system is configured to position one or more emblems within the field such that the emblem is not visible to the player for the play of the game. In one such embodiment, the gaming system is configured to reveal the hidden emblem to the player only after the gaming system determines the emblem is a winning emblem for the play of the game. For instance, the gaming system only reveals the hidden emblem when the player positions an accumulator such that the accumulator completely encircles the hidden emblem. In various embodiments, the gaming system determines that one or more but not all of the emblems for a play of the game are hidden emblems. In one embodiment, the gaming system provides only hidden emblems for a play of the game and positions the hidden emblems in the field prior to enabling the player to position any accumulators. In this embodiment, the gaming system provides an awards based on any hidden emblems which are collected based on the position of one or more accumulators for the play of the game. It should be appreciated that in this embodiment, the gaming system does not provide the player with any indication of whether a desired position will result in the collection of any emblems, nor does the gaming system provide the player with any indication of the award associated with any of the hidden emblems. In various embodiments, the gaming system positions only hidden emblems but provides the player with one or more hints or clues as to the positions of the emblems and/or the awards associated with the hidden emblems.

In one embodiment, the gaming system disclosed herein enables a player to continue positioning accumulators within the field until no further positioning of accumulators is possible. In one such embodiment, the gaming system displays only the currently positionable accumulator to the player. In other embodiments, the gaming system displays at least one future positionable accumulator to the player, such as a next positionable accumulator. In this embodiment, the gaming system enables the player to position the currently positionable accumulator while considering the next positionable accumulator utilizing the player's determined strategy. In various embodiments, the shape of one or more future positionable accumulators is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In one embodiment, the gaming system disclosed herein enables the player to continue positioning accumulators until a termination condition is satisfied. In this embodiment, the player can position as many accumulators as possible to collect as many emblems as possible until an event occurs which satisfies the termination condition. In one embodiment, the termination condition is satisfied when the player positions each of the plurality of accumulators. In another embodiment, the event which satisfies the termination condition includes an accumulator positioning time period elapsing during the play of the game. In one embodiment, the termination condition is satisfied if the player cannot position one of the accumulators so as to satisfy the accumulator positioning criteria. In another embodiment, the termination condition is satisfied if the player cannot position one of the accumulators such that at least one additional emblem is collected for the play of the game. In one embodiment, at least one emblem is associated with a terminator symbol. In this embodiment, the termination condition is satisfied when the player positions one of the accumulators so as to collect the emblem associated with the termination symbol. In various embodiments, whether the termination condition is satisfied is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In one embodiment, the gaming system provides the player with one or more bonus awards based on the quantity of accumulators positioned for a play of the game. In one such embodiment, if the player positions a designated quantity of accumulators, the gaming system provides the player with a bonus award. In another embodiment, if the player positions accumulators such that each displayed emblem is collected, the gaming system provides the player with a bonus award. In another embodiment, the gaming system provides the player with a bonus award if the player positions accumulators so as to encircle or cover the entire surface area of the field.

In one embodiment, the gaming system prevents the player from removing or re-positioning a previously positioned accumulator for a play of the game. In another embodiment, the gaming system enables the player to remove or re-position at least one accumulator for a play of the game. In various embodiments, the quantity of accumulators which a player may remove or re-position is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In one embodiment, the gaming system is configured to determine whether a player's indicated position of an accumulator is an optimal position. If the position is optimal, the gaming system does not reveal any hidden emblems. If, on the other hand, the position of the accumulator is not optimal, the gaming system in one embodiment causes the position to become optimal or near-optimal by revealing a hidden emblem associated with an appropriate award. In various embodiments, the quantities and positions of any hidden emblems are predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In one embodiment, the gaming system is configured to position at least one emblem in the field which is visible but which includes a masked associated award. In this embodiment, the gaming system indicates the presence of the emblem to the player such that the player may choose whether to position an accumulator in a predetermined spatial relationship with that emblem so as to reveal the masked associated award. In this embodiment, if the player so positions an accumulator, the gaming system determines that the emblem with the masked associated award is a winning emblem, and reveals the masked associated award. In various embodiments, the masked associated award of the emblem is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In a further embodiment, the gaming system is configured to provide at least one emblem wherein the associated award of the emblem varies during the play of the game. In one such embodiment, the gaming system displays an emblem which includes a changing associated award, wherein the award is always visible (though changing) to the player. In another such embodiment, the gaming system displays an emblem wherein the associated award varies with time during a play of the game, and wherein for at least a portion of the play of the game, the award is masked from view by the player. It should be appreciated that in this embodiment, the gaming system may display one award to a player in association with an emblem, mask the award such that it is no longer visible, modify the award, and when the player positions an accumulator so as to collect the emblem, display the modified award to the player.

In a further embodiment, if the player positions an accumulator in a predetermined spatial relationship with one of the emblems (as defined by the accumulator positioning criteria) and at the time of positioning, the emblem is invisible, the gaming system determines whether or not the emblem is a winning emblem based on a probability. It should be appreciated that in one embodiment, the gaming system may provide the award associated with a hidden emblem based on a probability if the appropriate spatial relationship is achieved according to the accumulator positioning criteria even if the emblem is hidden at the point in time when the player positions the accumulator. In various embodiments, one or more emblems may remain hidden throughout a play of the game. In these embodiments, the gaming system determines whether these hidden emblems are winning emblems based on a probability if the positioned accumulator is in the predetermined spatial relationship with the hidden emblems.

In one embodiment, the gaming system displays at least one emblem as oscillating between being visible and being hidden. In this embodiment, it should be appreciated that simply positioning an accumulator in an appropriate spatial relationship with an emblem may not guarantee that the emblem is a winning emblem. Rather, in this embodiment, the gaming system requires the player to position the accumulator at a designated time such that the emblem is in the predetermined spatial relationship with the accumulator while the emblem is visible.

In various embodiments, the gaming system disclosed herein is configured to display one or more of the emblems as moving within the field during a play of the game. In one such embodiment, for a play of the game, the gaming system displays a plurality of emblems in a plurality of initial positions in the field. In this embodiment, when the play of the game begins, the gaming system displays the emblems as randomly moving within the field. In one embodiment, the emblems move within the field until they are collected by a positioned accumulator. In another embodiment, the emblems move within the field even after being collected by a positioned accumulator. In one embodiment, the gaming system is configured to make a determination for at least one collected emblem that the collected emblem escapes from the accumulator and becomes an uncollected emblem. For example, the gaming system may make a random determination for an emblem if the emblem moves to a position near the boundary of one of the positioned accumulators.

In one embodiment, the gaming system causes the emblems to move within the field at substantially uniform rate during the play of the game. In another embodiment, the gaming system causes the emblems to speed up their movement as the play of the game progresses. In a further embodiment, the gaming system requires the player to position any accumulators within an accumulator positioning period, as discussed above. In this embodiment, the gaming system may increase the speed of the moving emblems as the accumulator positioning period nears expiration. It should be appreciated that in this embodiment, the gaming system provides a different gaming experience to a player of the disclosed game, depending on the amount of time the player allows to elapse during positioning of the accumulators.

In one embodiment, the gaming system displays each positioned accumulator substantially immediately upon the player indicating a position for the accumulator. For example, when the player indicates a position for an accumulator, the gaming system immediately displays the accumulator as defining an outer boundary, and confines or collects any emblems within the accumulator. It should be appreciated that in this embodiment, despite the emblems moving within the field, the gaming system enables the player to capture a plurality of moving emblems with relative ease.

In another embodiment, the gaming system is configured to display the positioned accumulator only after a perceivable amount of time has passed since the player indicated the position of the accumulator. In one such embodiment, the gaming system displays the accumulator by slowly drawing the perimeter of the accumulator within the field. In this embodiment, if any of the emblems within the indicated perimeter of the accumulator move outside of the perimeter of the accumulator prior to the completion of the display of the accumulator, the moving emblems are not captured by the accumulator. It should be appreciated that in this embodiment, moving emblems cause the player to potentially not capture one or more emblems which are within the perimeter of a positioned accumulator at the time the player indicates the position for the accumulator based on the amount of time that elapses prior to the accumulator being drawn.

In various embodiments, the size of the positionable accumulators is known by the player for a play of the game. In an alternative embodiment, the gaming system may not display the size of one or more of the accumulators to the player prior to the player positioning the accumulator. For example, the gaming system may enable a player to select a center location for an accumulator, and may display the size of the accumulator only upon selection of the center location. In this embodiment, upon selection of the center location, the gaming system determines both the size of the accumulator and which of any emblems are winning emblems based on a plurality of probabilities associated with the accumulators. In one such embodiment, the gaming system may determine whether the emblems are winning emblems based on probabilities which decrease the farther an emblem is from the center location. In another embodiment, each emblem within the modifiable sized accumulator is a winning emblem, but the size of the accumulator is determined based on a probability. In other embodiments, the size of the accumulator is not displayed to the player, but upon positioning, a size is displayed which is predetermined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In one embodiment, the gaming system enables the player to indicate the size, shape, and position of the accumulator for a play of the game. The embodiment illustrated in FIGS. 5A, 5B, 5C, and 5D represents such an embodiment. In another embodiment, the gaming system does not constrain the player to drawing an accumulator based on a designated quantity of segments of equal lengths. In this embodiment, the gaming system enables the player to draw an accumulator having any desired shape. In various embodiments, the gaming system limits the number of emblems which can be constrained within an accumulator by only enabling the player to draw a perimeter having a designated total length, or to draw for only a certain amount of time. In various embodiments, the length of the perimeter of the accumulators or the amount of time in which the player can draw are predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In one embodiment, the gaming system enables the player to place additional wagers on additional accumulators for a play of the game. In one such embodiment, an additional wager for a play of the game causes the gaming system to provide the player with an additional positionable accumulator, and thus with an additional opportunity to collect elements and win awards. In another embodiment, the gaming system enables the player to place additional wagers on additional accumulator segments for the play of the game and to position any such additional accumulator segments to form additional closed geometric shapes.

In one embodiment, wherein the disclosed accumulator positioning game is a bonus game associated with a primary or base game, the gaming system provides an additional accumulator or accumulator segment based on an outcome of the primary or base game. In one embodiment, the gaming system indicates to the player that the player will have an opportunity to position an additional accumulator or accumulator segment. In another embodiment, the gaming system does not indicate to the player that the player will have an opportunity to position an additional accumulator or accumulator segment. In various embodiments, whether the gaming system provides the player with an additional accumulator or accumulator segment is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In one embodiment, the gaming system enables a player to collect one or more emblems more than once for a play of the game. In various embodiments, the accumulator positioning criteria define a set of rules which enable an emblem to be collected by a plurality of accumulators. In one such embodiment, the accumulator positioning criteria enable the player to position the accumulators such that the accumulators overlap. In this embodiment, a player may position two accumulators to collect the same emblem. In this embodiment, therefore, the gaming system provides any award associated with the collected emblem twice.

In another embodiment, the gaming system does not enable the accumulators to be positioned in an overlapping fashion as described, but rather defines the collection rules such that multiple accumulators can collect the same emblem. In one such embodiment, the gaming system collects an emblem if an accumulator touches the emblem. It should be appreciated that in this embodiment, multiple accumulators can touch the same emblem simultaneously without overlapping, such as indicated in FIGS. 6A, 6B, and 6C. In another embodiment, the gaming system collects emblems when encircled by an accumulator positioned in the field. In this embodiment, the gaming system is configured to remove one or more accumulators positioned during a play of a game. Thus, in this embodiment, the gaming system enables a player to position a first accumulator such that it completely encircles an emblem, collecting the emblem. The gaming system provides an award based on the collected emblem. After a passage of a designated amount of time, the gaming system removes the first accumulator and enables the player to position a second accumulator encircling the same emblem, collecting that emblem for a second time. It should be appreciated that the award associated with a same emblem can thus be provided for a same play of the game.

In one embodiment, the gaming system enables the player to collect one or more emblems for a play of the game by indicating a desired subdivision for the field. In this embodiment, the gaming system displays one or more emblems within the field as moving emblems. In one such embodiment, the subdivision of the field must be performed according to a plurality of subdividing criteria. For example, the gaming system may enable the player to subdivide the field by indicating a position of the field. In this embodiment, the gaming system draws one or more lines originating from the indicated position. If the lines are drawn all the way to the edge of the field without being displayed as contacting any emblem displayed in the field, the gaming system in one embodiment stores the subdivision as successful. In this embodiment, the subdivision may result in one or more of the emblems being contained within one or more created subdivisions of the field. In one embodiment, the gaming system provides an award to a player based on the quantity of emblems in one or more of the subdivisions of the field, such as a subdivision selected by the player or a subdivision including the largest quantity of emblems. In various embodiments, which subdivision is analyzed to determine any award is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In an alternative embodiment, wherein one or more of the emblems is displayed as a moving emblem, the gaming system enables the player to subdivide the field by indicating and drawing a desired subdivision line using the input device. In this embodiment, if the gaming system displays one of the emblems as touching or contacting the subdivision line prior to the player completing the line (i.e., prior to the subdivision of the field), the subdivision line is invalid and is removed. In one embodiment, the gaming system provides the player with a designated quantity opportunities to draw or otherwise indicate subdivision lines for the play of the game. In one embodiment, the gaming system enables the player to continue drawing or indicating subdivision lines for the play of the game until the player draws a subdivision line which is invalid (such as by an emblem contacting the subdivision line). In one embodiment, the gaming system provides an award for one or more emblems contained within the subdivision created by one or more subdivision lines. In various embodiments, which subdivision is analyzed to determine the award is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In various embodiments, one or more accumulators provides an award in addition to any awards associated with the collected emblems. In one embodiment, one or more of the accumulators is associated with a multiplier which is applied to the awards associated with any emblems collected by that accumulator. In one such embodiment, a first of the accumulators is associated with a different multiplier than a second of the accumulators. In other embodiments, one or more accumulators is associated with an additional award of credits, additional plays of a game, or any other suitable award. In one such embodiment, the gaming device indicates to the player the additional award associated with the accumulator, such that the player can attempt to select the best position to maximize the perceived award. In another such embodiment, the gaming system does not indicate the additional award associated with the accumulator to the player prior to the positioning of the accumulator. In various embodiments, the additional award associated with the accumulator is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In one embodiment, the accumulator positioning criteria define a set of rules which govern the selection of positions for the accumulators. In one embodiment, these criteria require that none of the accumulators overlap each other. In other embodiments, these accumulator positioning criteria require that each accumulator touch at least a portion of another accumulator without overlapping. In another embodiment, the accumulator positioning criteria require that each accumulator not be adjacent to or touch any other previously positioned accumulator.

In one embodiment, the accumulator positioning criteria also define a set of rules which govern whether an emblem is collected by a positioned accumulator. In one such embodiment, the accumulator positioning criteria define a set of spatial relationships which result in the collection of an emblem by an appropriately positioned accumulator. In a further embodiment, the accumulator positioning criteria require that to collect an emblem, an accumulator must encircle the emblem. In another embodiment, the accumulator positioning criteria merely require that to collect an emblem, an accumulator must touch the emblem. It should be appreciated that the gaming system disclosed herein may include any suitable accumulator positioning criteria for governing allowable positions of the accumulators and for governing when an accumulator collects an emblem. In one embodiment, the accumulator positioning criteria define a game wherein emblems are collected if they are not encircled by any accumulators. In this embodiment, the goal defined by the accumulator positioning criteria may be to position the plurality of accumulators within the field while encircling as few emblems as possible. In various embodiments, the accumulator positioning criteria are combined such that certain emblems are collected by encircling the emblems, certain emblems are collected by positioning an accumulator such that it abuts the emblem, and/or certain of the emblems are collected only if no accumulator encircles them. It should be appreciated that any suitable combinations of any suitable accumulator positioning criteria are contemplated by the instant disclosure.

In one embodiment, the gaming system does not enable a player to reposition a positioned accumulator. In another embodiment, the disclosed gaming system enables the player to reposition a previously-positioned accumulator during a play of the game. In one such embodiment, the gaming system enables the player to so reposition an accumulator at any point during the game. In another such embodiment, a first, positioned accumulator may be positioned only prior to the positioning of a second accumulator. In certain embodiments, whether the gaming system enables a player to reposition it during the play of the game is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In one embodiment, the accumulator positioning criteria change between a first play of the disclosed game and a second play of the disclosed game, or between the positioning of a first accumulator and the positioning of a second accumulator. In one embodiment, the gaming system enables the player to select one or more desired accumulator positioning criteria for a play of the game. In another embodiment, the gaming system provides the ability to select such accumulator positioning criteria as an award for a previous play of the game. In one embodiment, wherein the game is activated upon a wager by the player, the gaming system enables the player to provide an additional wager in exchange for the ability to alter the accumulator positioning criteria for the play of the game. In one embodiment, one or more emblems is associated with an accumulator positioning criterion, such that if a player collects that emblem based on the position of one of the accumulators, the gaming system alters the accumulator positioning criteria according to the associated accumulator positioning criteria of the emblem. It should be appreciated that this alteration may occur prior to the player positioning the next accumulator or may occur prior to a subsequent play of the game. In various embodiments, the ability to alter the accumulator positioning criteria is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria. In one embodiment, the gaming system enables the player to conserve the ability to alter the accumulator positioning criteria for use during a future gaming session, such as by storing an indication of the ability to alter the accumulator positioning criteria using any suitable player tracking system.

In one embodiment, one or more of the accumulators is displayed for a plurality of plays of the game. In one such embodiment, for a first play of the game, the gaming system enables the player to position an accumulator within the field. After providing an award associated with the collected emblems, the gaming system in one embodiment removes the collected emblems but continues displaying the positioned accumulator. The gaming system then generates a plurality of new emblems, some of which may be immediately collected by the already-positioned accumulator. In this embodiment, the gaming system provides an award to the player based, at least in part, on the awards associated with the newly generated, collected emblems.

In one embodiment, the field includes at least one object which is usable to form part of an accumulator. In an embodiment wherein the gaming system enables the player to position sixteen accumulators to form enclosed geometric figures, the gaming system may provide an object such as a wall within the field which is usable to effectively increase the size of the accumulators. In one such embodiment, the gaming system provides a wall such that a player only needs to construct three sides using the accumulators to form a quadrilateral-shaped geometric figure for collecting emblems.

In various embodiments, the gaming system is configured to display the accumulators, the field, and the emblems in accordance with an appropriate theme of the gaming system. In one such embodiment, the gaming system displays the field as a meadow or field. In this embodiment, the gaming system displays the plurality of emblems as a plurality of wild horses roaming the meadow or field. The gaming system causes the horses to randomly move about the field for the play of the game. Each of the horses in one embodiment includes an associated award, which may or may not be displayed in conjunction with each horse. In one embodiment, depending on the value of the associated award, one or more horses may move more quickly than other horses. For example, if one of the horses is associated with an especially large award, that horse may run around the field, as opposed to the other horses, which may walk around the field or even stand still.

In a further embodiment, the accumulators are displayed as fences for corralling the wild horses. In this embodiment, for a play of the game, the player's goal is to corral as many wild horses as possible by erecting one or more complete fences. In this embodiment, a horse has been corralled if it is captured or collected within a fence. In one embodiment, the player positions a fence by indicating a desired fence position. In one embodiment, the gaming system does not display the fence as constructed immediately upon positioning. Rather, the gaming system displays an animation representing the construction of the fence which may take a variable amount of time depending on the number of fences, the terrain on which the fence is constructed, or the size of the fence. In one embodiment, because the fences can take a substantial amount of time to construct, a player may select a position for an accumulator based on emblems contained within the accumulator at the time of positioning, but the emblems may escape the accumulator prior to construction. It should be appreciated that particularly with the higher value (i.e., faster) wild horses, a player risks losing some of the emblems during construction of the accumulator.

In another embodiment, the accumulators are displayed as border collies for corralling the emblems (i.e., the horses). In this embodiment, the player indicates a position for one of the border collies, and the gaming system displays the border collie as moving around the field in an effort to corral the horses. In this embodiment, the gaming system at various times causes one or more of the horses to escape the border collie's control, thus resulting in a non-collected emblem. The determination whether to allow the horse to escape may be based on a probability associated with the emblem. In one embodiment, the gaming system determines that an emblem is collected after it has been corralled by a border collie for a designated amount of time. In various embodiments, the designated amount of time is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In another embodiment, the field is displayed as a lake. In this embodiment, the emblems are displayed as fishes, and the accumulators are displayed as nets. In this embodiment, the gaming system includes one or more hidden emblems in the form of fishes which are under water. Thus, the gaming system can display a plurality of visible fishes on the surface of the water and a plurality of invisible fishes deeper under the water. For the play of the game, the player indicates where to position one of the nets. The gaming system displays a casting of the net, and one or more emblems are collected based on the cast net. In one embodiment, any fishes which are visible and which are within the area defined by the net are automatically collected. In another embodiment, at least one of the invisible fishes is collected based on a probability determined by the gaming system. It should be appreciated that, as described above, the gaming system displays various of the fishes as moving during the play of the game such that a casting of the net may not result in capturing each of the visible fishes within the displayed area encompassed by the net at the time of casting. In one embodiment, the gaming system does not indicate the size of the net to the player prior to the player indicating a position in which to cast. In this embodiment, the gaming system determines the size of the net at the time of casting.

In one embodiment, the gaming system disclosed herein provides a game which is impacted by an amount of time which has passed since the start of the game. In one such embodiment, the gaming device removes an accumulator from the accumulator display area if the player does not position that accumulator within a designated amount of time. In another embodiment, wherein the emblems move during the play of the game, the speed of the emblems increases as time elapses during a play of the game. It should be appreciated that this increased speed makes it more difficult for the player to accurately collect the desired emblems. In one embodiment, one or more of the awards associated with one or more of the emblems shrinks or becomes less lucrative as time elapses during the play of the game. In another embodiment, after a designated amount of time elapses, one or more of the emblems is removed from the field or is hidden such that collection of that emblem is no longer automatic, but rather is based on a probability.

In one embodiment, as time elapses during a play of the game, the accumulators become more difficult to move or become impossible to move quickly. In this embodiment, upon selecting one of the accumulators, the gaming device displays an indication that the accumulator is becoming more stationary. As the accumulator becomes more stationary, the player may position the accumulator more slowly, until the player cannot change the position of the accumulator at all.

In one embodiment, the display of an accumulator takes a relatively long amount of time. In one such embodiment, wherein the accumulators are fences and wherein the emblems are wild horses, the fence does not corral any wild horses until it is completely constructed. In this embodiment, as the fence is constructed, one or more of the horses is scared off and becomes more likely to escape the eventual enclosed area. In this embodiment, larger fences are more difficult to construct while collecting desired emblems, as the relatively longer construction time increases the probability that the emblems will escape the geometric area of the accumulator.

In another embodiment, the gaming system enables the player to draw an accumulator using the input device, such as a touch screen and a touch screen controller. In this embodiment, the accumulator is only displayed for a relatively short period of time. If the drawn accumulator does not become a completed, closed geometric shape within that short period of time, the accumulator disappears. In this embodiment, the player may therefore try to draw the accumulator quickly, which risks missing some desired emblems. Alternatively, the player may draw the accumulator more slowly, but may draw a smaller accumulator so as to complete the closed geometric shape prior to the expiration of the accumulator.

In one embodiment, the disclosed gaming system is configured to store a plurality of fields including a plurality of emblems on each field and a plurality of usable accumulators. In this embodiment, for each play of the game, the gaming system selects one of the stored fields and displays the stored emblems within the stored field. The gaming system then enables the player to use the stored accumulators to generate awards for the play of the game. It should be appreciated that by storing fields including positioned emblems and enabling the player to position stored accumulators, the gaming system can provide a series of puzzles wherein the difficulty of maximizing the award provided by each puzzle varies. In various embodiment, which of the series of puzzles is provided for a play of the game is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In one embodiment, at least one of the stored puzzles (represented as a field, a plurality of emblems, and a plurality of positionable accumulators) include at least one hint providable to the player. In one such embodiment, the hint includes an indication of an optimal position for one or more of the accumulators for the stored puzzle. In one embodiment, the gaming system provides a hint to a player for free (i.e., the player may request it at any time). In other embodiments, whether and when the hint is provided to the player is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria.

In one embodiment, the gaming system enables the player to select one of the puzzles from the plurality of stored puzzles. In this embodiment, the gaming system enables the player to risk not receiving the maximum possible award for one of the puzzles due to the difficulty of optimally positioning the plurality of accumulators. However, in one embodiment the player weighs this risk against the maximum possible award, which may vary depending on the difficulty of a given puzzle.

In one embodiment, each one of the puzzles is associated with one of a plurality of levels attainable by the player for the play of the game. In this embodiment, the gaming system determines, based on the positions of the accumulators selected for a particular level, whether to enable the player to advance to a subsequent level. For example, the gaming system may determine how nearly a set of selected accumulator positions conforms with a set of optimal accumulator positions. In another example, the gaming system may determine whether an award collected for a play of a level of the disclosed gaming system exceeds a minimum award threshold for advancing to a subsequent level. In one embodiment, the gaming system determines whether to enable a player to position accumulators for a subsequent level based on whether a level advance condition is satisfied for a play of the game. In various such embodiments, whether the level advance condition is satisfied is predetermined, randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria. In one embodiment, if a player advances through a designated number of levels (such as all the levels of the gaming system), the gaming system provides a suitable bonus award for the play of the game.

In one embodiment, the amount of the award provided for the play of the game is impacted by player error during the game. For example, if the player positions one of the accumulators in a non-optimal position, the gaming system in one embodiment automatically reduces the award provided to the player by a designated amount. In another embodiment, if a player positions one of the accumulators in a non-optimal position, the gaming system shortens the play of the game by removing at least one accumulator, at least one emblem, or both for the play of the game. In an embodiment wherein the emblems collected for the play of the game are based on a probability, the gaming system reduces this probability if the player positions one of the accumulators in a non-optimal position. In various embodiments, regardless of the reduction of the award, the gaming system provides a minimum award to the player for the play of the game. In another embodiment, the gaming system provides guidance to the player, such as by suggesting a position for an accumulator, if the potentially winnable award is reduced to below a designated minimum award. In one embodiment, if a player positions an accumulator in a non-optimal position, the gaming system reveals one or more hidden emblems to ensure that the player receives a designated minimum award for the play of the game.

In the embodiments described above, the gaming system is configured to provide a game which includes a two dimensional field. In another embodiment, the gaming system displays a three-dimensional field and enables the player to position accumulators which collect emblems in three dimensions. In this embodiment, the gaming system thus enables simulation of three dimensional environments, such as an under-sea environment. The player may position a three dimensional net to collect fishes at different longitudinal and latitudinal positions, but also at different depths under the surface of the sea. In another embodiment, the gaming system disclosed herein may enable a player to collect emblems in an outer space environment, such as using a grabber arm to collect astronauts as they float away from a space shuttle.

In one embodiment, wherein the field is displayed as three dimensional, the gaming system displays at least one accumulator as three dimensional and at least one emblem as three dimensional. In this embodiment, the gaming system determines that an emblem is a collected emblem if a volume of a positioned accumulator includes the entire volume of the emblem. In another embodiment, the gaming system determines that the emblem is collected if the volume of the positioned accumulator includes a portion of the volume of an emblem. In other embodiments, at least one accumulator and/or at least one emblem is two dimensional. In one such embodiment, the gaming system determines that a positioned accumulator collects an emblem based on a suitable spatial relationship, such as a overlap of at least one plane of a three dimensional object (i.e., an accumulator or an emblem) with at least one two dimensional object (i.e., an accumulator or an emblem).

In one embodiment, the gaming system enables a player to position one or more accumulators by indicating a desired position and also by indicating a desired rotation amount. In this embodiment, the gaming system enables the player to orient and position an accumulator freely within the field for a play of the game. In one embodiment, wherein the field is represented in three dimensions, the gaming system enables the player to rotate an accumulator about any one of a plurality of axes, such as an x-axis, a y-axis, or a z-axis. In this embodiment, the gaming system enables the player to orient the accumulator in an effort to collect as many emblems as possible.

In one embodiment, the gaming system disclosed herein enables players to position the accumulators using a touch screen and touch screen controller located at one of a plurality of gaming devices. In this embodiment, the gaming system displays the positioned accumulator on the gaming device to which the accumulator applies. In another embodiment, wherein a plurality of players position accumulators within a common field for a play of the game, the gaming system displays the common field on a communal display applicable to the plurality of gaming devices. In a further embodiment, each player uses a touch screen and touch screen controller (or other suitable input device) at each of the individual gaming devices to position the accumulators. The gaming system displays the communal field, which reflects accumulators positioned by each of the players on the communal display and on a display at each of the gaming devices.

In an alternative embodiment, the gaming system disclosed herein includes a touch-sensitive table top usable by a plurality of players to simultaneously indicate a location of an accumulator. In one such embodiment, the gaming system includes a touch sensitive table top implemented using Frustrated Total Internal Refraction (FTIR) technology to sense a plurality of simultaneous touches of the table top. For example, the gaming system may use the Surface™ product manufactured by the Microsoft Corporation. In this embodiment, the gaming system may display a plurality of reactions of the emblems to a player touching, drawing, or otherwise indicating a position of an accumulator. For example, the gaming system may display a plurality of the emblems as horses which, as the player draws an accumulator represented as a fence, are scared away by the construction of the fence. It should be appreciated that because such an FTIR surface (or other suitable multi-touch capable surface) enables a plurality of players to simultaneously indicate positions for a plurality of accumulators, the gaming system in one embodiment enables a plurality of players to simultaneously win awards for a play of the same game by utilizing the same input device.

In one embodiment, the gaming system disclosed herein enables a plurality of players to simultaneously participate in a play of the game. In one such embodiment, the gaming system enables this simultaneous participation to be competitive among the players participating in the play of the game. In this embodiment, the gaming system enables each of the plurality of players to position accumulators for a play of the game in an effort to maximize the award provided to that player. In one such embodiment, the award provided to each player is based on the awards associated with the emblems collected for the play of the game. In another such embodiment, the award provided to each player is based on a player rank during the play of the bonus game. The award may be a predetermined award which is divided among the players participating in the play of the game based on each player's success relative to the other players. Alternatively, the award may be a progressive award, wherein the top-performing player receives the progressive award regardless of the value of the progressive award. In one embodiment, the gaming system prohibits a player from positioning an accumulator such that it overlaps an accumulator of another player. In another embodiment, the gaming system removes a player's positioned accumulator after a short amount of time, such that other players can position accumulators around previously-collected emblems. In one embodiment, the gaming system disclosed herein enables multiple players to position accumulators competitively for a designated amount of time. In another embodiment, the gaming system disclosed herein enables multiple players to position accumulators competitively until each of the emblems is collected for the play of the game. In this embodiment, there is no explicit time limit; it should be appreciated, however, that the competitive nature encourages players to position accumulators as quickly as possible.

In one embodiment, the gaming system enables a plurality of players to compete in a play of the disclosed game by providing the same field and the same accumulators to each player. The gaming system then tracks the time required for each player to collect each of the emblems for the play of the game. Based on the relative speed with which the players collect the plurality of emblems, the gaming system provides awards to the players such that more effective players receive higher awards than less effective players.

In another embodiment, the gaming system disclosed herein enables a plurality of players to play the same game simultaneously in a cooperative way. In this embodiment, the gaming system provides a goal to the plurality of players, wherein each player contributes to the achievement of the group goal. In one such embodiment, the gaming system displays a plurality of emblems, and the goal of the disclosed game is to collect each of the emblems as quickly as possible. In one embodiment, each player cooperatively positions a plurality of accumulators in an effort to collect as many emblems as possible as quickly as possible. In this embodiment, the award provided to the players is based on the time which elapses during the collection of the plurality of emblems. In another embodiment, the gaming system includes a time limit. In this embodiment, if the plurality of players do not cooperatively collect all of the emblems within the time limit, the gaming system provides a reduced award or no award for the play of the game.

In various embodiments, the gaming system enables the plurality of players to utilize the accumulators of other players to increase the speed with which the emblems are collected. For example, the gaming system in one embodiment enables a plurality of players to position accumulators so as to contribute to the creation of the same enclosed geometric shape, thus allowing a larger closed geometric accumulator to be created in less time.

In various embodiments one or more players may be provided an advantage for the play of the game, such as the ability to position more accumulators or the ability to more quickly position accumulators. In various embodiments, these abilities for certain players are predetermined randomly determined, determined based on the player's status (such as determined through a player tracking system), determined based on a generated symbol or symbol combination, determined based on a random determination by the central controller, determined based on a random determination at the gaming system, determined based on one or more side wagers placed, determined based on the player's primary game wager, determined based on time (such as the time of day), determined based on an amount of coin-in accumulated in one or more pools or determined based on any other suitable method or criteria. In one embodiment, the gaming system provides awards to the players based on the quantity of emblems which each player collects for a play of the game. In this embodiment, a player who is especially effective in collecting emblems is provided a more lucrative award than a relatively less effective player.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A gaming system comprising:
    at least one processor;
    at least one display device;
    at least one input device; and
    at least one memory device storing a plurality of instructions which, when executed by the at least one processor, cause the at least one processor to operate with the at least one display device and the at least one input device, for a play of a game, to:
    (a) display a plurality of emblems in a predefined field;
    (b) enable a player to input a desired position for each of a designated number of accumulators within the predefined field in accordance with an accumulator positioning criterion, each of the accumulators having a predetermined accumulator shape which defines a perimeter of said accumulator, wherein the designated number of accumulators is at least one;
    (c) for each of a plurality of the emblems, determine if said emblem is collected based on whether the perimeter of one of the positioned accumulators has a designated spatial relationship with said emblem, wherein the perimeter of said positioned accumulator has the designated spatial relationship with said emblem if the perimeter of said positioned accumulator at least partially encircles said emblem;
    (d) for each collected emblem, display an indication that said collected emblem is collected; and
    (e) cause a game award to be provided to the player based on any collected emblems.

2. The gaming system of claim 1, wherein the plurality of instructions, when executed by the at least one processor, cause the at least one processor to determine the game award based on a quantity of collected emblems.

3. The gaming system of claim 1, wherein the designated number of accumulators is at least two.

4. The gaming system of claim 1, wherein the plurality of instructions, when executed by the at least one processor, cause the at least one processor to operate with the at least one display device and the at least one input device to display a value associated with at least one of the plurality of emblems as masked prior to enabling the player to input the desired position of any of the accumulators, and to reveal the masked value if the at least one masked emblem is collected during the play of the game.

5. The gaming system of claim 1, wherein at least one of the accumulators is associated with a value, and wherein the game award is based on the value associated with said at least one of the accumulators when the perimeter of said at least one of the accumulators has the designated spatial relationship with at least one of the emblems.

6. The gaming system of claim 1, wherein the plurality of instructions, when executed by the at least one processor, cause the at least one processor to operate with the at least one display device and the at least one input device to enable the player to input a modification to the predetermined accumulator shape of the perimeter of at least one of the accumulators.

7. The gaming system of claim 1, wherein the perimeter of said positioned accumulator has the designated spatial relationship with said emblem if the perimeter of said positioned accumulator completely encircles said emblem.

8. The gaming system of claim 1, wherein the plurality of instructions, when executed by the at least one processor, cause the at least one processor to, for each of a plurality of the emblems, determine if said emblem is collected based on whether the perimeter of said positioned accumulator has the designated spatial relationship with said emblem, wherein the perimeter of said positioned accumulator has the designated spatial relationship with one of the emblems if the perimeter of said positioned accumulator abuts said emblem.

9. The gaming system of claim 1, wherein the plurality of instructions, when executed by the at least one processor, cause the at least one processor to operate with a gaming device to determine at least one selected from the group consisting of: a quantity of displayed emblems and the designated number of accumulators based on a game outcome of a primary game displayed by said gaming device.

10. The gaming system of claim 1, wherein the game is a primary game, and wherein the plurality of instructions, when executed by the at least one processor, cause the at least one processor to operate with the at least one display device and the at least one input device to enable the player to wager on the play of the primary game and to input the desired position for the designated number of accumulators upon said wager.

11. The gaming system of claim 1, wherein the plurality of instructions, when executed by the at least one processor, cause the at least one processor to operate with the at least one display device and the at least one input device to determine a deviation between the inputted desired position of each of the designated number of accumulators and a predetermined set of accumulator positions and to cause an additional award to be provided based on said determined deviation.

12. The gaming system of claim 11, wherein the predetermined set of accumulator positions is an optimal set of accumulator positions based upon a plurality of predetermined positions of the plurality of emblems for one of a plurality of levels.

13. The gaming system of claim 1, wherein the player is a first player, and wherein the plurality of instructions, when executed by the at least one processor, cause the at least one processor to operate with the at least one input device and the at least one display device to enable the first player to input a first desired position of a first one of the accumulators, to enable a second player to input a second desired position of a second one of the accumulators, to cause a first game award to be provided to the first player based on whether the perimeter of the first one of the accumulators has the designated spatial relationship with any emblems, and to cause a second game award to be provided to the second player based on whether the perimeter of the second one of the accumulators ahs the designated spatial relationship with any emblems.

14. A gaming system comprising:
    at least one processor;
    at least one display device;
    at least one input device; and
    at least one memory device storing a plurality of instructions which, when executed by the at least one processor, cause the at least one processor to operate with the at least one display device and the at least one input device to:
    (a) display a plurality of emblems in a predefined field;
    (b) display one of a plurality of different accumulators, said displayed accumulator having a predetermined accumulator shape which defines a perimeter of said displayed accumulator;

(c) enable a player to input a desired position of the displayed accumulator within the predefined field in accordance with an accumulator positioning criterion;

(d) for each of a plurality of the emblems, determine if said emblem is collected based on whether the perimeter of the positioned accumulator has a designated spatial relationship with said emblem, wherein the perimeter of said positioned accumulator has the designated spatial relationship with said emblem if the perimeter of said positioned accumulator at least partially encircles said emblem;

(e) if a termination condition is not satisfied, display another one of the plurality of accumulators, said displayed accumulator having a predetermined accumulator shape which defines a perimeter of said displayed accumulator, and repeat (c) to (f); and (f) if the termination condition is satisfied, cause a game award to be provided the player based on any collected emblems.

15. The gaming system of claim 14, wherein the inputted desired position of the displayed accumulator is in accordance with the accumulator positioning criterion if the inputted desired position causes the displayed accumulator not to overlap any previously positioned accumulator.

16. The gaming system of claim 14, wherein the inputted desired position of the displayed accumulator is in accordance with the accumulator positioning criterion if the inputted desired position causes the perimeter of the displayed accumulator not to abut the perimeter of any previously positioned accumulator.

17. The gaming system of claim 14, wherein the inputted desired position of the displayed accumulator is in accordance with the accumulator positioning criterion if the inputted desired position causes the perimeter of the displayed accumulator to abut the perimeter of at least one previously positioned accumulator.

18. The gaming system of claim 14, wherein the game award is based on a quantity of the accumulators which are positioned prior to the termination condition being satisfied.

19. The gaming system of claim 14, wherein the plurality of instructions, when executed by the at least one processor, cause the at least one processor to operate with the at least one display device and the at least one input device to cause a bonus award to be provided to the player if each of the accumulators is positioned prior to the termination condition being satisfied.

20. The gaming system of claim 14, wherein the termination condition is satisfied if each of the plurality of emblems displayed in the predefined field is collected.

21. The gaming system of claim 14, wherein the termination condition is satisfied if a designated accumulator positioning time period elapses.

22. The gaming system of claim 14, wherein the termination condition is satisfied if no inputted desired position for the displayed accumulator satisfies each of the plurality of accumulator positioning criteria.

23. The gaming system of claim 14, wherein at least one of the emblems is associated with a terminator, and wherein the termination condition is satisfied if any emblem associated with the terminator is collected based on the inputted desired position of the displayed accumulator.

24. The gaming system of claim 14, wherein the perimeter of said positioned accumulator has the designated spatial relationship with said emblem if the perimeter of said positioned accumulator completely encircles said emblem.

25. A gaming system comprising:
at least one processor;
at least one display device;
at least one input device; and
at least one memory device storing a plurality of instructions which, when executed by the at least one processor, cause the at least one processor to operate with the at least one display device and the at least one input device, for a play of a game, to:

(a) display a plurality of emblems in a predefined field;

(b) for each of a plurality of players, enable said player to position at least one of a plurality of accumulators within the predefined field in accordance with an accumulator positioning criterion, each of the accumulators having an accumulator shape which defines a perimeter of said accumulator;

(c) for each of the plurality of emblems, determine whether said emblem is collected based on whether the perimeter of one of the positioned accumulators has a designated spatial relationship with said emblem, wherein the perimeter of said positioned accumulator has the designated spatial relationship with said emblem if the perimeter of said positioned accumulator at least partially encircles said emblem; and (d) if at least one of the plurality of emblems is collected, cause a game award to be provided to at least one of the plurality of players based on said at least one collected emblem.

26. The gaming system of claim 25, wherein the plurality of instructions, when executed by the at least one processor, cause the at least one processor to cause the game award to be provided to the single player of the plurality of players who positioned a greatest quantity of accumulators during the play of the game.

27. The gaming system of claim 25, wherein the plurality of instructions, when executed by the at least one processor, cause the at least one processor to cause the game award to be provided to the single player of the plurality of players who positioned a single accumulator whose perimeter has the designated spatial relationship with a greatest quantity of emblems.

28. The gaming system of claim 25, wherein the plurality of instructions, when executed by the at least one processor, cause the at least one processor to cause the game award to be provided to the single player of the plurality of players who positioned at least one accumulator whose perimeter has the designated spatial relationship with a designated quantity of emblems in a shortest amount of time.

29. The gaming system of claim 25, wherein if the plurality of players position the plurality of accumulators such that the perimeters of said accumulators have the designated spatial relationship with each of the plurality of emblems within a designated time period, the plurality of instructions, when executed by the at least one processor, cause the at least one processor to cause the game award to be provided to each of the plurality of players.

30. The gaming system of claim 25, wherein the plurality of instructions, when executed by the at least one processor, cause the at least one processor to operate with the at least one input device, for each of the plurality of players, to enable said player to position one of the plurality of accumulators within the predefined field by inputting at least one selected from the group consisting of: a desired position of said accumulator, a desired orientation of said accumulator, a desired size of said accumulator, and a desired perimeter shape of said accumulator.

31. The gaming system of claim 25, wherein the plurality of instructions, when executed by the at least one processor, cause the at least one processor to operate with the at least one input device to enable at least one of the plurality of players to position one of the plurality of accumulators by inputting a desired position of one of a plurality of accumulator segments until said positioned accumulator segments form a closed geometric shape defining the perimeter of the accumulator.

32. The gaming system of claim 25, wherein the perimeter of said positioned accumulator has the designated spatial relationship with said emblem if the perimeter of said positioned accumulator completely encircles said emblem.

* * * * *

UNITED STATES PATENT AND TRADEMARK OFFICE
CERTIFICATE OF CORRECTION

Page 1 of 1

PATENT NO.         : 8,287,364 B2
APPLICATION NO.    : 12/270472
DATED              : October 16, 2012
INVENTOR(S)        : Scott A. Caputo et al.

It is certified that error appears in the above-identified patent and that said Letters Patent is hereby corrected as shown below:

IN THE CLAIMS

In Claim 8, Column 52, Line 5, replace "a" with --the--.
In Claim 8, Column 52, Line 10, replace "one of the" with --said-- and replace "emblems" with --emblem--.
In Claim 10, Column 52, Line 26, between "for" and "the" insert --each of--.
In Claim 13, Column 52, Line 52, replace "ahs" with --has--.
In Claim 22, Column 53, Lines 55 to 56, replace "each of the plurality of accumulator positioning criteria" with --the accumulator positioning criterion--.

Signed and Sealed this
Eighth Day of January, 2013

David J. Kappos
*Director of the United States Patent and Trademark Office*